United States Patent
Fujita

(10) Patent No.: US 8,419,614 B2
(45) Date of Patent: Apr. 16, 2013

(54) CAPSULE ENDOSCOPE

(75) Inventor: Manabu Fujita, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1036 days.

(21) Appl. No.: 12/400,274

(22) Filed: Mar. 9, 2009

(65) Prior Publication Data

US 2009/0171146 A1    Jul. 2, 2009

Related U.S. Application Data

(63) Continuation of application No. PCT/JP2007/067669, filed on Sep. 11, 2007.

(30) Foreign Application Priority Data

| Sep. 12, 2006 | (JP) | 2006-246834 |
| Sep. 19, 2006 | (JP) | 2006-252778 |
| Sep. 19, 2006 | (JP) | 2006-252779 |

(51) Int. Cl.
*A61B 1/00* (2006.01)
*A61B 1/06* (2006.01)

(52) U.S. Cl.
USPC .......................... 600/103; 600/160

(58) Field of Classification Search .......... 600/101–103, 600/109, 117–118, 160
See application file for complete search history.

(56) References Cited

U.S. PATENT DOCUMENTS

| 6,719,684 | B2 | 4/2004 | Kim et al. | |
| 6,904,308 | B2 | 6/2005 | Frisch et al. | |
| 7,007,327 | B2 | 3/2006 | Ogawa et al. | |
| 2004/0181127 | A1 * | 9/2004 | Matsumoto et al. | 600/101 |
| 2005/0171398 | A1 * | 8/2005 | Khait et al. | 600/102 |
| 2005/0222496 | A1 | 10/2005 | Sekiguchi | |
| 2006/0004255 | A1 * | 1/2006 | Iddan et al. | 600/160 |
| 2006/0056828 | A1 * | 3/2006 | Iddan et al. | 396/14 |
| 2007/0106112 | A1 * | 5/2007 | Gat et al. | 600/109 |
| 2007/0221233 | A1 * | 9/2007 | Kawano et al. | 128/899 |
| 2007/0232851 | A1 | 10/2007 | Fujimori et al. | |
| 2010/0010300 | A1 * | 1/2010 | Gilad | 600/109 |
| 2011/0034795 | A9 * | 2/2011 | Gilad et al. | 600/407 |

FOREIGN PATENT DOCUMENTS

| EP | 1 967 125 A1 | 9/2008 |
| JP | 7-289504 | 11/1995 |
| JP | 8-112242 | 5/1996 |
| JP | 2003-19111 | 1/2001 |
| JP | 2002-65765 | 3/2002 |

(Continued)

OTHER PUBLICATIONS

Japanese Office Action dated Jul. 31, 2012 from corresponding Patent Application No. JP 2008-534350.

(Continued)

*Primary Examiner* — Philip R Smith
(74) *Attorney, Agent, or Firm* — Scully Scott Murphy & Presser, PC

(57) ABSTRACT

A capsule endoscope system includes a capsule endoscope which is introduced into a subject; a change unit which changes a position or posture of the capsule endoscope in the subject with respect to the subject; a storage unit which stores in advance a change procedure of the capsule endoscope as a control parameter of the change unit; and a controller which controls the change unit in accordance with the parameter stored in the storage unit.

7 Claims, 27 Drawing Sheets

FOREIGN PATENT DOCUMENTS

| | | |
|---|---|---|
| JP | 2004-440 | 1/2004 |
| JP | 2004-121733 | 4/2004 |
| JP | 2004-121837 | 4/2004 |
| JP | 2004-298560 | 10/2004 |
| JP | 2005-103091 | 4/2005 |
| JP | 2005-103092 A | 4/2005 |
| JP | 2005-143991 A | 6/2005 |
| JP | 2005-270536 | 10/2005 |
| JP | 2005-312903 | 11/2005 |
| JP | 2006-20853 | 1/2006 |
| JP | 2006-068534 A | 3/2006 |
| WO | WO 2005/060348 A2 | 7/2005 |

OTHER PUBLICATIONS

English language abstract of Japanese Patent Application No. JP 2004-298560 A.

English language abstract of Japanese Patent Application No. JP 2005-312903 A.

European Search Report dated Feb. 21, 2013 from corresponding European Patent Application No. EP 07 80 7078.6.

\* cited by examiner

FIG.4

| POSTURE NUMBER | LENGTH OF LEG 151A | LENGTH OF LEG 151B | LENGTH OF LEG 151C | LENGTH OF LEG 151D | KEEPING TIME |
|---|---|---|---|---|---|
| 1 | 50 | 50 | 50 | 50 | 1 |
| 2 | 30 | 20 | 40 | 50 | 3 |
| ⋮ | ⋮ | ⋮ | ⋮ | ⋮ | ⋮ |
| n | 50 | 50 | 50 | 50 | 50 |

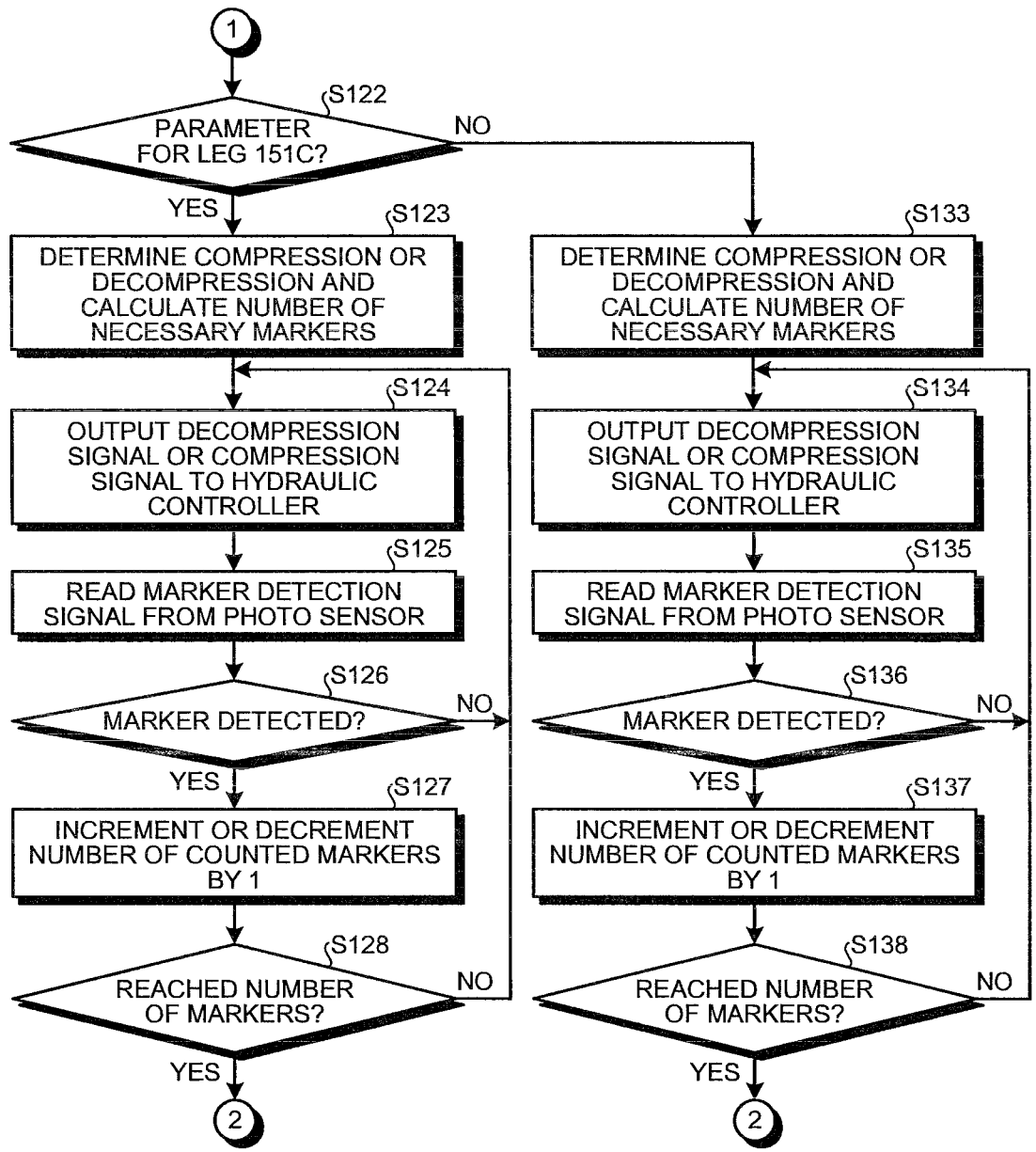

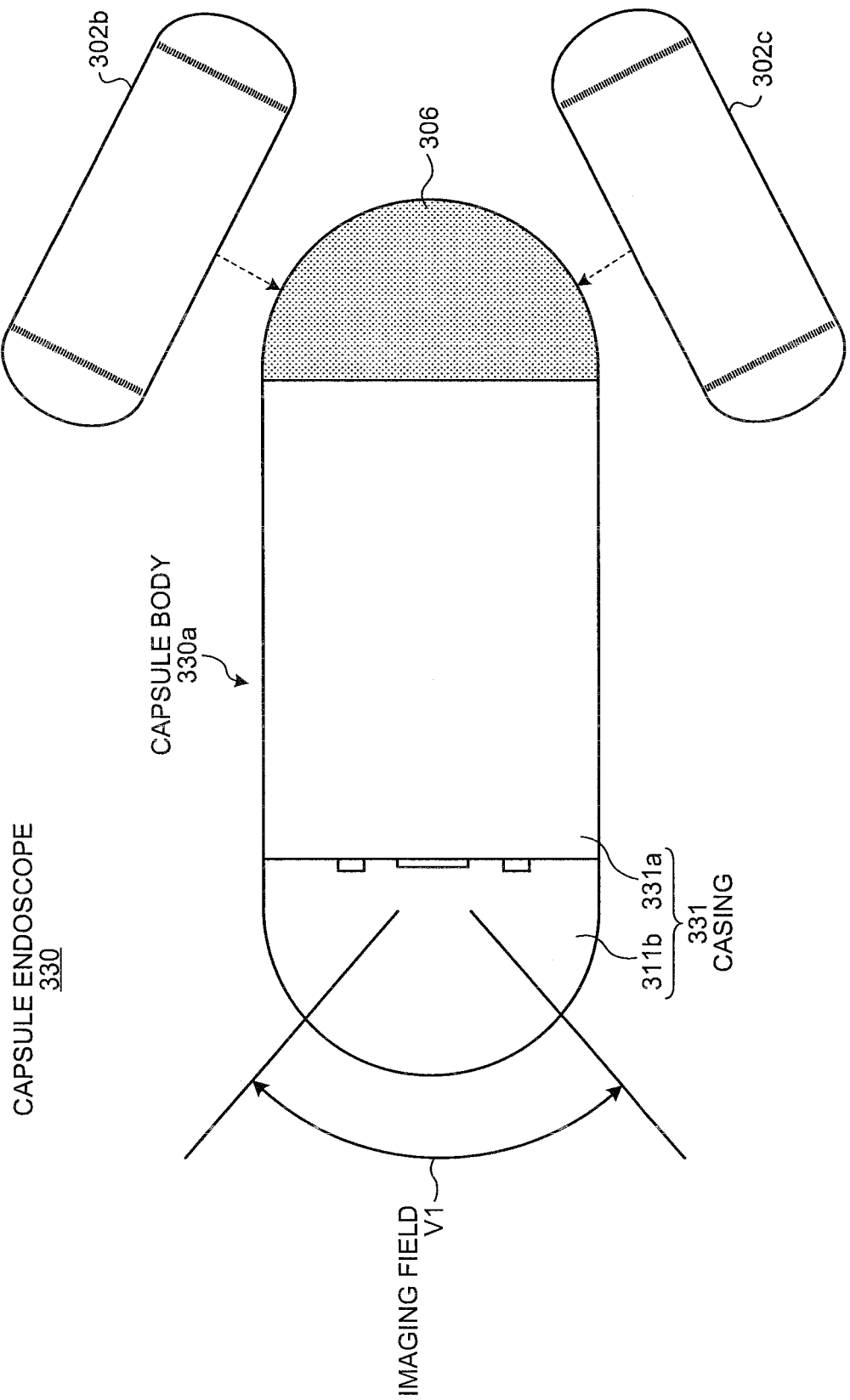

CAPSULE ENDOSCOPE

CROSS-REFERENCE TO RELATED APPLICATIONS

This application is a continuation of PCT international application Ser. No. PCT/JP2007/067669 filed on Sep. 11, 2007 which designates the United States, incorporated herein by reference, and which claims the benefit of priority from Japanese Patent Applications No. 2006-246834, filed on Sep. 12, 2006, No. 2006-252778, filed on Sep. 19, 2006, and No. 2006-252779, filed on Sep. 19, 2006, incorporated herein by reference.

BACKGROUND OF THE INVENTION

1. Field of the Invention

The present invention relates to a capsule endoscope system for observing the inside of a subject with a capsule endoscope introduced into the subject mounted on a mounting bed, an in-vivo information acquiring apparatus and the capsule endoscope for acquiring an internal image(s) of an organ imaged by the capsule endoscope introduced into the subject.

2. Description of the Related Art

In recent years, in the field of endoscopes, a capsule endoscope including an imaging function and a wireless communication function has appeared. The capsule endoscope is swallowed from a mouth of an examined person as a subject (human body) for observation (examination). After this, the capsule endoscope moves inside organs (body cavity) such as the esophagus, stomach, and small intestine by peristaltic movement of the organs, and sequentially performs imaging using the imaging function during an observation period until the capsule endoscope is naturally discharged from the living body of the subject.

For example, Japanese Patent Application Laid-Open Nos. 7-289504, 2004-298560, 2004-121837 and 2002-65765 disclose techniques as systems utilizing this type of capsule endoscope. Each of the systems has a gravity sensor installed in the capsule endoscope so as to detect the gravity direction. The system determines the luminal direction based on an endoscope image imaged by the capsule endoscope. The system inclines a bed in such a manner that the luminal direction agrees with the gravity direction. As a result, the system observes the subject while the physical position of the subject on the bed is inclined and the capsule endoscope is moved in the gravity direction.

This type of capsule endoscope sequentially images the internal image of the organ (hereinafter, sometimes referred to as an internal image of the subject) at an interval of, for example, 0.5 second in time series. The capsule endoscope in the subject sequentially and wirelessly sends the imaged internal image of the organ to a receiving device outside the subject.

This receiving device is attached onto the subject and acquires the internal images of the subject imaged by the capsule endoscope inside the subject while the capsule endoscope moves inside the subject. In this case, stick-on type receiving antennas are attached onto a plurality of spots (e.g. eight spots) on the body surface of the subject. The plurality of receiving antennas are connected to the receiving device carried by the subject through a cable or the like. This receiving device receives a wireless signal from the capsule endoscope through the plurality of receiving antennas, and acquires the internal images of the subject included in the received wireless signal.

A portable recording medium is detachably attached to the receiving device. The storage medium attached to the receiving device sequentially stores the internal images of the subject received by the receiving device from the capsule endoscope in the subject. After that, the storage medium having stored a group of internal images of the subject is removed from the receiving device and attached to a predetermined image display device.

The image display device having the storage medium attached thereinto reads the group of internal images of the subject stored on the storage medium, and displays the group of read internal images of the subject. In this case, a user (such as a doctor, or a nurse) controls the image display device to sequentially display the group of internal images of the subject thereon in time series. As a result, the user can observe (examine) the inside of the organ of the subject, and can diagnose the subject (see, for example, Japanese Patent Application Laid-Open No. 2003-19111).

This type of capsule endoscope includes a hook member that freely slides in and out and projects from a capsule casing so as to hook on the internal wall of the organ, or an expansion member that expands expandably and contractibly from the capsule casing so as to hook on the internal wall of the organ (see, for example, Japanese Patent Application Laid-Open No. 2004-440). This capsule endoscope is orally taken into the subject, and then sequentially moves along the organs inside the subject. When the endoscope reaches a particular examined region in the subject, the hook member or the expansion member hooks and stops on the internal wall of the organ. Because the capsule endoscope stops in the particular examined region, the capsule endoscope can precisely image the particular examined region.

This capsule endoscope may have a specific gravity set equal to or lower than 1 so as to image the internal image of the organ that the capsule endoscope floats on the water surface inside the organ of the subject. In this case, the capsule endoscope includes a floating member in place of the above-described hook member or expansion member, and has a specific gravity that becomes equal to or lower than 1 when the floating member expands.

Like the expansion member of the capsule endoscope disclosed in Patent Document 6, the floating member may be contained inside the casing so as to expand expandably and contractibly from the casing, or may be arranged outside the casing. The capsule endoscope may include, inside the casing, a space with a predetermined volume or larger so as to set the specific gravity of the capsule endoscope equal to or lower than 1.

SUMMARY OF THE INVENTION

A capsule endoscope system according to an aspect of the present invention includes a capsule endoscope which is introduced into a subject; a change unit which changes a position or posture of the capsule endoscope in the subject with respect to the subject; a storage unit which stores in advance a change procedure of the capsule endoscope as a control parameter of the change unit; and a control unit which controls the change unit in accordance with the parameter stored in the storage unit.

An in-vivo information acquiring apparatus according to another aspect of the present invention includes a capsule endoscope which is introduced into a subject; a supporting unit which supports the subject; a sending unit which is included in the capsule endoscope and sends data of an image imaged by the capsule endoscope; one or more receiving antenna which is included on the supporting unit; a receiving unit which receives the image data sent from the sending unit through the receiving antenna; a storing unit which stores the image data received by the receiving unit; a subject specification information input unit which is used to input specification information specifying the subject; an instruction unit which is used to instruct to start and end storing the image data; and a control unit which performs control to store, in the storing unit, the specification information and a series of image data received by the receiving unit in association with each other during a period since the instruction unit instructs to start storing until the instruction unit instructs to end the storage.

A capsule endoscope according to another aspect of the present invention includes a capsule casing which is introduced into a subject; a floating member which is introduced into the subject and has a specific gravity lower than 1 with respect to liquid in the subject; and an attaching unit which attaches the floating member to the capsule casing.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4 is an explanatory diagram showing an example of change parameters stored in a posture storage unit inside an EEPROM;

FIG. 5B is a schematic flowchart showing another part of the control example of operation of the change driving mechanism executed by the CPU;

FIG. 26 is a schematic diagram showing one modification of the capsule endoscope according to the present invention.

DETAILED DESCRIPTION OF THE PREFERRED EMBODIMENTS

Preferred embodiments of the present invention will now be specifically described with reference to the accompanying drawings.

First Embodiment

Figure 1:
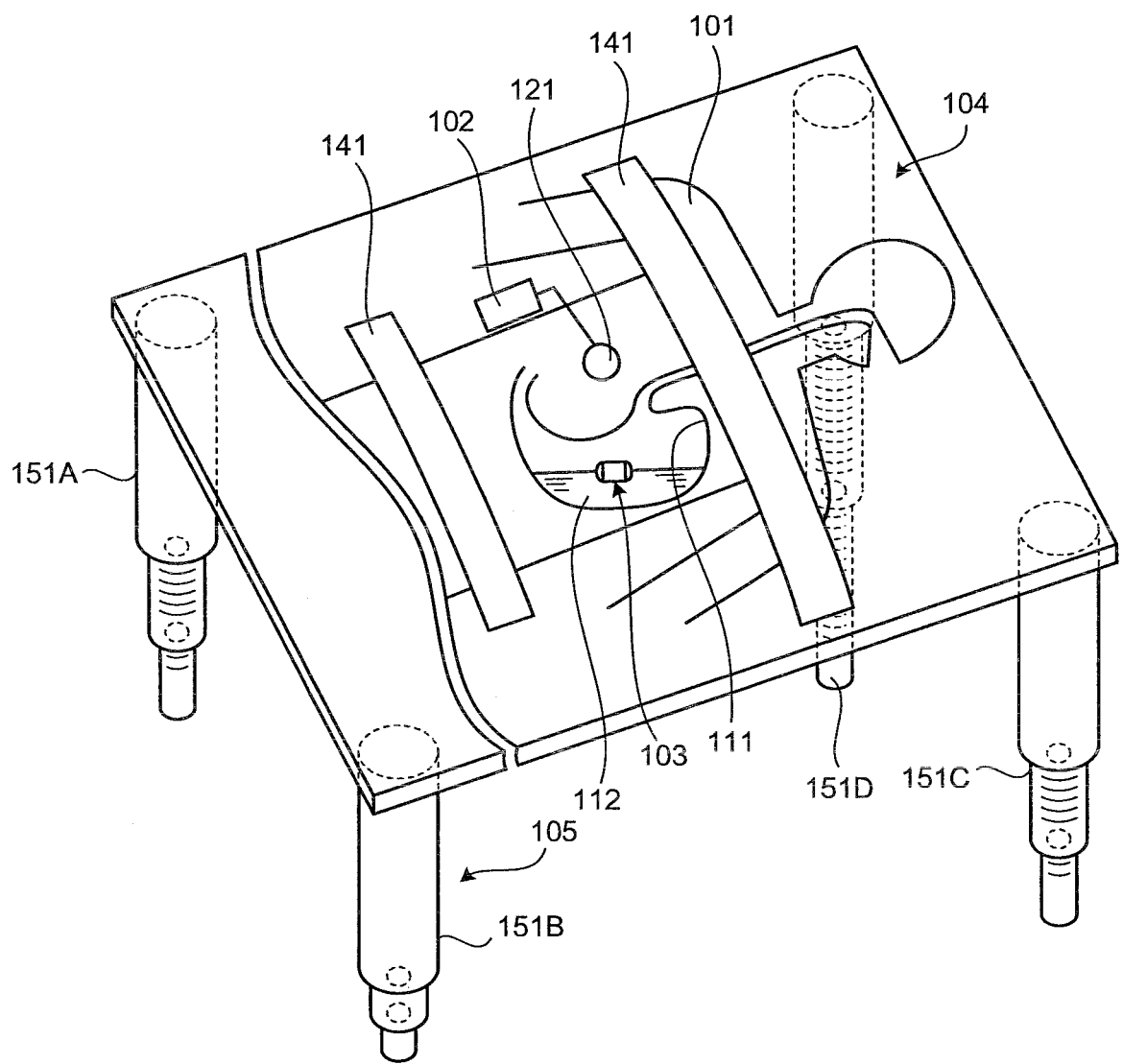
FIG. 1 is a schematic perspective diagram showing a configuration example of a capsule endoscope system according to a first embodiment of the present invention.
Figure 2:
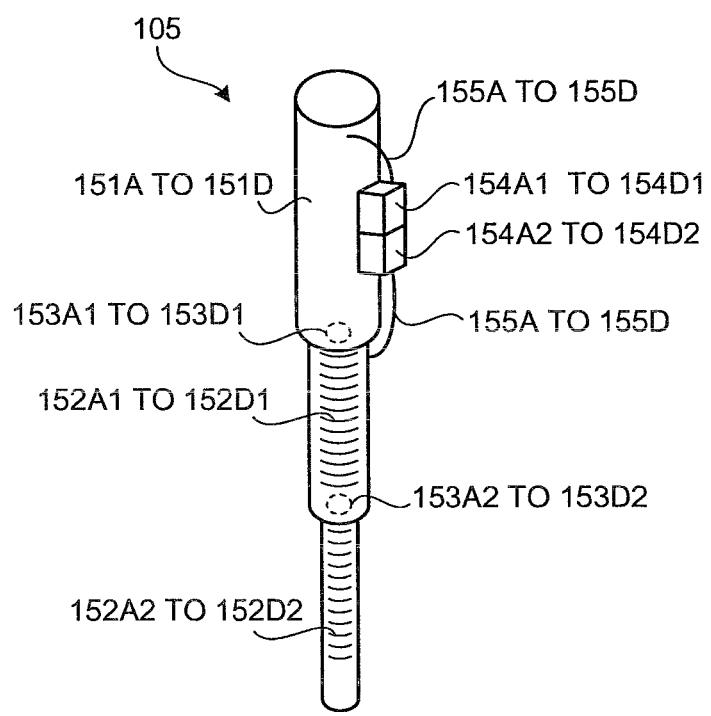
FIG. 2 is a schematic perspective diagram showing a configuration example of a posture change mechanism.

FIG. 1 is a schematic perspective diagram showing a configuration example of a capsule endoscope system according to a first embodiment, and FIG. 2 is a schematic perspective diagram showing a configuration example of a posture change mechanism. The capsule endoscope system according to the first embodiment of the present invention includes a capsule endoscope 103 introduced into a body cavity of a subject 101 so as to image the image inside the body cavity, and wirelessly sends image data of the internal image of the subject to a receiving device 102; the receiving device 102 that receives the image data wirelessly sent from the capsule endoscope 103; a bed 104 that functions as a mounting unit for mounting the subject 101, on his/her back, into which the capsule endoscope 103 is introduced; and a posture change mechanism 105 provided on the bed 104 and functions as a posture change unit for changing the posture of the bed 104 and inclining it in a front/back direction and a left/right direction, in order to change the posture of the subject 101 mounted on the bed 104 in the gravity direction.

The capsule endoscope 103 includes various constituent members such as an illuminating unit, an imaging unit, a communication unit, and a power source. The capsule endoscope 103 is of a size that can be swallowed by the subject 101 from his/her mouth. The internal configuration of the capsule endoscope 103 is a matter not directly related to the first embodiment. Thus, a conventionally known internal configuration may be used, and will not be specifically described here. Note that the capsule endoscope 103 of the first embodiment includes an illuminating unit and an imaging unit on both sides in the axial direction of the capsule, and is a compound-eye capsule endoscope which can perform imaging in both directions.

In the first embodiment, a stomach 111 is an example of the observed region as an organ having a relatively large space inside the subject 101. The capsule endoscope 103 is configured to observe and perform imaging inside of the stomach 111 while floating on liquid 112 such as drinking water introduced from the mouth to the stomach 111. For example, the capsule endoscope 103 is configured to always float in a horizontal direction on the surface of the liquid 112 in accordance with the setting of a specific gravity with respect to the liquid 112, the center of gravity, or the like. Accordingly, the endoscope 103 is kept in a predetermined posture so that the observation direction in two directions by the compound eye is always in a horizontal direction with respect to the gravity direction.

The receiving device 102 includes a receiving antenna 121 such as a loop antenna to be attached on the external surface of the subject 101. The receiving device 102 receives image data or the like which has been wirelessly sent from the capsule endoscope 103 through the receiving antenna 121.

The bed 104 has a sufficient size to mount the subject 101 on his/her back, and includes a fixing belt 141 for fixing the subject 101 so that the mounting position of the mounted subject 101 does not move over even if the posture of the bed 104 inclines.

The posture change mechanism 105 includes four extensible legs 151A to 151D which are provided respectively on the lower four corners of the bed 104. The legs 151A to 151D have the same configuration, for example, a three-stage extension configuration as shown in FIG. 2. The legs have attached markers 152A1 to 152D1 and 152A2 to 152D2 of scales for measuring the length when the legs 151A to 151D are extended and shortened, and have also photo sensors 153A1 to 153D1 and 153A2 to 153D2 for detecting the position of each of the current markers 152A1 to 152D1 and 152A2 to 152D2. The posture change mechanism 105 includes hydraulic controllers 154A1 to 154D1 that drive the legs 151A to 151D in the extending direction; hydraulic controllers 154A2 to 154D2 that drive the legs 151A to 151D in the shortening direction; and hydraulic transmission pipes 155A to 155D that couple between these legs 151A to 151D and the hydraulic controllers 154A1 to 154D1 and 154A2 to 154D2. Thereby, when the hydraulic controllers 154A2 to 154D2 are compression driven, the legs 151A to 151D are shortened, and when the hydraulic controllers 154A1 to 154D1 are decompression driven, the legs 151A to 151D are extended. The lengths of the legs 151A to 151D are individually controlled so as to extend and shorten, and thus the posture of the bed 104 can be changed and inclined in a front/back direction and a left/right direction.

Figure 3:
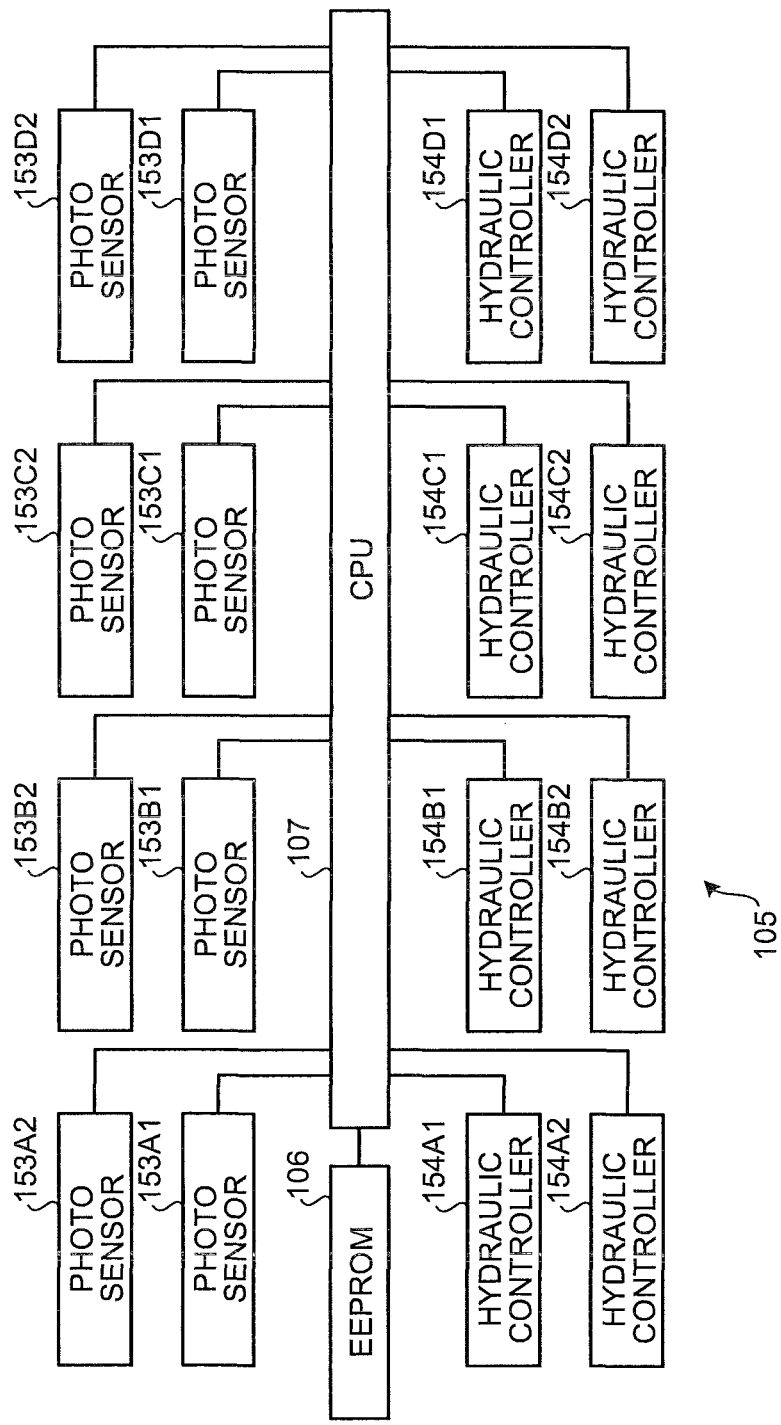
FIG. 3 is a schematic block diagram showing a configuration example of a control system for the posture change mechanism.

FIG. 3 is a schematic block diagram showing a configuration example of a control system for the posture change mechanism 105. The capsule endoscope system of the first embodiment includes, as a control system for the posture change mechanism 105, an EEPROM (Electrically Erasable and Programmable Read Only Memory) 106 as a storage unit that stores change parameters for each change posture of the posture change mechanism 105, the parameters being determined in advance in accordance with a previously set observation direction inside the subject 101 by the capsule endoscope 103; and a CPU 107 as a control unit that controls a change operation of the posture change mechanism 105 using the change parameters stored in the EEPROM 106.

FIG. 4 is an explanatory diagram showing an example of change parameters stored in a posture storage unit 161 in the EEPROM 106. In the first embodiment, the change parameter includes length information representing a change amount of each of the legs 151A to 151D for each change posture specified by a posture number n, and a keeping time for keeping the change posture is stored for each change posture. "N" (from 1 to N) posture numbers n are stored as one change parameter representing a previously determined change order for each change posture.

For example, according to the example shown in FIG. 4, in the first change posture represented by a posture number 1, each of the legs 151A to 151D is set to have the maximum initial length of 50 (cm), and the keeping time is set to 1 (min). In the second change posture represented by a posture number 2, the leg 151A is set to be shortened to the length of 30 (cm), the leg 151B is set to be shortened to the length of 20 (cm), the leg 151C is set to be shortened to the length of 40 (cm), the leg 151D is kept at the same length of 50 (cm), and the keeping time is set to 3 (min).

Figure 5A:
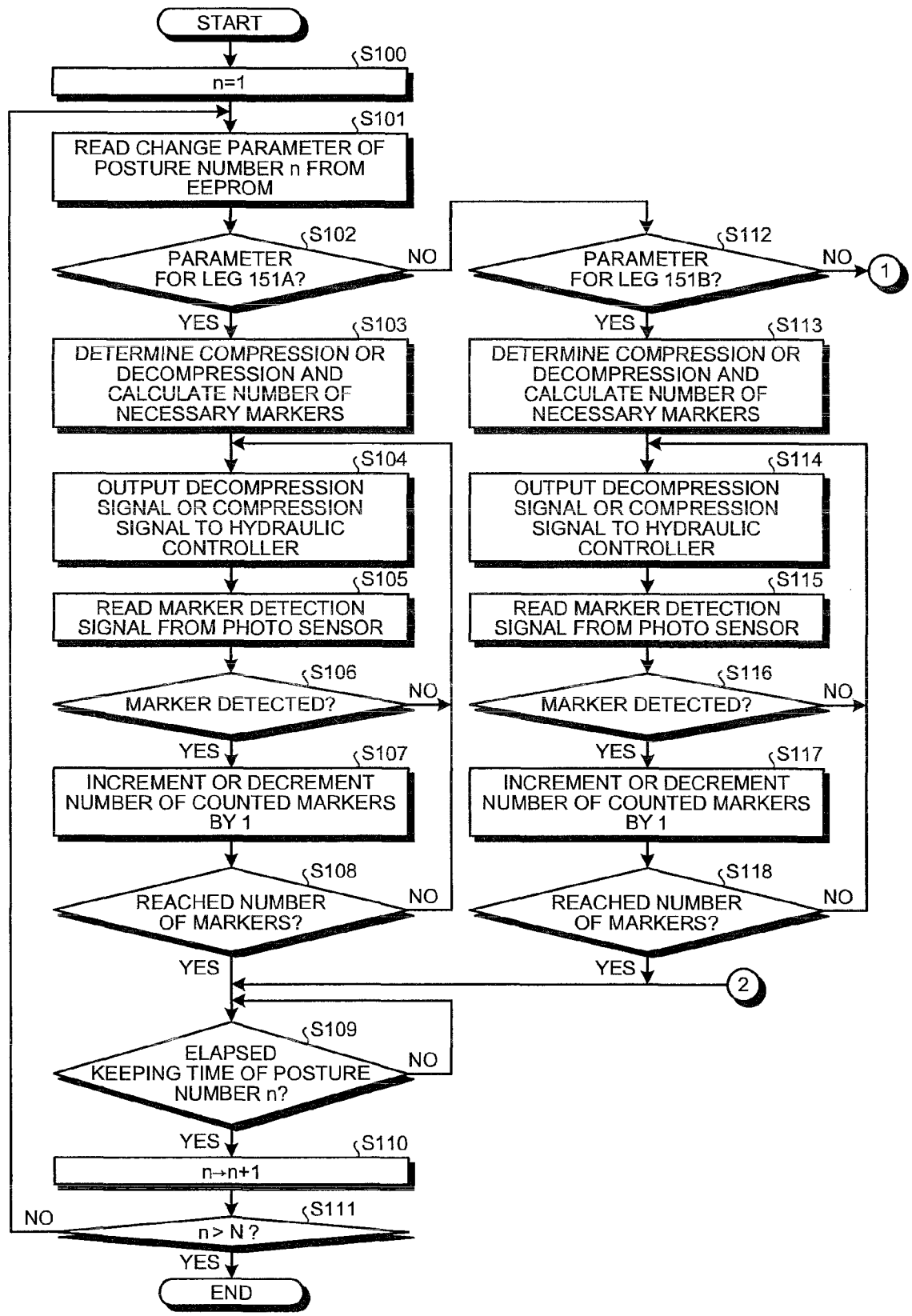
FIG. 5A is a schematic flowchart showing a part of a control example of operation of a change driving mechanism executed by a CPU.

FIGS. 5A and 5B are schematic flowcharts showing a control example of operation of the change drive mechanism 105 which is executed by the CPU 107 based on the change parameters stored in the EEPROM 106. Once observation begins in a state that the subject 101 who has swallowed the liquid 112 and the capsule endoscope 103 is mounted on his/her back on the bed 104, the posture number representing the change order is set to n=1 (Step S100). Next, a change parameter of the change number n is read from the posture storage unit 161 of the EEPROM 106 (Step S101). In other words, length information and keeping time of the legs 151A to 151D corresponding to the posture number n are read. If length data about the leg 151A is read (Step S102: Yes), it is determined whether compression or decompression is performed based on the length data, the number of markers necessary for the change is calculated (Step S103), and a decompression signal or a compression signal is sent and output to the hydraulic controller 154A1 or 154A2 (Step S104). A marker detection signal from the photo sensor 153A1 or 153A2 is read out (Step S105). When the marker 152A1 or 152A2 is detected (Step S106: Yes), the number of counted markers is decremented by 1 in the case of decompression, and the number is incremented by 1 in the case of compression (Step S107). This process is repeated until reaching the previously calculated number of necessary markers (Step S108: Yes), and thus the length of the leg 151A is extended and shortened so as to coincide with the length data.

Concurrently with the above process, for the length data about the leg 151B (Step S102: No, Step S112: Yes), it is determined whether compression or decompression is performed based on the length data, the number of markers necessary for the change is calculated (Step S113), and a decompression signal or a compression signal is sent and output to the hydraulic controller 154B1 or 154B2 (Step S114). A marker detection signal is read out from the photo sensor 153B1 or 153B2 (Step S115). When a marker 152B1 or 152B2 is detected (Step S116: Yes), the number of counted markers is decremented by 1 in the case of decompression, and the number is incremented by 1 in the case of compression (Step S117). This process is repeated until reaching the previously calculated number of necessary markers (Step S118: Yes), and thus the length of the leg 151B is extended and shortened so as to coincide with the length data.

Concurrently with the above process, for the length data about the leg 151C (Step S112: No, Step S122: Yes), it is determined whether compression or decompression is performed based on the length data, the number of markers necessary for the change is calculated (Step S123), and a decompression signal or a compression signal is sent and output to the hydraulic controller 154C1 or 154C2 (Step S124). A marker detection signal is read out from the photo sensor 153C1 or 153C2 (Step S125). When a marker 152C1 or 152C2 is detected (Step S126: Yes), the number of counted markers is decremented by 1 in the case of decompression, and the number is incremented by 1 in the case of compression (Step S127). This process is repeated until reaching the previously calculated number of necessary markers (Step S128: Yes), and thus the length of the leg 151C is extended and shortened so as to coincide with the length data.

Furthermore, concurrently with the above process, for the length data about the leg 151D (Step S122: No), it is determined whether compression or decompression is performed based on the length data, the number of markers necessary for the change is calculated (Step S133), and a decompression signal or a compression signal is sent and output to the hydraulic controller 154D1 or 154D2 (Step S134). A marker detection signal is read out from the photo sensor 153D1 or 153D2 (Step S135). When a marker 152D1 or 152D2 is detected (Step S136: Yes), the number of counted markers is decremented by 1 in the case of decompression, and the number is incremented by 1 in the case of compression (Step S137). This process is repeated until reaching the previously calculated number of necessary markers (Step S138: Yes), and thus the length of the leg 151D is extended and shortened so as to coincide with the length data.

When extending and shortening of the length of each of the legs 151A to 151D is controlled by such a concurrent process based on the change parameter stored in the EEPROM 106, the changed posture is kept until elapse of the keeping time set for the corresponding posture number n. The posture of the subject 101 mounted on the bed 104 is changed with respect to the gravity direction in accordance with the changed posture of the bed 104. Specifically, the position of the surface (horizontal surface) of the liquid 112 introduced into the stomach 111 is changed, and the observed region of the capsule endoscope 103 floating on the surface of the liquid 112 is changed. Upon elapse of the keeping time (Step S109: Yes), the posture number n is incremented by +1 (Step S110). If the final posture number n=N is not reached (Step S111: No), the above change driving is similarly repeated for the next posture number n.

Figure 6:
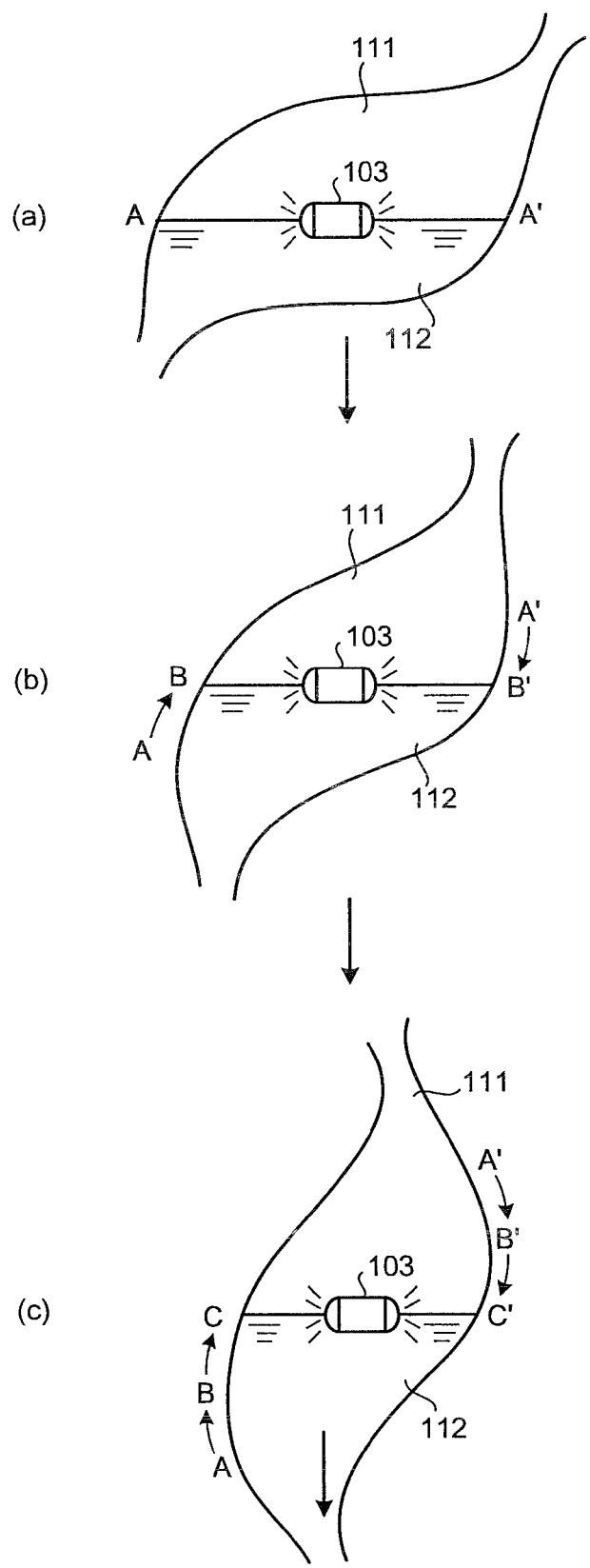
FIG. 6 is an explanatory diagram schematically showing an observation state inside a stomach, using a capsule endoscope.

FIG. 6 is an explanatory diagram schematically showing an observation state inside the stomach 111 using the capsule endoscope 103 when the posture of the subject 101 is sequentially changed in accordance with the above-described posture change of the bed 104 by the posture change mechanism 105. For example, as shown with the change posture corresponding to a posture number 1 in FIG. 6(a), after the capsule endoscope 103 whose observation direction is a horizontal direction has imaged and observed the observed regions A and A' inside the stomach 111 for one minute, the posture change mechanism 105 is operated so as to change the posture of the subject 101 into a posture corresponding to a posture number 2 in FIG. 6(b). In the change posture shown in FIG. 6(b), the capsule endoscope 103 (whose observation direction is a horizontal direction) images and observes the observed regions B and B' inside the stomach 111, and performs imaging and observation in this posture for three minutes. Subsequently, the posture change mechanism 105 is operated so as to change the posture of the subject 101 into a posture corresponding to a posture number 3 shown in FIG. 6(c). In the change posture shown in FIG. 6(c), the capsule endoscope 103 (whose observation direction is a horizontal direction) images and observes the observed regions C and C' inside the stomach 111, and performs imaging and observation in the posture for a set period of time. The same procedure is repeated. Accordingly, one imaging unit of the capsule endoscope 103 images and observes A, B, C, ... sequentially as the observed regions inside the stomach 111, while the other imaging unit of the capsule endoscope 103 images and observes A', B', C', ... sequentially as the observed regions inside the stomach 111.

As described above, the capsule endoscope system according to the first embodiment includes the posture change mechanism 105 which changes the posture of the bed 104 so as to change the posture of the subject 101 mounted on the bed 104 with respect to the gravity direction. The system stores in the EEPROM 106 the change parameters for each change posture of the posture change mechanism 105 determined in advance in accordance with the previously set observation direction inside the stomach 111 of the subject 101 using the capsule endoscope 103. The system controls the change operation of the posture change mechanism 105 with previously stored change parameters, using the CPU 107. As a result, the posture of the bed 104 can be changed in such a manner that the posture of the subject 101 is in an observation direction for the previously set observed regions A, B, C, ..., and A', B' C', .... Therefore, the observation direction for the observed region is set in advance, the change parameters for each change posture of the posture change mechanism 105 are determined in accordance with the set direction and stored in the EEPROM 106, and thus it becomes possible to observe throughout the inside of an organ(s) like the stomach 111 having a relatively large space.

Particularly, in the first embodiment, using the liquid 112, the capsule endoscope 103 is floated horizontally on the surface of the liquid 112. Thus, the surface (horizontal surface) of the liquid 112 coincides with the observation direction of the capsule endoscope 103, and the change posture of the subject 101 can be controlled by controlling the surface position (horizontal surface) of the liquid 112 with respect to a desired observation region.

The posture of the bed 104 is changed in a previously determined changing order in accordance with the posture number. The postures can be changed in a shorter changing time than that in the case of performing the change in a random order, and thus the observation time of the observation throughout the inside of the stomach 111 can be reduced. Because the change parameters stored in the EEPROM 106 include the keeping time for each change posture, a long keeping time can be set for observing throughout a region which is difficult to be observed or the like. It becomes possible to perform observation in an optimum observation time for each change posture.

Figure 7:
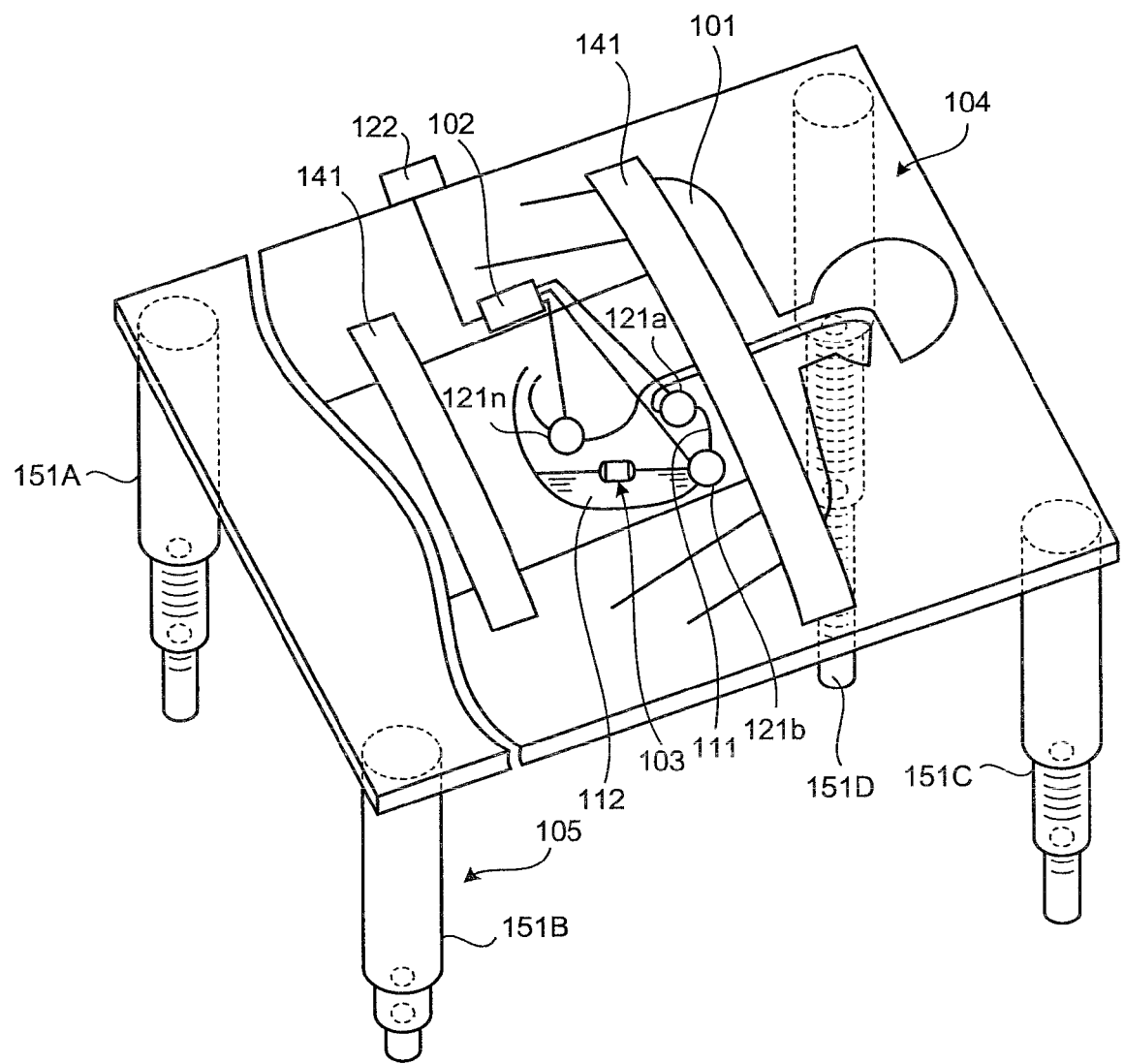
FIG. 7 is a schematic perspective diagram showing a configuration example of a capsule endoscope system according to a modification.
Figure 8:
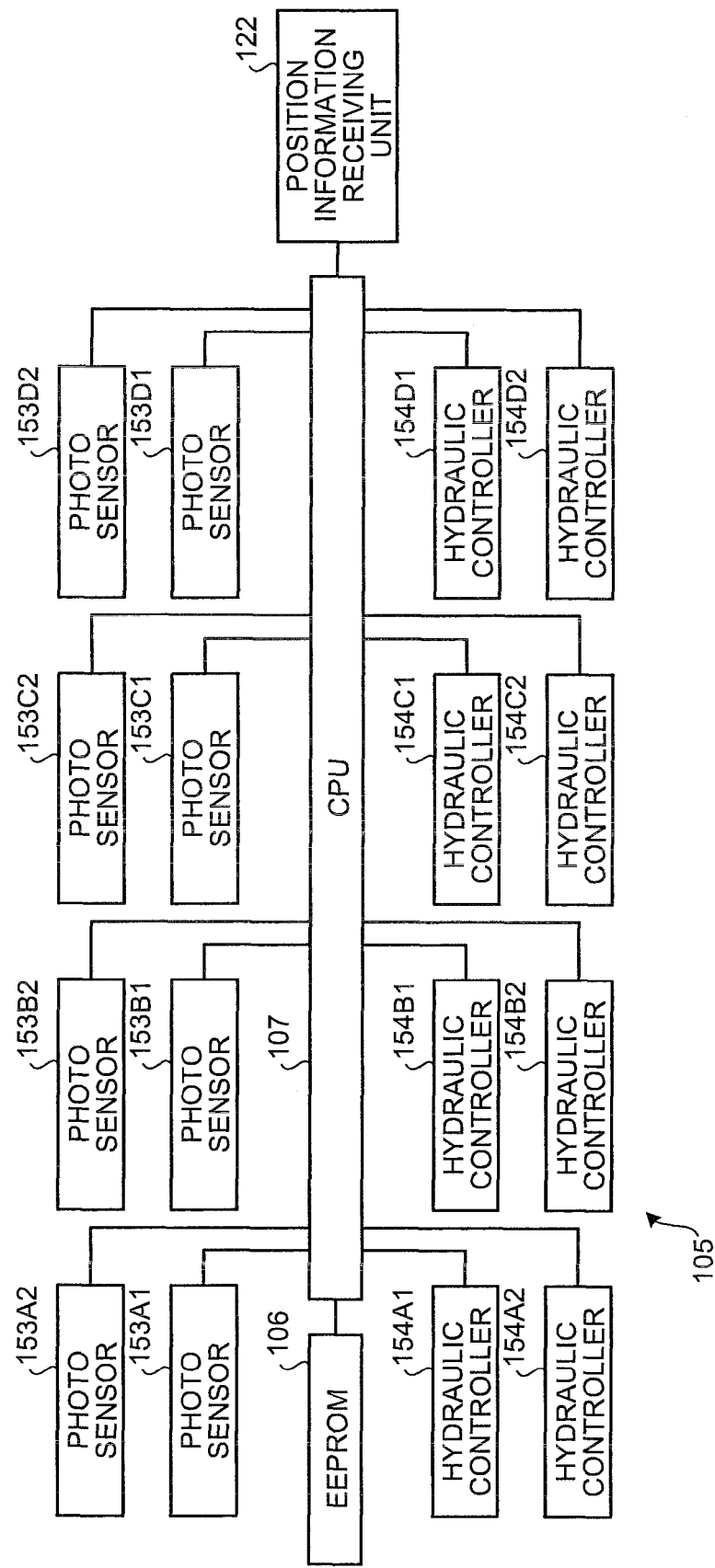
FIG. 8 is a schematic block diagram showing a configuration example of a control system for a posture change mechanism according to the modification.

The present invention is not limited to the first embodiment. Various modifications are possible without departing from the scope of the present invention. For example, as shown in FIG. 7, a plurality of receiving antennas 121a to 121n may be attached onto a body surface region near the stomach 111 that is an observed region inside the subject 101. The receiving device 102 may acquire also information on the received signal strength of each of the receiving antennas 121a to 121n at the time image data is received from the capsule endoscope 103 through each of the receiving antennas 121a to 121n so as to confirm the position of the capsule endoscope 103 in accordance with the posture change of the subject 101, using a position information receiving unit 122 connected to the receiving device 102. Further, as shown in FIG. 8, the position information in this position information receiving unit 122 may be taken into the CPU 107, and when a change amount of the posture change mechanism 105 is calculated based on the change parameters for each change posture stored in the EEPROM 106, the position information detected by the position information receiving unit 122 may be added so as to add fine adjustment to the change parameters. Thereby, the capsule endoscope 103 can be brought closer to a target position.

In the first embodiment, the position of the center of gravity is so set that the compound-eye capsule endoscope 103 floats horizontally on the surface of the liquid 112. However, the position of the center of gravity may be so set that the capsule endoscope 103 floats vertically or obliquely on the surface of the liquid 112. The capsule endoscope 103 may perform observation in the air, in the liquid, or both in the air and the liquid, in accordance with the floating state. Furthermore, it is not limited to the compound-eye capsule endoscope 103. A single eye capsule endoscope including an imaging unit or the like only on one end thereof is possible. In this case, the floating state with respect to the liquid 112 is the same.

Furthermore, in the first embodiment, the posture change mechanism 105 changing the posture of the bed 104 is explained as a mechanism having the four legs 151A to 151D as the base by way of example. However, the mechanism is not limited to one having the four extensible legs 151A to 151D. For example, the mechanism may be configured by combining a biaxial rotation supporting mechanism which rotatably supports the bed 104 on the horizontal plane.

In the first embodiment, the inclination of the bed (mounting bed) is changed, and thus the posture of the capsule endoscope in the subject is controlled. However, the posture and position of the capsule endoscope in the subject may be controlled with a magnetic field generated by a magnetic field generation device by installing a permanent magnet inside the capsule endoscope, and providing a magnetic field controller which controls a magnetic field generated by the magnetic field generation device and a magnetic field generation unit outside the subject.

At this time, a storage unit which stores in advance as a parameter a value for uniquely determining the intensity, direction and/or distribution of the magnetic field generated by the magnetic field controller (the posture or position of the magnetic field generation unit, current flowing in an electromagnet when the magnetic field generation unit is an electromagnet) may be calculated. The magnetic field controller may control the magnetic field generation unit in accordance with a parameter included in the storage unit. Accordingly, the capsule endoscope can move through a previously set path in a previously set posture inside the subject, and it becomes possible to observe throughout the inside of the organ such as a stomach having a relatively large space.

As in the first embodiment, the mounting bed may be controlled to be in postures in a previously set order, and the storage unit may store the postures of the mounting bed in association with parameters of the generated magnetic fields. The postures of the mounting bed and the generated magnetic fields may be controlled in accordance with the parameters stored in the storage unit. As a result, it becomes possible to more securely observe throughout the inside of the organs with a relatively large space.

Furthermore, in the first embodiment, the specific gravity is so set that the capsule endoscope floats in the water. However, the configuration is not limited to this, and the specific gravity and the center of gravity of the capsule endoscope may be so set that the endoscope is in a predetermined posture in a state that the capsule endoscope sinks under water. Also in this case, even when the posture of the subject is changed, the posture of the capsule endoscope is not changed with respect to the gravity direction, and thus the viewing field of the capsule endoscope can be switched. As a result, it becomes possible to observe throughout the inside of the organs with large spaces.

A preferred embodiment of an in-vivo information acquiring apparatus according to the present invention is explained with reference to the drawings. An embodiment of the present invention is explained as an in-vivo information acquiring apparatus of an aspect integrated with a bed (examining table) on which a subject such as a patient or the like, lies. However, the present invention is not limited to the embodiment.

Second Embodiment

Figure 9:
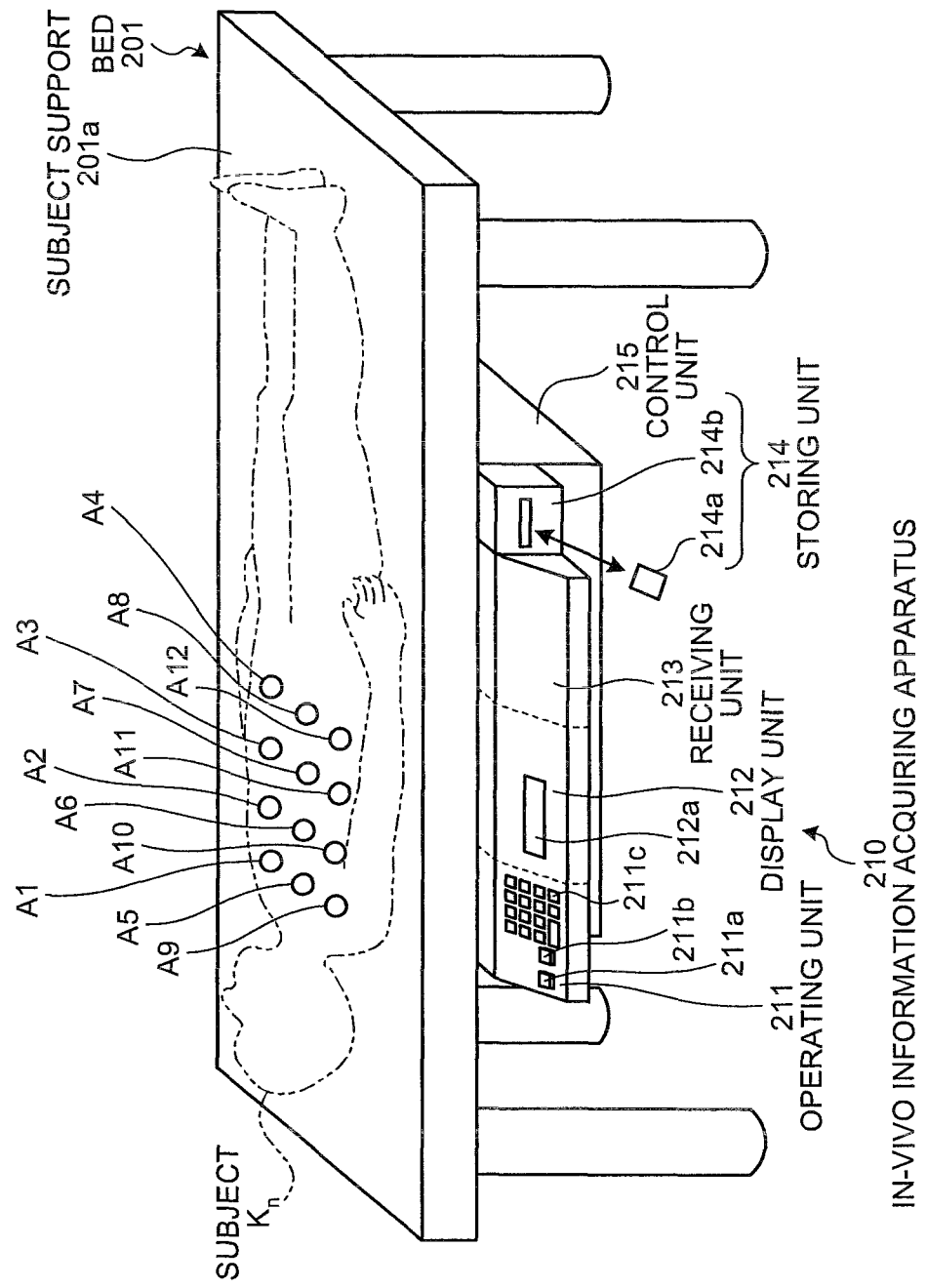
FIG. 9 is an external appearance schematic diagram showing a configuration example of an in-vivo information acquiring apparatus according to a second embodiment of the present invention.
Figure 10:
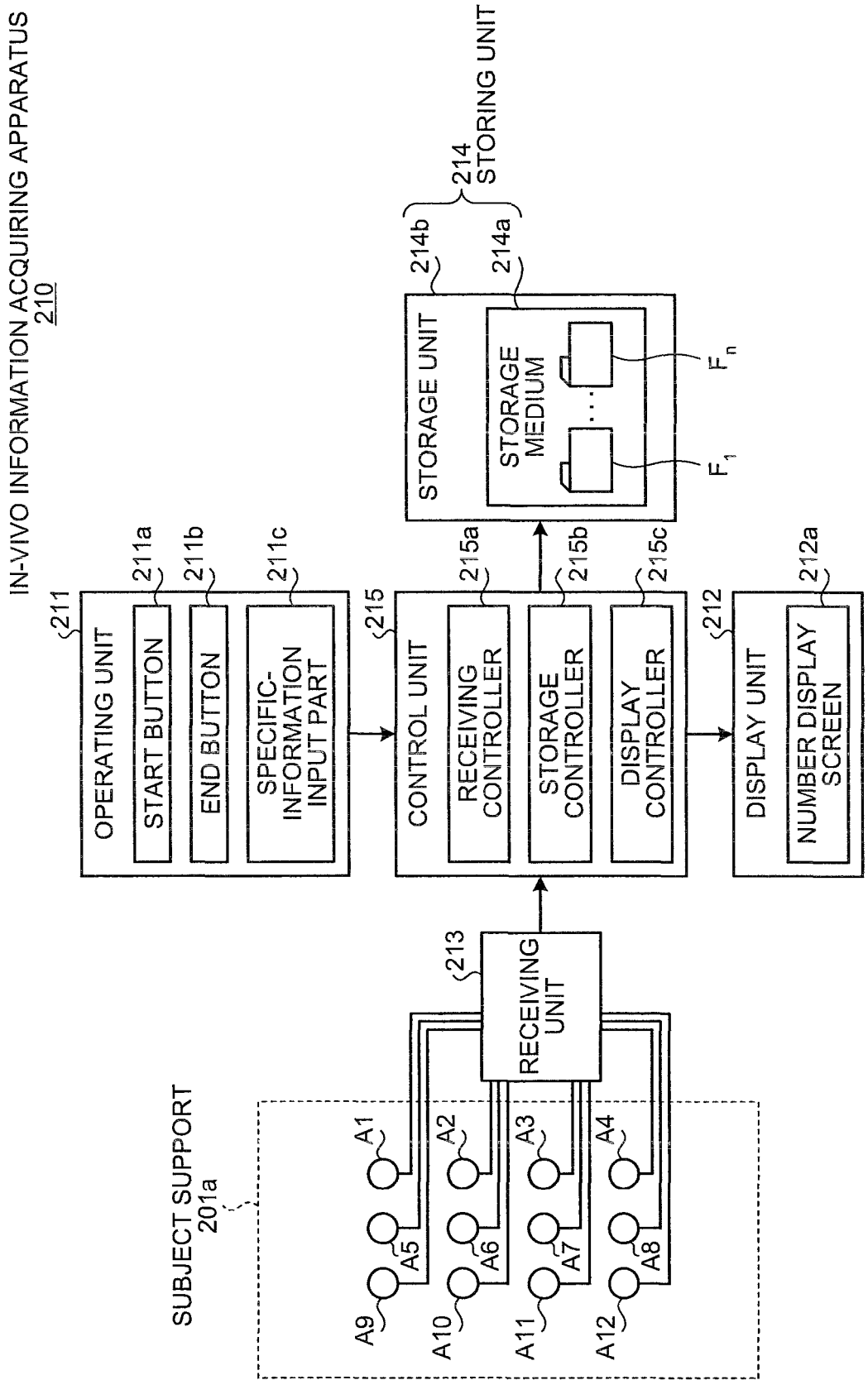
FIG. 10 is a block diagram showing an example of a function configuration of the in-vivo information acquiring apparatus according to the first embodiment of the present invention.

FIG. 9 is an external appearance schematic diagram showing a configuration example of an in-vivo information acquiring apparatus according to a second embodiment of the present invention. FIG. 10 is a block diagram showing an example of a function configuration of the in-vivo information acquiring apparatus according to the second embodiment of the present invention. An in-vivo information acquiring apparatus 210 according to the second embodiment is an apparatus for acquiring an internal image of an organ in a subject $K_n$ such as a patient having an organ into which the capsule endoscope is introduced, and is integrated with a bed 201 on which examined subjects $K_n$ (n=1, 2, 3, ... ) sequentially are laid. Specifically, as shown in FIGS. 9 and 10, this in-vivo information acquiring apparatus 210 includes the bed 201 that supports the subjects $K_n$ having an organ into which the capsule endoscope is introduced and a plurality of receiving antennas A1 to A12 that are attached onto a subject support 201a of this bed 201. The in-vivo information acquiring apparatus 210 has an operating unit 211 that operates input of a patient number specifying the examined subject $K_n$, and operates start and end of the storage of an image (i.e. an internal image of an organ) inside the subject $K_n$; a display unit 212 that displays the patient number of the subject $K_n$; a receiving unit 213 that receives the internal image of the subject $K_n$ through the plurality of receiving antennas A1 to A12; a storing unit 214 that stores the internal image of the subject $K_n$ received by the receiving unit 213; and a control unit 215 that controls each constituent unit of the in-vivo information acquiring apparatus 210.

The bed 201 supports the subject $K_n$ having the organ into which the capsule endoscope is introduced, and is a supporting unit which has the plurality of receiving antennas A1 to A12 fixed and arranged near an examined region in the supported subject $K_n$. Specifically, the bed 201 is a diagnostic bed for letting a plurality of subjects $K_1, K_2, \ldots, K_n$ (each having an organ into which the capsule endoscope is introduced) sequentially lie thereon, and has the plurality of receiving antennas A1 to A12 on the subject support 201a which sequentially supports the subjects $K_1, K_2, \ldots, K_n$.

The receiving antennas A1 to A12 are attached on the subject support 201a of the bed 201, for example, in a grid pattern. Specifically, the receiving antennas A1 to A12 attached onto the subject support 201a are fixed and arranged near an examined region (a target organ to be examined into which the capsule endoscope is introduced) in the subjects $K_1, K_2, \ldots, K_n$ lying on this subject support 201a. In this case, the receiving antennas A1 to A12 are positioned near the capsule endoscope in the examined region of the subject $K_n$ lying on the subject support 201a. One or more receiving antenna may be fixed and arranged near the examined region in the subject $K_n$, and the number of the antennas to be arranged is not particularly limited to twelve.

The capsule endoscope is a device having an imaging function and a wireless communication function in the capsule casing. When this capsule endoscope is introduced in the organ of the subject $K_n$, the capsule endoscope sequentially images the internal images of this organ, and sequentially sends a wireless signal including the images of the imaged organ to the outside.

The operating unit 211 is to operate input of a patient number for specifying the examined subject $K_n$ and also operate start and end of the storage of an internal image of the organ imaged by the capsule endoscope inside the subject $K_n$. The operating unit 211 functions as a specification information input unit that sends a patient number for specifying the examined subject $K_n$ to the control unit 215, and an instruction unit that instructs the control unit 215 to start and end the storage of the internal image of the organ. Specifically, the operating unit 211 has a specification information input unit 211c such as numerical keys for inputting a patient number of the examined subject $K_n$ to be laid on the bed 201; a start button 211a for operating start of the storage of the internal image of the subject $K_n$ currently lying on the bed 201; and an end button 211b for operating end of the storage of the internal image of the subject $K_n$. The specification information input unit 211c is used for inputting the patient number when the examined subject $K_n$ lies on the bed 201. The operating unit 211 sends the patient number of this subject $K_n$ to the control unit 215. The start button 211a is pressed to start storing the internal image of the organ imaged by the capsule endoscope inside the subject $K_n$ currently lying on the bed 201 in the storing unit 214. When the start button 211a is pressed, the operating unit 211 inputs, to the control unit 215, start instruction information for instruction to start an image storage process for storing the internal image of the organ in this subject $K_n$ in the storing unit 214. In this manner, the operating unit 211 instructs the control unit 215 to start storing the internal image of the organ in this subject $K_n$. The end button 211b is pressed to end storing the internal image of the organ in this subject $K_n$ in the storing unit 214. When this end button 211b is pressed, the operating unit 211 inputs, to the control unit 215, end instruction information for instruction to end the image storage process about this subject $K_n$. In this manner, the operating unit 211 instructs the control unit 215 to end storing the internal image of the organ in the subject $K_n$.

The display unit 212 has a number display screen 212a for displaying the patient number of the subject $K_n$. Such a display unit 212 displays, on the number display screen 212a, the patient number of the subject $K_n$, who is laid on the bed 201 in order to acquire the internal image of the organ from the capsule endoscope introduced into the organ, and displays also, on the number display screen 212a, the patient numbers input from the specification information input unit 211c corresponding to "n" respective subjects $K_1, K_2, \ldots, K_n$ who sequentially lie on this bed 201. In other words, the display unit 212 displays, on the number display screen 212a, the patient number of the examined subject $K_n$ to be laid on the bed 201 in order to acquire the internal image of the organ from the capsule endoscope introduced into the organ. In the second embodiment, the display unit 212 displays the contents for informing the completion of storage of the image for each patient number, on the number display screen 212a.

The patient number displayed on this number display screen 212a is for example a number given to each of a plurality of examined subjects (e.g. a number representing the sequential order of the patient) when the capsule endoscope is introduced into each of the plurality of subjects so as to acquire a group of internal images of the organ from each subject. The number is an example of specification information for specifying each of the plurality of subjects. The number display screen 212a which displays such patient numbers functions as a specification information display unit for sequentially displaying specification information about the plurality of subjects for a group medical examination (i.e. specification information specifying each examined subject to be laid on the bed 201).

The receiving unit 213 functions as a receiving unit for sequentially receiving internal images of the organ imaged by the capsule endoscope in the subject $K_n$ currently lying on the bed 201. Specifically, the receiving unit 213 is connected to the plurality of antennas A1 to A12 attached to the subject support 201a of the bed 201 through a cable or the like. In this case, the receiving unit 213 sequentially receives the internal images of the organ (i.e. the images of the examined region) imaged by the capsule endoscope in the subject $K_n$ currently lying on the bed 201. In this case, the receiving unit 213 receives a wireless signal sent by the capsule endoscope in the examined region in the subject $K_n$ through the receiving antennas A1 to A12, and performs a demodulation process on the received wireless signal so as to acquire the internal images of the organ included in this wireless signal. Accordingly, the receiving unit 213 sequentially receives the internal images of the organ imaged by the capsule endoscope in the examined region in the subject $K_n$. The receiving unit 213 sequentially sends the received internal images of the organ to the control unit 215.

The storing unit 214 functions as a storing means for storing the internal images of the organ received by the receiving unit 213. Specifically, the storing unit 214 has a storage medium 214a that stores the internal images of the organ separately for each subject and a storage unit 214b (such as drive) provided for detachably attaching the storage medium 214a thereto. The storage medium 214a is a portable recording medium such as "CompactFlash" (registered trademark), and is detachably attached to the storage unit 214b. The storage medium 214a attached to the storage unit 214b sequentially stores the internal images of the organ received by the receiving unit 213 separately for each subject. In this case, the storage medium 214a has folders $F_1, \ldots, F_n$ formed for each examined subject, and stores the group of images of the subjects $K_1, \ldots, K_n$ (group of internal images of the organ) in the respective folders $F_1, \ldots, F_n$. The folders $F_1, \ldots, F_n$ of the storage medium 214a have specification information (e.g. each patient number of the subjects $K_1, \ldots, K_n$) for the subjects $K_1, \ldots, K_n$ input from the specification information input unit 211c, as the respective folder names.

The control unit 215 controls the constituent units of the in-vivo information acquiring apparatus 210 that are the operating unit 211, the display unit 212, the receiving unit 213 and the storing unit 214. The control unit 215 controls input and output of the information between the constituent units. Specifically, the control unit 215 controls input of information from the operating unit 211, controls the information display process of the display unit 212, controls the image receiving process of the receiving unit 213, and controls the image storage process of the storage medium 214a. In this case, the control unit 215 controls to store, on the storage medium 214a separately for each subject, the series of internal images of the organ received by the receiving unit 213 during a period since an instruction is issued for starting storing the internal images of the organ until an instruction is issued for ending the storage. The control unit 215 controls to display, on the number display screen 212a, a patient number input from the specification information input unit 211c (i.e. a patient number of the examined subject $K_n$ to be laid on the bed 201 in order to store the group of internal images of the organ on the storage medium 214a). Furthermore, the control unit 215 associates the patient number of the subject $K_n$ to be displayed on the number display screen 212a with the series of internal images of the organ in this subject $K_n$ (the group of internal images of the organ imaged by the capsule endoscope in the examined region in this subject $K_n$). The control unit 215 controls to display, on the number display screen 212a, a sentence or the like for informing the completion of storage of the images for each patient number.

Such a control unit 215 has a receiving controller 215a, a storage controller 215b and a display controller 215c. The receiving controller 215a controls an image receiving process of the receiving unit 213. Specifically, the receiving controller 215a controls the receiving unit 213 to sequentially receive the internal images of the organ imaged by the capsule endoscope in the subject $K_n$ lying on the bed 201 during a period since the operating unit 211 instructs to start storing the internal images of the organ until it instructs to end storing the image.

More specifically, triggered by the start instruction information input from the operating unit 211 when the start button 211a is pressed, the receiving control unit 215a controls the receiving unit 213 to sequentially send the internal images of the organ received from the capsule endoscope in the subject $K_n$ to the control unit 215. Based on the control of the receiving controller 215a, the receiving unit 213 sequentially receives a wireless signal from the capsule endoscope in the subject $K_n$ through the receiving antennas A1 to A12. In addition, the receiving controller 215a acquires the internal images of the organ included in the received wireless signal. Furthermore, the receiving controller 215a sequentially sends the acquired internal images of the organ to the control unit 215. Triggered by the end instruction information input from the operating unit 211 when the end button 211b is pressed, the receiving controller 215a controls the receiving unit 213 to end receiving the internal images of the organ imaged by the capsule endoscope inside this subject $K_n$. The receiving unit 213 ends a process for extracting the internal images of the organ included in the wireless signal received from the capsule endoscope in this subject $K_n$, based on control of the receiving controller 215a.

The storage controller 215b controls the image storage process of the storing unit 214. Specifically, the storage controller 215b controls to store the group of internal images of the organ received by the receiving unit 213 on the storage medium 214a separately for each subject. In this case, the storage controller 215b controls to set, as a group of images, the series of internal images of the organ received by the receiving unit 213 during a period since the operating unit 211 instructs to start storing the internal images of the organ until operating unit 211 instructs to end storing the images, and controls to store the group of internal images of the organ on the storage medium 214a separately for each subject.

Furthermore, triggered by the start instruction information input from the operating unit 211 when the start button 211a is pressed, the storage controller 215b creates, on the storage medium 214a, a folder $F_n$ for holding and managing the group of internal images of the subject $K_n$ currently lying on the bed 201. The storage controller 215b controls the storing unit 214 to sequentially store the group of internal images of the organ sequentially input from the receiving unit 213 in this folder $F_n$. In this case, the storage controller 215b names the folder $F_n$ with the patient number input through the specification information input unit 211c. Accordingly, the storage controller 215b associates the patient number of this subject $K_n$ with the group of internal images of the organ in the folder $F_n$ (i.e. the series of internal images of the organ imaged by the capsule endoscope in the examined region in this subject $K_n$). After this, triggered by the end instruction information input from the operating unit 211 when the end button 211b is pressed, the storage controller 215b controls the storing unit 214 to end storing the group of internal images of the subject $K_n$ in the folder $F_n$. Triggered by the start instruction information and the end instruction information input repeatedly from the operating unit 211 every time the subjects $K_n$ to be laid on the bed 201 are switched, the storage controller 215b repeats the above controlling of the storing unit 214. As a result, the storage controller 215b stores each group of images of the subjects $K_1, K_2, \ldots, K_n$ (groups of internal images of organs) respectively in the folders $F_1, F_2, \ldots, F_n$ on the storage medium 214a.

The display controller 215c controls an information display process of the display unit 212. Specifically, the display controller 215c controls the display unit 212 to display, on the number display screen 212a, a patient number input from the specification information input unit 211c (i.e. a patient number of the subject $K_n$ to be laid on the bed 201 in order to acquire the group of internal images of the organ imaged by the capsule endoscope). Note that the subject $K_n$, having the patient number currently displayed on the number display screen 212a, is the current subject whose group of internal images of the organ should be stored in the folder $F_n$ on the storage medium 214a. The display controller 215c controls the display unit 212 to display a sentence or the like for informing the completion of storage of the images for each patient number.

Figure 11:
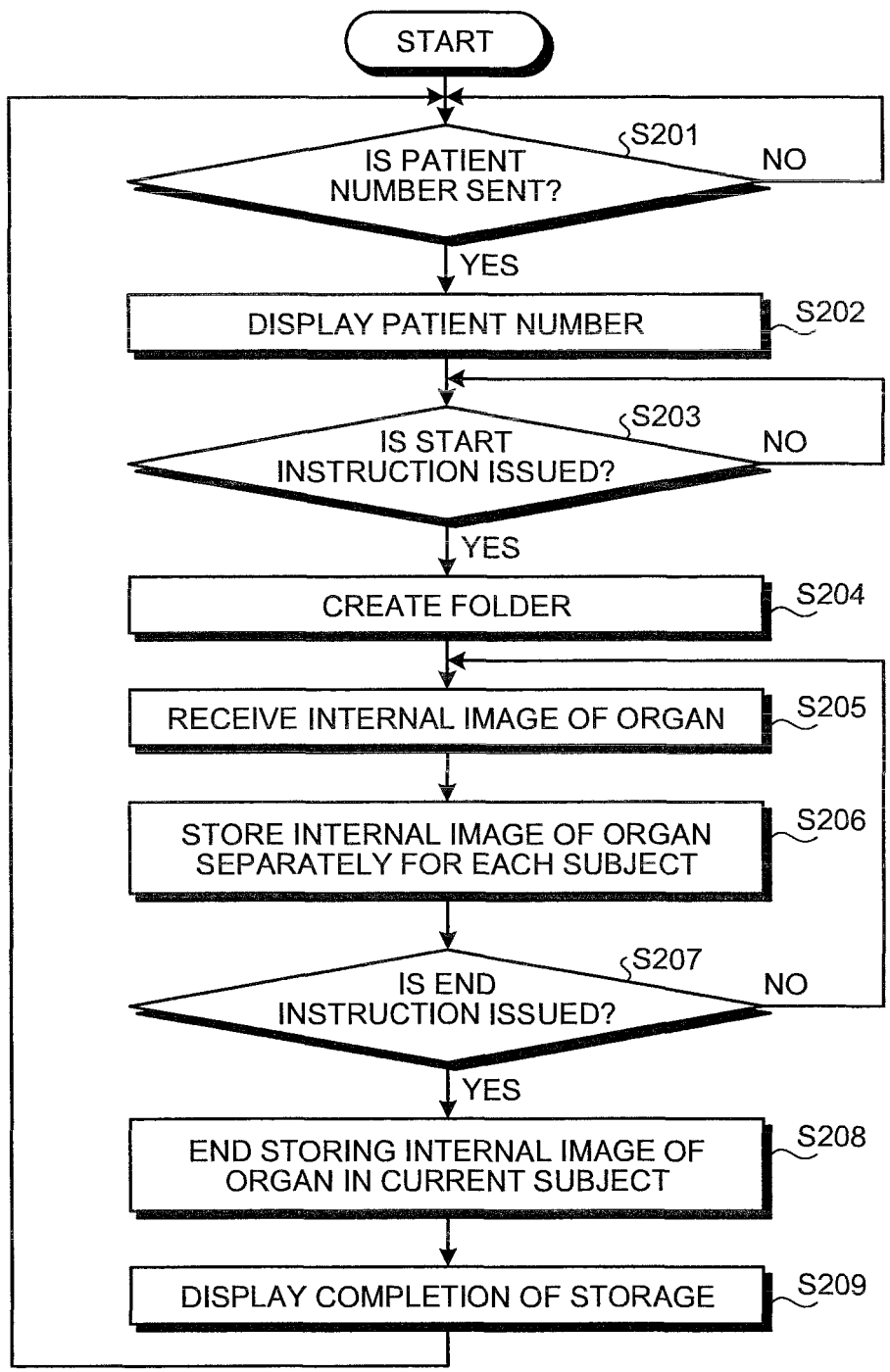
FIG. 11 is a flowchart exemplifying a process procedure of a control unit which controls storage of a group of internal images of an organ in a storage medium separately for each subject.

Next, a process procedure of the control unit 215 for carrying out a group medial examination using the in-vivo information acquiring apparatus 210 according to the second embodiment and for storing the groups of images of the plurality of subjects on the storage medium 214a separately for each subject is explained. FIG. 11 is a flowchart exemplifying the process procedure of the control unit 215 which controls to store the group of internal images of the organ on the storage medium 214a separately for each subject.

As shown in FIG. 11, the control unit 215 determines whether a patient number has been transmitted from the specification information input unit 211c (Step S201). Specifically, as described above, the operating unit 211 sends patient number information to the control unit 215 when input is made from the specification information input unit 211c. If the patient number information is not sent by the operating unit 211, the control unit 215 determines that there is no patient number information (Step S201, No), and repeats this step S201. In other words, the control unit 215 repeats this step S201 until the patient number information is input from the specification information input unit 211c.

When the patient number information is input and sent from the specification information input unit 211c, the control unit 215 determines that there is patient number information about this subject $K_n$ (Step S201, Yes). The control unit 215 controls the display unit 212 to display the patient number of the subject to be laid on the bed 201 (i.e. the subject to be supported by the subject support 201a) (Step S202). In this case, the display controller 215c controls the display unit 212 to display the patient number of the subject on the number display screen 212a. The patient number displayed on the number display screen 212a based on the control of the display controller 215c is for specifying the examined subject to be laid on the subject support 201a of the bed 201 in order to acquire the group of internal images of the organ imaged by the capsule endoscope.

After that, the control unit 215 determines whether there is an instruction for starting the image storage process for storing the internal images of the organ of the subject $K_n$ currently lying on the bed 201 (Step S203). Specifically, as described above, the operating unit 211 inputs the start instruction information in the control unit 215 when the start button 211a is pressed. The control unit 215 determines that there is no instruction for starting the image storage process about this subject $K_n$, unless the start instruction information is input through the operating unit 211 (Step S203, No), and repeats this step S203. In other words, the control unit 215 repeats this step S203 until the start instruction information is input through the operating unit 211.

When the start instruction information is input through the operating unit 211, the control unit 215 determines that there is an instruction for starting the image storage process about the subject $K_n$ (Step S203, Yes), and creates a folder for storing the group of internal images of the organ separately for each subject on the storage medium 214a (Step S204). Triggered by the start instruction information, the storage controller 215b creates a folder $F_n$ corresponding to the subject $K_n$ currently lying on the bed on the storage medium 214a. The storage controller 215b sets the patient number of the subject $K_n$ as a folder name of the folder $F_n$, and thus the patient number of the subject $K_n$ is associated with the folder $F_n$. In other words, the group of internal images of the organ stored in the folder $F_n$ is associated with the patient number of the subject $K_n$. Such a folder $F_n$ is for holding and managing the group of internal images of the organ of the subject $K_n$, and is easily identified by the patient number of the subject $K_n$ which is given as a folder name separately for each subject.

Subsequently, the control unit 215 controls the receiving unit 213 to receive the internal images of the organ imaged by the capsule endoscope in the subject $K_n$ currently lying on the bed (Step S205). Triggered by the above-described start instruction information, the receiving controller 215a controls the receiving unit 213 to acquire the internal images of the organ included in the wireless signal received from the capsule endoscope in the subject $K_n$. Furthermore, the receiving controller 215a controls the receiving unit 213 to send the internal images of the organ acquired based on the wireless signal to the control unit 215. Accordingly, the control unit 215 acquires the internal images of the subject $K_n$ received by the receiving unit 213 (the internal images of the organ imaged by the capsule endoscope).

Next, the control unit 215 controls the storing unit 214 to store the internal images of the organ received by the receiving unit 213 on the storage medium 214a separately for each subject (Step S206). In this case, the storage controller 215b controls the storing unit 214 to store the internal image of the organ acquired from the receiving unit 213 (i.e. the internal images of the subject currently lying on the bed) in the folder $F_n$ of the storage medium 214a. The storage controller 215b controls to store the internal images of the organ in the folder $F_n$ created separately for each subject, and thus can store the internal images of the organ of the subject $K_n$ on the storage medium 214a separately for each subject.

After that, the control unit 215 determines whether there is an instruction for ending the image storage process for storing the internal images of the organ in the subject $K_n$ currently lying on the bed 201 (Step S207). Specifically, as described above, the operating unit 211 inputs the end instruction information in the control unit 215 when the end button 211b is pressed. The control unit 215 determines that there is no instruction for ending the image storage process about the subject $K_n$ unless the end instruction information is input through the operating unit 211 (Step S207, No). The control unit 215 returns to the above-described step S205, and repeats the process procedure in and after this step S205. In other words, the control unit 215 sequentially repeats the process procedure from the above-described steps S205 to S207 during a period since the start instruction information is input through the operating unit 211 until the end instruction information is input. As a result, the group of internal images of the organ (i.e. the group of internal images of the organ of this subject $K_n$) received by the receiving unit 213 in the above period is stored in the folder $F_n$ of the storage medium 214a.

When the end instruction information is input through the operating unit 211, the control unit 215 determines that there is an instruction for ending the image storage process about the subject $K_n$ currently lying on the bed 201 (Step S207, Yes). The control unit 215 controls the storing unit 214 to end storing the internal image of the organ in the subject $K_n$ (current subject) (Step S208). In this case, triggered by the end instruction information, the storage controller 215b controls the storing unit 214 to end the image storage process to store the group of internal images of the organ about the subject $K_n$ as the current subject in the folder $F_n$ of the storage medium 214a. Furthermore, triggered by the end instruction information, the receiving controller 215a controls the receiving unit 213 to end the process for acquiring the internal images of the organ included in the wireless signal received from the capsule endoscope in the subject $K_n$.

Next, triggered by the end instruction information, the control unit 215 displays, on the number display screen 212a, contents of information representing the completion of storage of the images, in the form of a sentence or the like (Step S209). After that, the control unit 215 returns to the above-described step S201, and repeats the process procedure in and after this step S201.

This control unit 215 sequentially repeats the above-described process procedure from Step S201 to Step S209 every time the subjects $K_n$ (n=1, 2, 3, . . . ) to be laid on the bed 201 are switched sequentially. As a result, the control unit 215 can sequentially store each group of images of the plurality of subjects $K_1, K_2, \ldots, K_n$ for a group medical examination on the storage medium 214a separately for each subject. In this case, the storage medium 214a stores each group of images of the subjects $K_1, K_2, \ldots, K_n$ (group of internal images of the organ) in the respective folders $F_1, F_2, \ldots, F_n$ separately for each subject based on the control by the control unit 215.

Figure 12:
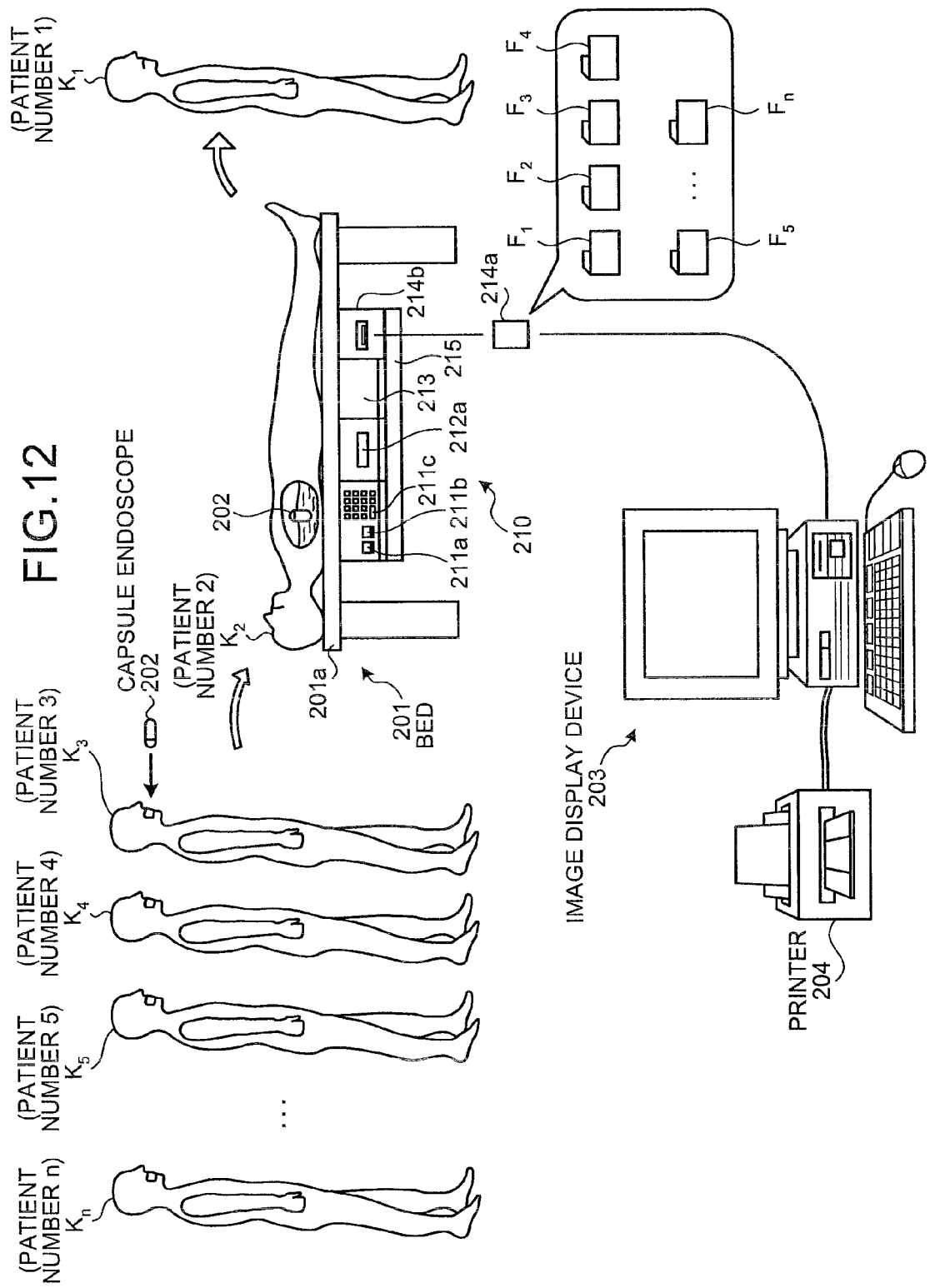
FIG. 12 is a schematic diagram exemplifying a state that a group medical examination is performed to acquire the group of internal images of the organ separately from each of a plurality of subjects, using the in-vivo information acquiring apparatus according to the second embodiment of the present invention.

Operations of the in-vivo information acquiring apparatus 210 according to the second embodiment are explained exemplifying a group medical examination in which the capsule endoscope is introduced into each of the n subjects $K_1$, $K_2, \ldots, K_n$ in order to acquire groups of internal images of the organ (e.g. the inside of a stomach) imaged by the capsule endoscope separately for each of a plurality of subjects. FIG. 12 is a schematic diagram exemplifying a state that a group medical examination is performed in order to acquire a group of internal images of the organ separately from each of a plurality of subjects, using the in-vivo information acquiring apparatus according to the second embodiment.

A predetermined preparation operation is performed for the in-vivo information acquiring apparatus 210. Specifically, after the power is turned on, the in-vivo information acquiring apparatus 210 is activated, and the storage medium 214a for storing the group of internal images of the organ separately for each subject is inserted into the storage unit 214b. Next, the control unit 215 controls the display unit 212 to display the patient number on the number display screen 212a when the patient number is input from the specification information input unit 211c.

As shown in FIG. 12, patient numbers 1, 2, . . . , n are given to "n" subjects $K_1, K_2, \ldots, K_n$ for a group medical examination in the order of lying on the bed 201. When the group of internal images of, for example, the stomach are imaged, the subjects $K_1, K_2, \ldots, K_n$ swallow the capsule endoscope 202 right before lying on the bed 201 or right after lying on the bed 201 to introduce the capsule endoscope 202 into the stomach. The subjects $K_1, K_2, \ldots, K_n$, who have introduced the capsule endoscope 202 into their stomach sequentially lie on the bed 201. In this case, each of the subjects $K_1, K_2, \ldots, K_n$ lies (is supported), for example, for the dozen or so minutes on the subject support 201a of this bed 201. The in-vivo information acquiring apparatus 210 acquires each group of images of the subjects $K_1, K_2, \ldots, K_n$ (group of internal images of the stomach) who sequentially lie on the bed 201 separately from each subject.

Specifically, when the patient number input from the specification information input unit 211c and displayed on the number display screen 212a is "1", the subject $K_1$ with a patient number "1" lies on the subject support 201a. The capsule endoscope 202 and a required amount of water are introduced into the stomach of the subject $K_1$ currently lying on the bed 201. In this state, the start button 211a and the end button 211b of the operating unit 211 are operated sequentially after a required period of time (e.g. the dozen or so minutes). In this case, the in-vivo information acquiring apparatus 210 stores, in the folder $F_1$ of the storage medium 214a, the group of internal images of the stomach imaged by the capsule endoscope 202 in the subject $K_1$.

Next, the control unit 215 controls the number display screen 212a to display contents for informing the completion of storage of the images in the folder $F_1$ in the form of a sentence or the like. After that, the control unit 215 controls the display unit 212 to display, on the number display screen 212a, the patient number input from the specification information input unit 211c (i.e. a patient number "2" of the subject to lie next on the bed 201). As a result, the number display screen 212a displays the patient number "2". Then, as shown in FIG. 12, the subject $K_2$ with the patient number "2" lies on the bed 201 in place of the subject $K_1$ who has lain on the bed 201 by this time. In this case, as in the case of the subject $K_1$, the capsule endoscope 202 and a required amount of water are introduced into the stomach of the subject $K_2$ currently lying on the bed 201 in place of the subject $K_1$.

The capsule endoscope 202 is an apparatus having an imaging function and a wireless communication function inside the capsule casing. The capsule endoscope has such a specific gravity that the capsule endoscope can float in the water (i.e. a specific gravity of 1 or lower). This capsule endoscope 202 floating in the water introduced into the stomach sequentially images the internal images of the stomach. The capsule endoscope 202 sequentially sends a wireless signal including the imaged internal images of inside of the stomach to the outside.

The start button 211a of the operating unit 211 is pressed, and the end button 211b of the operating unit 211 is pressed after the dozen or so minutes, in a state that the subject $K_2$ who has the stomach into which such a capsule endoscope 202 and a required amount of water are introduced is laid on the bed 201. For the dozen or so minutes since the start button 211a is pressed until the end button 211b is pressed, the in-vivo information acquiring apparatus 210 stores the group of internal images of the stomach imaged by the capsule endoscope 202 in this subject $K_2$ (i.e. the group of images of the examined region), in the folder $F_2$ of the storage medium 214a.

Specifically, triggered by the start instruction information input from the operating unit 211 when the start button 211a is pressed, the control unit 215 creates the folder $F_2$ corresponding to the subject $K_2$ currently lying on the bed 201, on the storage medium 214a. The control unit 215 sequentially stores the internal images of the stomach received by the receiving unit 213 (internal images of the subject $K_2$), in the folder $F_2$ of the storage medium 214a. In this case, the receiving unit 213 sequentially receives wireless signals from the capsule endoscope 202 in the subject $K_2$ through at least one of the receiving antennas A1 to A12 of the subject support 201a so as to sequentially acquire the internal images of the stomach included in the received wireless signals, for the dozen or so minutes since the start button 211a is pressed until the end button 211b is pressed. Then, the receiving unit 213 sequentially sends the acquired internal images of the stomach (internal images of the subject $K_2$) to the control unit 215.

While the dozen or so minutes elapse, the subject $K_2$ currently lying on the bed 201 changes its physical position as needed. As a result, the capsule endoscope 202 in the subject $K_2$ changes the imaging direction in the stomach so as to image the internal images of the entire stomach.

The control unit 215 sets a series of internal images of the stomach received by the receiving unit 213 during the dozen or so minutes, as a group of images. The control unit 215 controls the storing unit 214 to store the group of internal images of the stomach on the storage medium 214a separately for each subject. In this case, the storage medium 214a stores the group of internal images of the stomach in the subject $K_2$ in the folder $F_2$. The control unit 215 controls the display unit 212 to display, on the number display screen 212a, contents for informing the completion of storage of the images in the folder $F_2$ in the form of a sentence or the like. After that, the control unit 215 controls the display unit 212 to display the patient number input from the specification information input unit 211c (i.e. the patient number of the subject to be laid next on the bed 201) on the number display screen 212a.

Accordingly, the subjects $K_1, K_2, K_3, K_4, K_5, \ldots, K_n$ for a group medical examination sequentially lie on the bed 201 in accordance with the patient numbers input from the specification information input unit 211c and displayed on the number display screen 212a. As in the case of the above-described subject $K_2$, the in-vivo information acquiring 10 sequentially acquires the group of internal images of the stomach from the capsule endoscope 202 in the stomach of each of the subjects $K_1, K_2, K_3, K_4, K_5, \ldots, K_n$ who are sequentially laid on the bed 201, and stores the groups of acquired internal images of the stomach respectively in the folders $F_1, F_2, F_3, F_4, F_5, \ldots, F_n$.

After the group medical examination has been completed, as shown in FIG. 12, the storage medium 214a storing the group of internal images of the stomach of each of the subjects $K_1, K_2, K_3, K_4, K_5, \ldots, K_n$ respectively in the folders $F_1, F_2, F_3, F_4, F_5, \ldots, F_n$ is removed from the storage unit 214b, and inserted into the a predetermined image display device 203. As described above, the storage medium 214a is a portable medium, and can be easily carried after the stored medium 214a is removed from the storage unit 214b.

The image display device 203 has a configuration as a workstation or the like having a data management function to hold and manage the group of internal images of the organ imaged by the capsule endoscope 202 separately for each subject, and an image display function to display the group of internal images of the organ. The image display device 203 is separate from the in-vivo information acquiring apparatus 210, and is installed generally in hospitals.

This image display device 203 can read each group of images of the subjects $K_1, K_2, \ldots, K_n$ through the medium of this storage medium 214a when the above-described storage medium 214a is loaded into the image display device 203. The image display device 203 sequentially displays a group of desired internal images of an organ to be observed from the acquired groups of internal images of the organ of the subjects $K_1, K_2, \ldots, K_n$ on the display. The image display device 203 is connected to a printer 204 through a cable or the like, and thus the group of desired internal images of the organ to be observed can be sequentially printed out.

A user such as a doctor, or nurse views the internal images of the organ displayed on the image display device 203 or the internal images of the organ printed by the printer 204. Accordingly, the user observes (examines) the inside of the organ (e.g. the inside of the stomach) of the subjects $K_1, K_2, \ldots, K_n$ for a group medical examination. Based on the observation (examination), the user can diagnose the subjects $K_1, K_2, \ldots, K_n$ for the group medical examination.

As described above, the in-vivo information acquiring apparatus 210 according to the second embodiment of the present invention is configured to include the operating unit 211, the display unit 212, the receiving unit 213, the storing unit 214 and the control unit 215 attached, for example, onto the bed 201. Thus, the in-vivo information acquiring apparatus 210 can receive the groups of internal images of the organ of the plurality of subjects $K_1, K_2, \ldots, K_n$ separately from each subject and can store the received groups of images of the organ on the storage medium 214a separately for each subject even without using a workstation or the like that can perform collective data management of the group of internal images of the plurality of subjects exemplarily shown on the above-described image display device 203. As a result, it is possible to miniaturize the size of the device having a function for acquiring the groups of internal images of the organ in the plurality of subjects $K_1, K_2, \ldots, K_n$ separately from each subject.

The in-vivo information acquiring apparatus 210 is integrated with the bed 201 which sequentially supports, for example, a plurality of subjects. Thus, it can be easily conveyed to a desired place such as the inside of a medical checkup vehicle for performing the above-described group medical examination.

Furthermore, the in-vivo information acquiring apparatus 210 stores the group of images (the group of internal images of the organ) of each of the plurality of subjects $K_1, K_2, \ldots, K_n$ respectively in the folders $F_1, F_2, \ldots, F_n$ of the storage medium 214a detachably inserted into the storage unit 214b. As a result, it is possible to easily store the groups of internal images of the organ in the plurality of subjects $K_1, K_2, \ldots, K_n$ acquired by the above-described group medical examination, separately for each subject, and it is also possible to perform data management for the groups of internal images of the plurality of subjects separately for each subject.

The storage medium 214a is a portable recording medium which can be detachably inserted into the storage unit 214b. Thus, it is possible to easily carry the groups of images of the plurality of subjects acquired by the above-described group medical examination, and it is also possible to easily read the groups of internal images of the plurality of subjects into the workstation such as the image display device 203.

The plurality of receiving antennas A1 to A12 are attached onto the subject support 201a in a state that the receiving antennas A1 to A12 are fixed and arranged near the examined region in the subject supported by the subject support 201a of the bed 201. The plurality of subjects are sequentially laid on the subject support 201a of the bed 201 on which the receiving antennas A1 to A12 are thus attached thereonto. In this manner, it is possible to sequentially receive the group of internal images of the subject through the receiving antennas A1 to A12 attached onto the subject support 201a, even without attaching the plurality of receiving antennas onto the body surface of each subject. In addition to this, there is no need to attach a predetermined receiving device on each subject. As a result, the above-described group medical examination can be smoothly performed, and it saves labor hour required for acquiring the group of internal images of the plurality of subjects by the group medical examination, as compared to the conventional receiving device which sequentially receives the group of images from the capsule endoscope through a plurality of receiving antennas attached onto a plurality of parts on the body surface of the subjects.

As described above, according to the configuration of the second embodiment of the present invention, one or more receiving antenna is attached onto the subject support of the bed which supports the subject having the organ into which the capsule endoscope has been introduced. This receiving antenna is fixed and arranged near the examined region in the subject supported by this subject support. Furthermore, the group of internal images of the organ is sequentially received through the receiving antenna of the subject support separately for each subject from the capsule endoscope inside the subject lying on the bed. The configuration has the operating unit for operating to start and end storing the internal images of the subject currently lying on the bed. The configuration stores the series of internal images of the organ received during a period since the operating unit instructs to start storing the internal images of the organ until the operating unit instructs to end the storage from the capsule endoscope in the subject through the receiving antenna of the subject support, separately for each subject on the storage medium. Thus, the group of internal images of the plurality of subjects can be sequentially received separately from each subject, by sequentially lying (supporting) the plurality of subjects on the subject support of the bed with the receiving antenna attached thereon even without attaching the receiving antenna on the body surface of each of the plurality of subjects and without mounting a predetermined receiving device on each of the plurality of subjects. As a result, it is possible to realize the in-vivo information acquiring apparatus, which can save labor hour required for an operation for attaching the receiving antenna onto each subject and an operation for mounting the receiving device, can easily acquire the internal images of the organ from the capsule endoscope introduced into the organ of the subject, and can easily carry out a group medical examination for sequentially acquiring the group of internal images of the organ in the plurality of subjects separately from each subject.

The group of internal images of the plurality of subjects are stored on the storage medium separately for each subject. Thus, the group of internal images of the organ can be easily stored on a small number of storage medium (media) (e.g. may be a single storage medium), as compared to the conventional technique in which each subject portably carry the receiving device. In addition, it is possible to easily perform data management for the group of internal images of the plurality of subjects acquired by the above-described group medical examination separately for each subject.

Furthermore, according to the configuration, a storage medium storing the group of internal images of the organ separately for each subject is portable, and the portable recording medium is detachably inserted into the in-vivo information acquiring apparatus according to the present invention. As a result, the group of internal images of the plurality of subjects acquired by the above-described group medical examination can be easily carried, and the group of internal images of the plurality of subjects can be easily read into a predetermined image display device.

Third Embodiment

A third embodiment of the present invention is explained. According to the second embodiment, the patient numbers of the subjects to be sequentially laid on the bed 201 are sequentially displayed on the number display screen 212a. However, in the third embodiment, the internal images of the organ received from the capsule endoscope in the subject currently lying on the bed 201 are further displayed.

Figure 13:
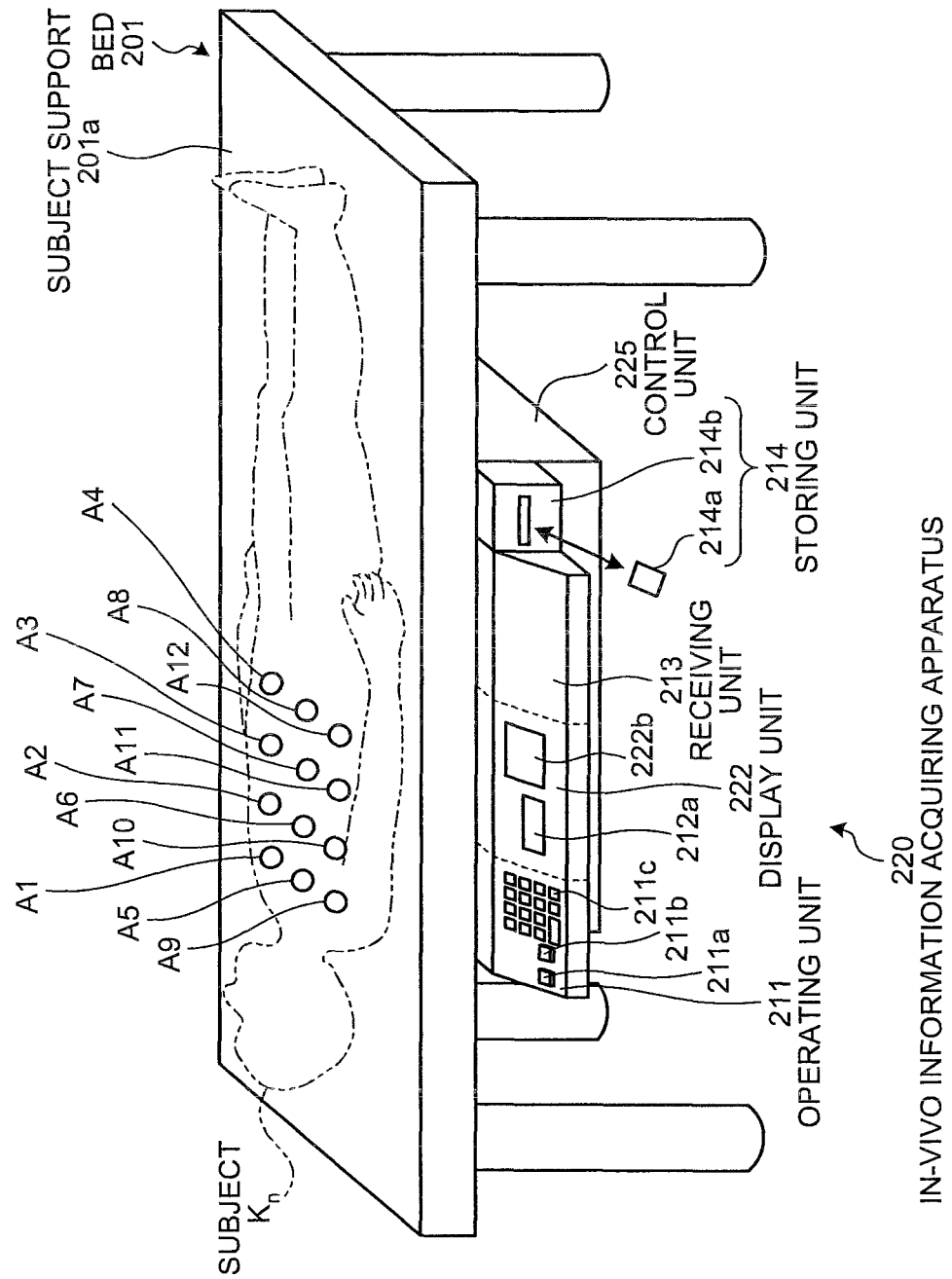
FIG. 13 is an external appearance schematic diagram showing a configuration example of an in-vivo information acquiring apparatus according to a third embodiment of the present invention.
Figure 14:
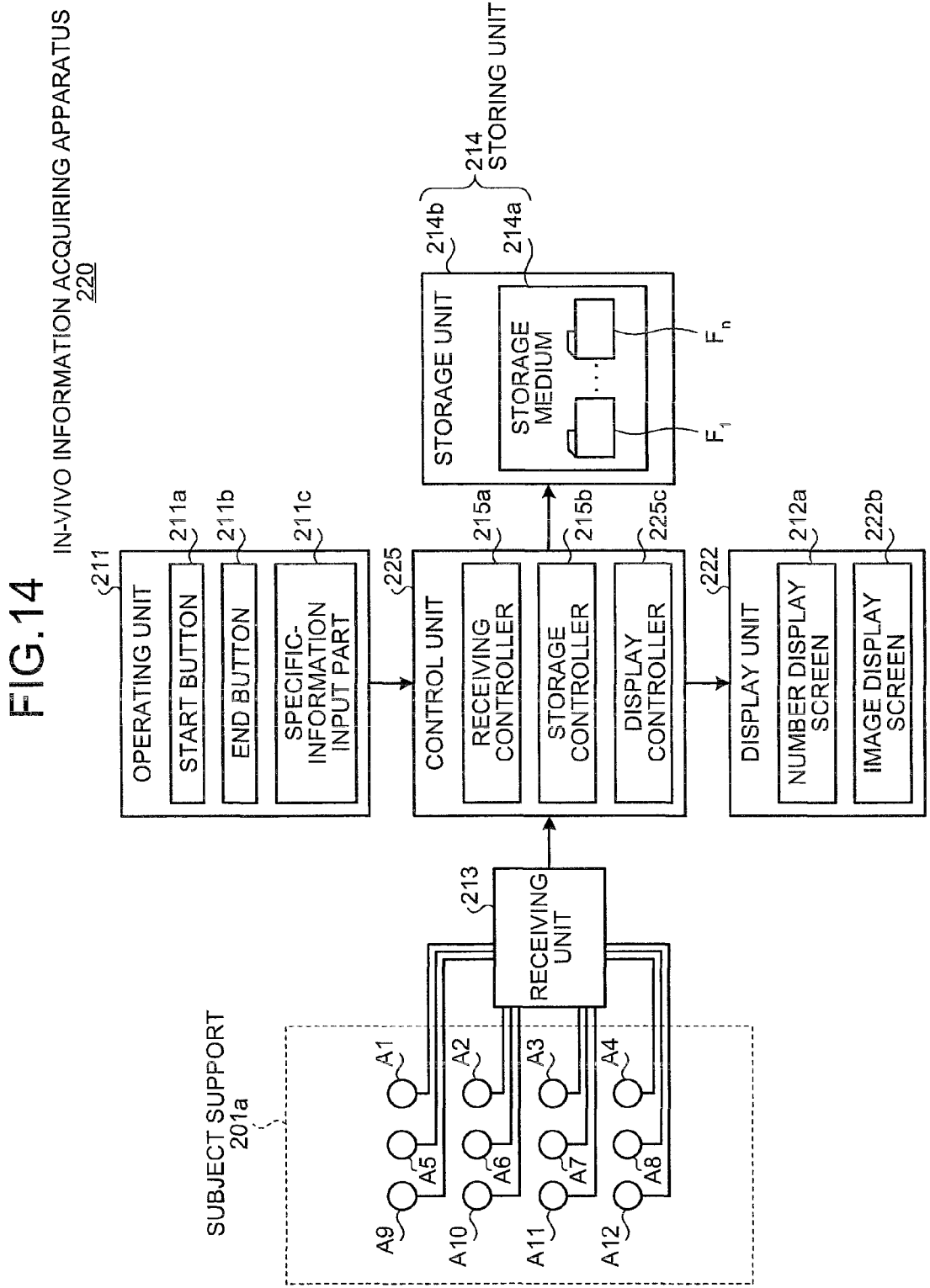
FIG. 14 is a block diagram showing an example of a function configuration of the in-vivo information acquiring apparatus according to the third embodiment of the present invention.

FIG. 13 is an external appearance schematic diagram showing a configuration example of an in-vivo information acquiring apparatus according to the third embodiment of the present invention. FIG. 14 is a block diagram showing an example of a function configuration of the in-vivo information acquiring apparatus according to the third embodiment of the present invention. As shown in FIGS. 13 and 14, an in-vivo information acquiring apparatus 220 according to the third embodiment has a display unit 222 in place of the display unit 212 of the above-described in-vivo information acquiring apparatus according to the second embodiment, and also a control unit 225 in place of the control unit 215. Any other configuration is the same as that of the second embodiment, and the same reference numeral is given to the same configuration unit.

The display unit 222 has the above-described number display screen 212a, and displays, on the number display screen 212a, a patient number input from the specification information input unit 211c (i.e. a patient number of an examined subject $K_n$ to be laid on the bed 201 in order to acquire the internal images of the organ from the capsule endoscope introduced into the organ). In addition to this, the display unit 222 has an image display screen 222b for displaying the internal images of the organ imaged by the capsule endoscope in the subject $K_n$. This display unit 222 sequentially displays the patient numbers on the number display screen 212a, like the display unit 212 of the above-described in-vivo information acquiring apparatus 210 according the second embodiment. The display unit 222 sequentially displays, on the image display screen 222b, the internal images of the organ received by the receiving unit 213 from the capsule endoscope in the subject $K_n$ currently lying on the bed 201. In other words, such an image display screen 222b functions as an image display unit for sequentially displaying the internal images of the organ received by the above-described receiving unit 213.

The control unit 225 controls constituent units of the in-vivo information acquiring apparatus 220 that are the operating unit 211, the display unit 222, the receiving unit 213 and the storing unit 214. The control unit 215 controls input and output of the information between the constituent units. Specifically, like the control unit 215 of the above-described in-vivo information acquiring apparatus 210 according to the second embodiment, the control unit 225 controls input of information from the operating unit 211, controls a process for displaying the patient number displayed on the number display screen 212a of the display unit 222, controls an image receiving process of the receiving unit 213, and controls an image storage process of the storage medium 214a. In this case, like the above-described control unit 215, the control unit 225 controls to store the group of received internal images of the organ received by the receiving unit 213 on the storage medium 214a separately for each subject. The control unit 225 controls to display the patient number input from the specification information input unit 211c on the number display screen 212a. The control unit 225 controls to sequentially display the internal images of the organ imaged by the capsule endoscope in the subject $K_n$ currently lying on the bed 201 on the image display screen 222b.

This control unit 225 has the above-described receiving controller 215a and the storage controller 215b, and has a display controller 225c in place of the display controller 215c of the control unit 215 of the in-vivo information acquiring apparatus 210 according to the second embodiment. The display controller 225c controls the information displaying process of the display unit 222. Specifically, like the display controller 215c of the above-described in-vivo information acquiring apparatus 210 according to the second embodiment, the display controller 225c controls the display unit 222 to display the patient number input from the specification information input unit 211c (i.e. the patient number of the subject $K_n$ to be laid on the bed 201) on the number display screen 212a. Furthermore, the display controller 225c controls the display unit 222 to display the internal images of the organ of the subject $K_n$ currently lying on the bed 201, on the image display screen 222b. In this case, the display controller 225c controls the display unit 222 to display, on the image display screen 222b, the internal images of the organ received sequentially by the receiving unit 213 from the capsule endoscope in the subject $K_n$ currently lying on the bed 201.

Figure 15:
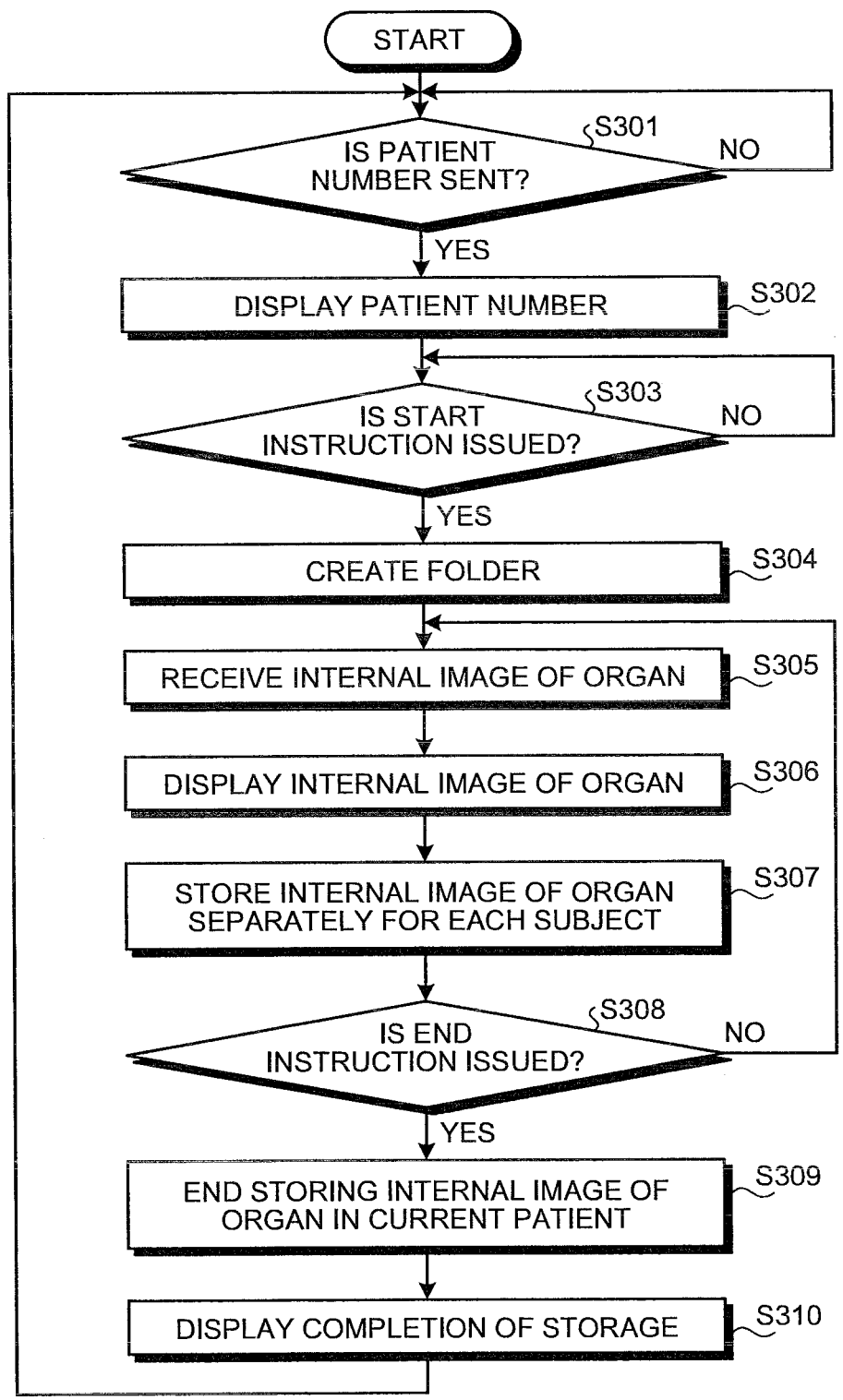
FIG. 15 is a flowchart exemplifying a process procedure of a control unit which controls display of an internal image of an organ on an image display screen and also storage of a group of internal images of an organ separately for each subject.

A process procedure of the control unit 225 for storing the groups of internal images of a plurality of subjects on the storage medium 214a separately for each subject by performing a group medical examination using the in-vivo information acquiring apparatus 220 according to the third embodiment is explained. FIG. 15 is a flowchart exemplifying the process procedure of the control unit 225 which controls to display the internal images of the organ on the image display screen 222b and which controls to store the groups of internal images of the organ on the storage medium 214a separately for each subject.

Almost like the control unit 215 of the above-described in-vivo information acquiring apparatus 210 according to the second embodiment, the control unit 225 controls to sequentially display, on the number display screen 212a, the patient numbers input from the specification information input unit 211c. In addition, the control unit 225 controls to store, on the storage medium 214a, the groups of internal images of the organ received by the receiving unit 213 during a period since the operating unit 211 instructs to start storing the internal images of the organ until the operating unit 211 instructs to end storing the images. In this case, the control unit 225 further controls to sequentially display the internal images of the organ received by the above-described receiving unit 213 on the image display screen 222b.

Specifically, as shown in FIG. 15, the control unit 225 determines whether the specification information input unit 211c has sent the patient number as in the above-described steps S201 to S205 (Step S301). When the patient number information is input and sent from the specification information input unit 211c, the control unit 225 controls the number display screen 212a to display the patient number (Step S302), and determines whether there is an instruction for starting the image storage process (Step S303). When there is a start instruction, the control unit 225 creates the folders $F_n$ on the storage medium 214a separately for each subject (Step S304), and controls the receiving unit 213 to receive the internal images of the organ of the subject $K_n$ currently lying on the bed 201 (Step S305). In this case, the control unit 225 acquires the internal images of the organ received by the receiving unit 213, like the control unit 215 of the above-described in-vivo information acquiring apparatus 210 according to the second embodiment.

Next, the control unit 225 then controls to display, on the image display screen 222b, the internal images of the organ received by the receiving unit 213 from the capsule endoscope in the subject $K_n$ currently lying on the bed 201 (Step S306). In this case, the display controller 225c controls the display unit 222 to display the internal images of the organ received by the receiving unit 213 on the image display screen 222b.

Based on the control of the display controller 225c, the display unit 222 displays the patient number on the number display screen 212a, and displays, on the image display screen 222b, the internal images of the organ received by the receiving unit 213 (i.e. the internal images of the organ imaged by the capsule endoscope in the subject currently lying on the bed 201).

After that, as in the above-described steps S206 to S209, the control unit 225 controls to store the internal images of the organ received by the receiving unit 213 on the storage medium 214a separately for each subject (Step S307). The control unit 225 determines whether there is an instruction for ending the image storage process (Step S308). When there is this end instruction, the control unit 225 controls the storing unit 214 to end storing the internal images of the organ in the current subject (Step S309), and displays the contents for informing the completion of storage of the images in the form of a sentence or the like on the number display screen 212a (Step S310).

When it is determined that there is no instruction for ending the image display process in Step S308, the control unit 225 returns to the above-described step S305 so as to repeat a process procedure in and after this step S305. In other words, the control unit 225 sequentially repeats the above-described process procedure of S305 to S308 during a period since the operating unit 211 inputs start instruction information until the operating unit 211 inputs end instruction information. As a result, the image display screen 222b sequentially displays the series of internal images of the organ received by the receiving unit 213 in the above period. The group of internal images of the organ received by the receiving unit 213 in the period are stored in the folders $F_n$ of the storage medium 214a (i.e. the group of internal images of the organ in the subject $K_n$ currently lying on the bed 201).

After the contents for informing the completion of storage of the images by performing the process procedure of step S310 are displayed on the number display screen 212a in the form of a sentence or the like, the control unit 225 returns to the above-described step S301 and repeats the process procedure in and after this step S301. This control unit 225 sequentially repeats the process procedures of the above-described steps S301 to S310 every time the subjects $K_n$ (n=1, 2, 3, . . . ) to be laid on the bed 201 are sequentially switched one after another. As a result, like the control unit 215 of the above-described in-vivo information acquiring apparatus 210 according to the second embodiment, the control unit 225 can sequentially store each group of images of the plurality of subjects $K_1, K_2, \ldots, K_n$ (group of internal images of the organ) for a group medical examination, respectively in the folders $F_1, F_2, \ldots, F_n$ separately for each subject.

Figure 16:
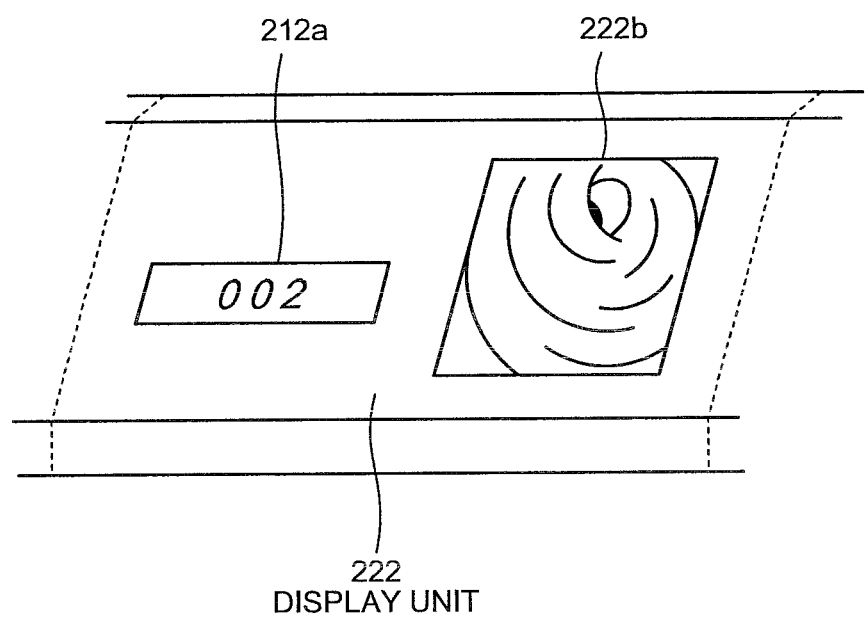
FIG. 16 is a schematic diagram exemplifying a state of a display unit which displays a patient number of a current subject on a number display screen and displays an internal image of an organ of the current subject on the image display screen.

Next, operations of the in-vivo information acquiring apparatus 220 according to the third embodiment are explained exemplifying a case in which a group medical examination is performed the capsule endoscope is introduced into each of the n subjects $K_1, K_2, \ldots, K_n$, and acquiring the groups of internal images of the organ (e.g. the inside of stomach) imaged by the capsule endoscope separately for each of a plurality of subjects. FIG. 16 is a schematic diagram exemplifying a state of the display unit 222 which displays a patient number of the current subject on the number display screen 212a and displays the internal image of the organ of the current subject on the image display screen 222b.

Almost like the above-described state shown in FIG. 12, the plurality of subjects $K_1, K_2, \ldots, K_n$ for a group medical examination sequentially lie on the bed 201 in accordance with patient numbers input from the specification information input unit 211c and displayed on the number display screen 212a. The capsule endoscope 202 and a required amount of water are introduced into the stomach of each of the subjects $K_1, K_2, \ldots, K_n$ lying on this bed 201. Almost like the above-described in-vivo information acquiring apparatus 210 according to the second embodiment, the in-vivo information acquiring apparatus 220 sequentially acquires the group of internal images of the stomach from the capsule endoscope 202 inside the stomach of each of the subjects $K_1, K_2, \ldots, K_n$ who are sequentially laid on the bed 201. In addition, the in-vivo information acquiring apparatus 220 stores the acquired group of internal images of the stomach respectively in the folders $F_1, F_2, \ldots, F_n$ separately for each subject. In this case, the in-vivo information acquiring apparatus 220 sequentially receives, by the receiving unit 213, the internal images of the stomach imaged by the capsule endoscope 202 introduced into the current subject (into the subject having a patient number currently displayed on the number display screen 212a) currently lying on the bed 201. The in-vivo information acquiring apparatus 220 sequentially displays the internal images of the stomach received by the receiving unit 213 on the image display screen 222b.

Specifically, among the plurality of subjects $K_1, K_2, \ldots, K_n$ for a group medical examination, when the subject $K_2$ having a patient number "2" currently lies on the bed 201, the in-vivo information acquiring apparatus 220 displays the patient number and the internal images of the stomach of the subject $K_2$ as the current subject on the display unit 222. In other words, the control unit 225 controls the display unit 222 to display the patient number of this subject $K_2$, and to sequentially display the internal images of the stomach received by the receiving unit 213 from the capsule endoscope 202 in this subject $K_2$. As shown in FIG. 16, based on the control of the control unit 225, the display unit 222 displays the patient number "2" of this subject $K_2$ on the number display screen 212a, and displays also the internal images of the stomach of this subject $K_2$ on the image display screen 222b. When the receiving unit 213 receives the internal images of the stomach imaged by the capsule endoscope 202 in this subject $K_2$, the display unit 222 sequentially displays the internal images of the stomach of the subject $K_2$ received by the receiving unit 213 on the image display screen 222b.

After this group medical examination has been completed, the storage medium 214a storing the group of internal images of the stomach of each of the subjects $K_1, K_2, \ldots, K_n$ in the folders $F_1, F_2, \ldots, F_n$ is removed from the storing unit 214 and inserted into the image display device 203, as shown in FIG. 12. The image display device 203, into which the storage medium 214a is inserted, reads each group of images of the subjects $K_1, K_2, \ldots, K_n$ (group of internal images of the organ) through the storage medium 214a. The image display device 203 displays a group of internal images of a desired organ to be observed sequentially on the display, of the acquired groups of internal images of the organ of the subjects $K_1, K_2, \ldots, K_n$. The image display device 203 prints out the group of internal images of the desired organ to be observed with the printer 204 as needed.

As in the second embodiment, a user (such as doctor, or nurse) views the internal images of the organ displayed on the image display device 203 or the internal images of the organ printed by the printer 204. Accordingly, the user observes (examines) the inside of the organ (e.g. the inside of the stomach) of the subjects $K_1, K_2, \ldots, K_n$ for a group medical examination. Based on the observation (examination), the user can diagnose the subjects $K_1, K_2, \ldots, K_n$ for the group medical examination.

As described above, the in-vivo information acquiring apparatus 220 according to the third embodiment of the present invention is configured to include the operating unit 211, the display unit 222, the receiving unit 213, the storing unit 214 and the control unit 225 attached, for example, onto the bed 201. Thus, as in the case of the above-described in-vivo information acquiring apparatus 210 according to the second embodiment, the in-vivo information acquiring apparatus 220 can receive the groups of internal images of the organ of the plurality of subjects $K_1, K_2, \ldots, K_n$ separately from each subject, and can store the received groups of images of the organ separately for each subject on the storage medium 214a even without using a workstation that can perform collective data management for the groups of internal images of the plurality of subjects exemplarily shown on the above-described image display device 203. As a result, it is possible to miniaturize the size of the device having a function for acquiring the groups of internal images of the organ in the plurality of subjects $K_1, K_2, \ldots, K_n$ separately from each subject.

The in-vivo information acquiring apparatus 220 is integrated with the bed 201 which sequentially supports, for example, a plurality of subjects. Thus, as in the case of the in-vivo information acquiring apparatus 210 according to the second embodiment, the in-vivo information acquiring apparatus 220 can be easily conveyed to a desired place such as the inside of a medical checkup vehicle for performing the above-described group medical examination.

Furthermore, the in-vivo information acquiring apparatus 220 sequentially displays the internal images of the organ imaged by the capsule endoscope in the current subject currently lying on the bed 201 on the image display screen 222b. Thus, it is possible to easily know the region into which the capsule endoscope is introduced (i.e. the current position of the capsule endoscope) in this current subject by viewing the internal images of the organ sequentially displayed on the image display screen 222b. As a result, it is possible to easily check whether the capsule endoscope is introduced into a desired examined region (stomach, alimentary tract including the small intestine or the like) in the current subject, and it is also possible to surely acquire the group of images of the desired examined region imaged by the capsule endoscope.

As described above, the third embodiment of the present invention has the same configuration as that of the second embodiment, and is further configured to have the image display screen for sequentially displaying the internal image of the subject received by the receiving unit, and configured to sequentially display the internal images of the organ imaged by the capsule endoscope in the subject in a state that the subject is supported by the bed on the image display screen. Thus, in addition to the operating effect of the second embodiment, it is possible to easily know the current position of the capsule endoscope in this subject by viewing the internal images of the organ sequentially displayed on the image display screen. This results in realizing an in-vivo information acquiring apparatus which provides the operating effect of the second embodiment, and which enables to easily check whether the capsule endoscope is introduced into the desired examined region inside the subject, and which also enables to surely acquire the group of internal images of the desired examined region imaged by the capsule endoscope.

In the second and third embodiments of the present invention, the in-vivo information acquiring apparatus integrated with the bed sequentially supporting the subjects on the subject support onto which the plurality of receiving antennas are attached is exemplified. However, the configuration is not limited to this, and may be an in-vivo information acquiring apparatus integrated with a supporting member, which supports a subject having an organ into which the capsule endoscope is introduced, and has one or more receiving antenna fixed and arranged near the examined region in the subject.

Specifically, the supporting member integrated with the in-vivo information acquiring apparatus according to the present invention may be an equipment which stands upright in a state that the equipment is supported by a predetermined stand, strut or the like, supports the subjects upright, and fixes and arranges one or more receiving antenna near the examined region in the supported subject. In this case, the upright type supporting member supports the subjects in a state that the upright type supporting member is held and kept by the subject. One or more receiving antenna is attached, for example, in a grid pattern, onto the subject support of the upright type supporting member. The height of the supporting member, onto which the receiving antenna is attached, with respect to the subject may be adjusted so that the position of the receiving antenna can be adjusted in accordance with the desired examined region (such as the stomach, small intestine or the like) in the subject.

In the second and third embodiments of the present invention, the groups of internal images of the plurality of subjects are stored on the portable recording medium 214a which is detachably inserted in the storage unit 214b. However, the configuration is not limited to this. There may be provided a storing device having a semiconductor memory (flash memory or the like) or hard disk in place of the storing unit 214, thereby storing the group of internal images of the plurality of subjects separately for each subject in the storage device. In this case, the storage device may be detachable from the in-vivo information acquiring apparatus according to the present invention, and the storage device removed from the in-vivo information acquiring apparatus may be connected to a predetermined workstation (e.g. the image display device 203) so as to make the groups of internal images of the plurality of subjects read into this workstation. The storage device may be integrated with the in-vivo information acquiring apparatus according to the present invention, and the storage device may be connected to a workstation (e.g. the image display device 203) with a cable or the like so as to make the groups of internal images of the plurality of subjects read into this workstation.

Furthermore, in the second and third embodiments of the present invention, the patient numbers are exemplified as specification information for specifying each of the plurality of subjects. However, the specification information is not limited to the patient numbers. The specification information may be any information for making it possible to specify each of the plurality of examined subjects, may be ID information given to each of the plurality of subjects (information formed with at least one of a letter, a numeral and a mark), or may be a patient name of each of the subjects, for example. In this case, the display unit of the in-vivo information acquiring apparatus may sequentially display any specification information such as a patient ID or patient name in place of the patient information.

In the second and third embodiments of the present invention, the receiving antennas A1 to A12 are attached onto the subject support 201a of the bed 201 supporting the subject $K_n$ having an organ into which the capsule endoscope is introduced. However, the configuration is not limited to this. One or more receiving antenna may be attached onto a sheet unfolded on the subject support 201a of the bed 201, this sheet is unfolded on the subject support 201a corresponding to the desired examined region in the subject $K_n$, and thus the one or more receiving antenna attached onto the sheet is fixed and arranged near the examined region in the subject.

Figure 17:
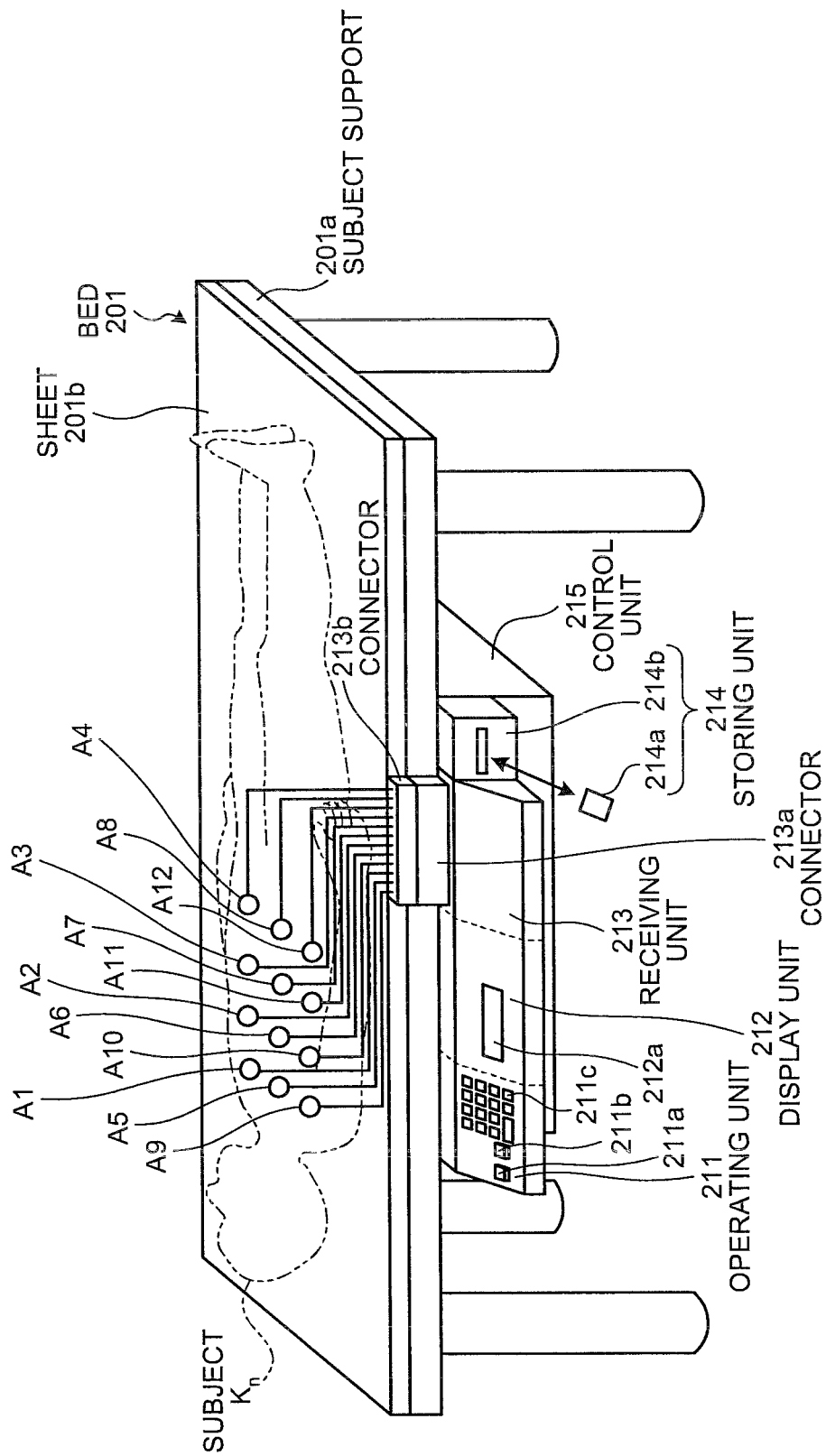
FIG. 17 is an external appearance schematic diagram showing a modification of an in-vivo information acquiring apparatus according to the present invention.

Specifically, as shown in FIG. 17, the receiving antennas A1 to A12 may be attached to the sheet 201b unfolded on the subject support 201a of the bed 201, and the receiving antennas A1 to A12 attached onto the sheet 201b may be fixed and arranged near the examined region in the subject $K_n$. In this case, a connector 213b connected to the receiving antennas A1 to A12 is provided on the sheet 201b, and a connector 213a connected to the connector 213b is provided on the receiving unit 213. The receiving unit 213 is connected to the receiving antennas A1 to A12 through the connectors 213a and 213b and a cable or the like, and receives the group of internal images of the subject $K_n$ through the receiving antennas A1 to A12. Such a sheet 201b can change the position relative to the subject support 201a of the bed 201. Thus, the receiving antennas A1 to A12 of the sheet 201b can be freely fixed and arranged near a desired examined region inside the subject by unfolding the sheet 201b in a position above the subject support 201a corresponding to the desired examined region in the subject supported by the subject support 201a.

In the second and third embodiments of the present invention, the control units 215 and 225 control the number display screen 212a to display the patient number input from the specification information input unit 211c (i.e. the patient number of the examined subject $K_n$ to be laid on the subject support 201a of the bed 201). Also, the control units 215 and 225 name the folder $F_n$ with the displayed number. However, the configuration is not limited to this. For example, the control units 215 and 225 may automatically update the patient number, and may display the updated patient number on the number display screen 212a as a patient number so as to set the number as a folder name of the folder $F_n$.

Specifically, after the in-vivo information acquiring apparatuses 210 and 220 are activated for example by turning on the power, the control units 215 and 225 initialize the patient number to, for example, "1", the patient number specifying the examined subject to be laid on the subject support 201a of the bed 201 in order to acquire the group of internal images of the organ imaged by the capsule endoscope. Then, the in-vivo information acquiring apparatuses 210 and 220 display the patient number on the number display screen 212a, and stores the images using the current patient number of the subject $K_1$ currently lying on the bed 201, that is, the patient number currently displayed on the number display screen 212a, as a folder name. Triggered by the end instruction information for ending storage of the images, the in-vivo information acquiring apparatuses 210 and 220 update the patient number by adding a predetermined value (for example +1) to the patient number. In this manner, the updated patient number may be a patient number for specifying a subject $K_n$ to be laid on the bed 201 next to the current subject (i.e. a subject whose group of internal images of the organ to be stored on the storage medium 214a next to the current subject). The number may be a folder name of the folder $F_n$.

Fourth Embodiment

Figure 18:
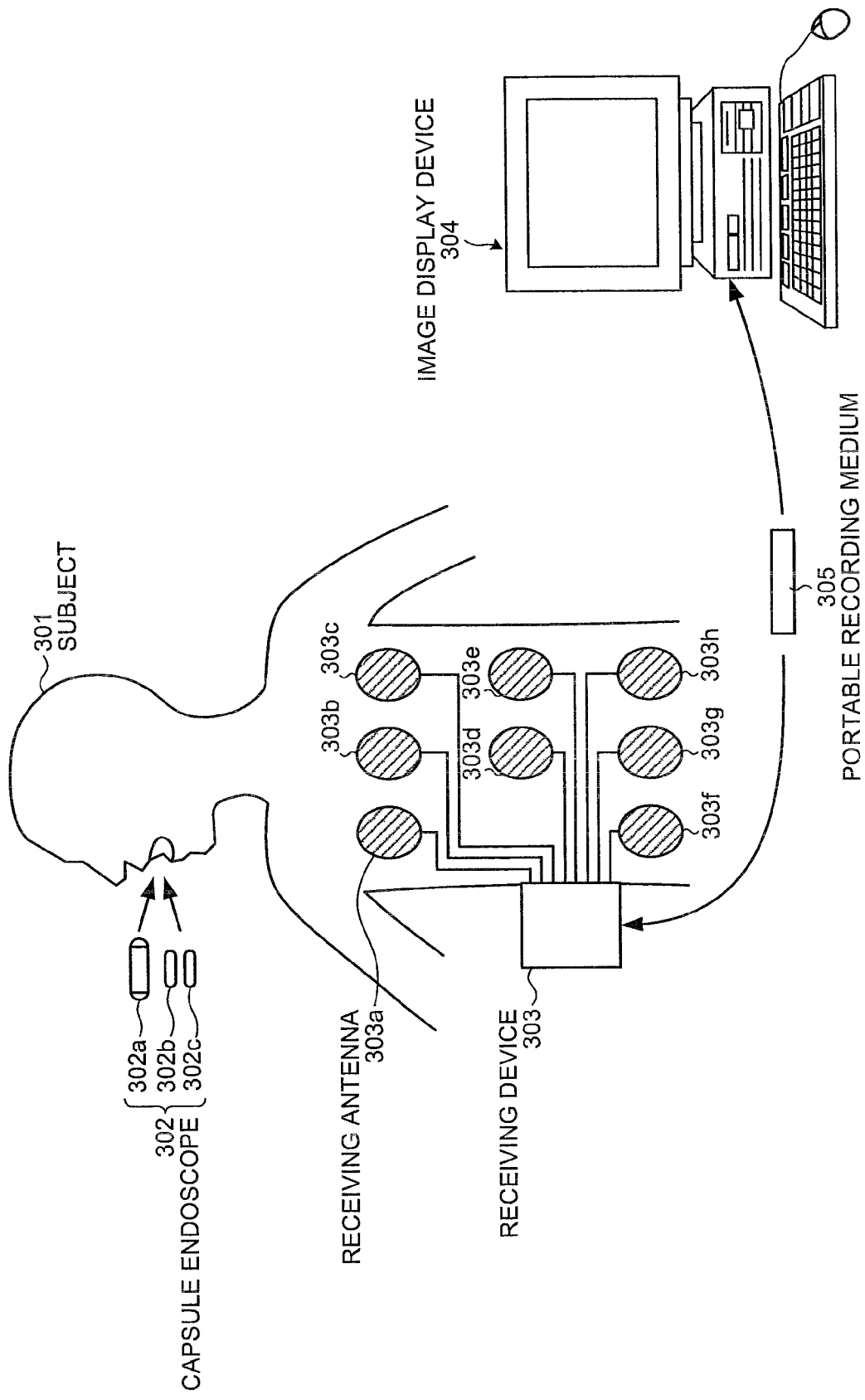
FIG. 18 is a schematic diagram showing one configuration example of an in-vivo information acquiring system having a capsule endoscope according to a fourth embodiment of the present invention.

FIG. 18 is a schematic diagram showing a configuration example of an in-vivo information acquiring system having a capsule endoscope according to a fourth embodiment of the present invention. As shown in FIG. 18, the in-vivo information acquiring system includes a capsule endoscope 302 that images the internal images of a subject 301; a receiving device 303 that receives internal images of the subject 301 imaged by the capsule endoscope 302; an image display device 304 that displays the internal images of the subject 301 received by the receiving device 303; and a portable recording medium 305 for transferring data between the receiving device 303 and the image display device 304.

The capsule endoscope 302 according to the fourth embodiment floating in liquid introduced into the organ of the subject 301 images the internal images of the organ in the subject 301. The capsule endoscope 302 sequentially and wirelessly sends the imaged internal images of the organ to the external receiving device 303. This capsule endoscope 302 includes a capsule endoscope body (hereinafter simply referred to as a capsule body) 302a that includes an imaging function to image internal images of the subject 301 and a wireless communication function to wirelessly send the internal images of the subject 301 to the outside; and floating members 302b and 302c attached onto external wall of the casing of the capsule body 302a so as to float the capsule body 302a in a predetermined position of the liquid.

The capsule body 302a sequentially images the internal images of the subject 301 in time series, and sequentially and wirelessly sends the imaged internal images of the subject 301 to the external receiving device 303. The floating members 302b and 302c are attached onto the external wall of the casing of the capsule body 302a, and function to float the capsule body 302a in the liquid in the organ of the subject 301. Specifically, the capsule body 302a and the floating members 302b and 302c are separately introduced into the organ of the subject 301. The capsule body 302a and the floating members 302b and 302c remain separate from each other, move inside the subject 301 by peristaltic movement of the organ or the like, and reach the inside of a desired organ to be observed. Inside the organ of this subject 301, the floating members 302b and 302c are attached onto the external wall of the casing of the capsule body 302a. In this case, the capsule endoscope 302 is in a state that the floating members 302b and 302c are mounted on the capsule body 302a inside the organ to be observed. This capsule endoscope 302 floats on the liquid such as water introduced into the organ to be observed. In this case, the capsule endoscope 302 (specifically, the capsule body 302a) floating in the liquid successively images the internal images of the subject 301 at predetermined intervals of, for example, 0.5 second. The capsule endoscope 302 successively sends the imaged internal images of the subject 301 to the receiving device 303.

The receiving device 303 is connected to a plurality of antennas 303a to 303h distributed and arranged, for example, on the body surface of the subject 301. The receiving device 303 receives a wireless signal from the capsule endoscope 302 (specifically, the capsule body 302a) through the plurality of receiving antennas 303a to 303h. The receiving device 303 acquires internal images of the subject 301 included in the received wireless signal. The portable recording medium 305 is detachably inserted into the receiving device 303. The receiving device 303 successively stores the internal images of the subject 301 on the portable recording medium 305. In this manner, the receiving device 303 stores the group of internal images of the subject 301 imaged by the capsule endoscope 302 (specifically, the capsule body 302a) on the portable recording medium 305.

The receiving antennas 303a to 303h are realized using, for example, a loop antenna, and receive a wireless signal sent by the capsule body 302a. Such receiving antennas 303a to 303h are distributed and arranged at positions corresponding to a predetermined position on the body surface of the subject 301, for example, a movement path of the capsule body 302a (i.e. an alimentary tract) in the subject 301. Note that the receiving antennas 303a to 303h may be distributed and arranged at a predetermined position of a jacket to be worn by the subject 301. In this case, the receiving antennas 303a to 303h are arranged at a predetermined position on the body surface of the subject 301 that corresponds to a movement path of the capsule body 302a in the subject 301 by the subject 301 wearing this jacket. One or more receiving antenna may be arranged for the subject 301, and the number of the receiving antenna(s) is not limited to eight.

The portable recording medium 305 is a portable recording medium such as CompactFlash (registered trademark). The portable recording medium 305 is detachable from the receiving device 303 and the image display device 304. The portable recording medium 305 is configured to perform outputting and recording of data when the portable recording medium 305 is inserted into the receiving device 303 and the image display device 304. Specifically, the portable recording medium 305 successively stores various data that includes the group of internal images of the subject 301 acquired by the receiving device 303 when the portable recording medium 305 is attached to the receiving device 303. When the portable recording medium 305 is inserted into the image display device 304, the portable recording medium 305 outputs the stored data such as the group of internal images of the subject 301 to the image display device 304. In this manner, the data stored on the portable recording medium 305 is read into the image display device 304. Patient information or the like about the subject 301 (i.e. a patient number, a patient ID or the like) is written onto the portable recording medium 305 by the image display device 304.

The image display device 304 is for displaying the internal images of the subject 301 imaged by the capsule body 302a. Specifically, the image display device 304 is configured like a workstation or the like for reading various data such as the group of internal images of the subject 301 through the above-described portable recording medium 305, and for displaying the acquired group of internal images of the subject 301. This image display device 304 has a process function for the user (a doctor, nurse or the like) to observe (examine) the internal images of the subject 301 so as to diagnose the subject 301. In this case, the user controls the image display device 304 to sequentially display the internal images of the subject 301, observes (examines) the region inside the subject (e.g. the esophagus, stomach, small intestine, and large intestine), and diagnoses the subject 301 based on the observation (examination).

Figure 19:
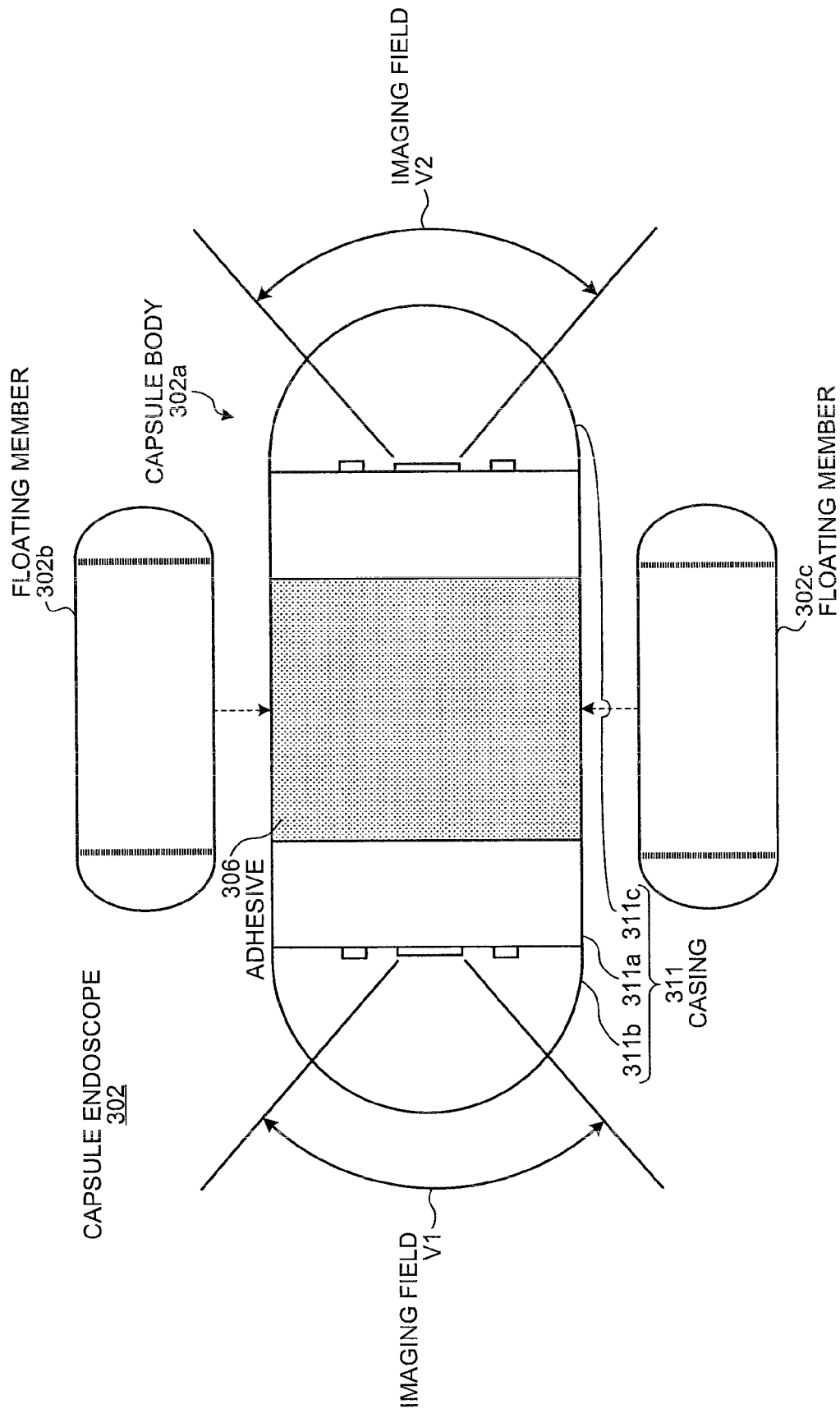
FIG. 19 is a schematic diagram showing one configuration example of the capsule endoscope according to the fourth embodiment of the present invention.
Figure 20:
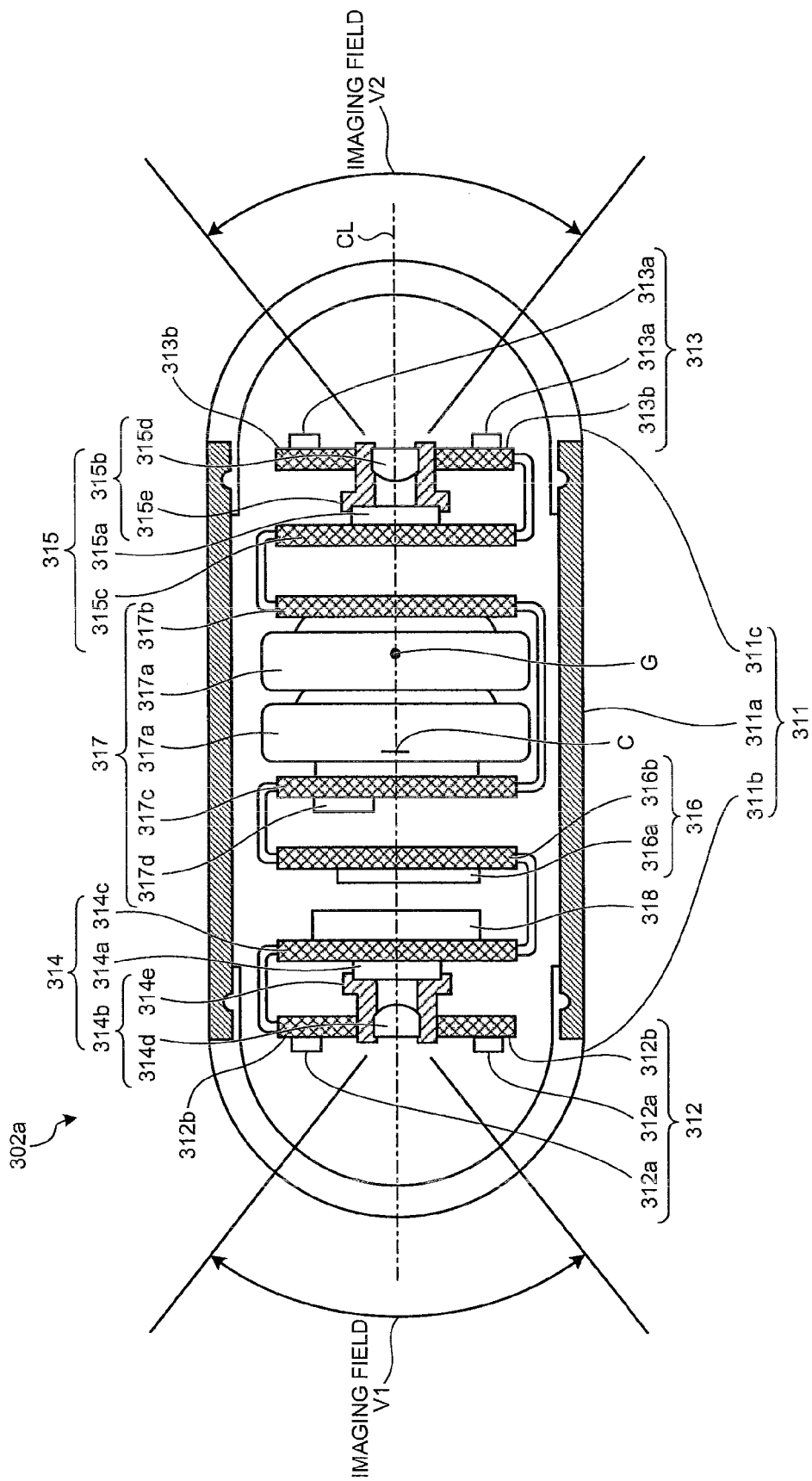
FIG. 20 is a side sectional schematic diagram showing one configuration example of a capsule body of the capsule endoscope according to the fourth embodiment of the present invention.

The configuration of the capsule endoscope 302 according to the fourth embodiment is explained. FIG. 19 is a schematic diagram showing a configuration example of the capsule endoscope 302 according to the fourth embodiment. FIG. 20 is a side sectional schematic diagram showing a configuration example of the capsule body 302a of the capsule endoscope 302 according to the fourth embodiment of the present invention.

As shown in FIG. 19, the capsule endoscope 302 according to the fourth embodiment has the multi-eye capsule body 302a that has imaging fields V1 and V2 in different directions from each other; the floating members 302b and 302c for floating the capsule body 302a in the liquid introduced into the organ of the subject 301; and an adhesive 306 for attaching the floating members 302b and 302c to the capsule body 302a. As shown in FIGS. 19 and 20, the capsule body 302a has a capsule casing 311; illuminating units 312 and 313 that illuminate the inside of the organ of the subject; imaging units 314 and 315 that image the internal images of the organ illuminated by the illuminating units 312 and 313, a wireless communication unit 316 that wirelessly sends each internal image of the subject imaged by the imaging units 314 and 315 to the outside; a power source unit 317 that supplies each constituent unit of the capsule body 302a with driving power; and a control unit 318 that controls each constituent unit of the capsule body 302a. Note that FIG. 20 does not show the adhesive 306 to be formed on the external wall surface of the casing 311.

As described above, the capsule body 302a has the imaging function to image the internal images of the organ in the subject 301 and the wireless communication function to sequentially and wirelessly send the imaged internal images of the organ to the external receiving device 303 outside the subject 301. Specifically, the capsule body 302a has the imaging fields V1 and V2 in different directions from each other, and alternately images the images of each subject (i.e. the internal images of the subject 301) in the imaging fields V1 and V2. The capsule body 302a sequentially and wirelessly sends the imaged internal images of the subject 301 to the external receiving device 303. For example, the two floating members 302b and 302c are attached onto the external wall of the casing 311 of the capsule body 302a inside the organ of the subject 301.

As described above, the floating members 302b and 302c remain separate from the capsule body 302a, and are introduced into the organ of the subject 301 so as to float the capsule body 302a in the liquid inside the organ. Specifically, the floating members 302b and 302c are hollow members made in the form of a capsule, using a meltable material e.g., gelatin in living organisms. The floating members 302b and 302c are hollow, and are attached onto the casing 311 of the capsule body 302a, and thus function as floats for floating the capsule body 302a in the liquid. In other words, the floating members 302b and 302c are attached onto the casing 311 of the capsule body 302a, thereby resulting in the specific gravity of the capsule endoscope 302 being equal to or lower than the specific gravity of predetermined liquid (liquid introduced into the organ of the subject 301). The floating members 302b and 302c melt when they touch the liquid having a predetermined pH value or lower (acid liquid such as acid in the stomach).

It is preferred that such floating members 302b and 302c be formed smaller than the casing 311 of the capsule body 302a as long as the specific gravity of the capsule endoscope 302 can be set equal to or lower than the specific gravity of the liquid inside the organ. Specifically, it is preferred that the length in the longitudinal direction of the capsule floating members 302b and 302c be shorter than the length in the longitudinal direction of the casing 311 of the capsule body 302a. Thereby, it becomes possible to easily prevent the entrance of the floating members 302b and 302c attached onto the external wall of the casing 311 into the imaging fields V1 and V2 of the capsule body 302a.

The casing 311 is a capsule casing having a size that can be easily introduced into the subject. The casing 311 has the external wall surface onto which the above-described floating members 302b and 302c are attached. The casing 311 includes the constituent units of the capsule body 302 therein. Specifically, the casing 311 is formed of a tubular casing body 311a and optical domes 311b and 311c.

The casing body 311a is a tubular casing both ends of which are open. The casing body 311a houses therein the constituent units of the capsule body 302a that are the illuminating units 312 and 313, the imaging units 314 and 315, the wireless communication unit 316, the power source unit 317 and the control unit 318. In this case, the illuminating unit 312 and the imaging unit 314 are fixed and arranged near one opening of the casing body 311a, while the illuminating unit 313 and the imaging unit 315 are fixed and arranged near the other opening thereof. The wireless communication unit 316, the power source unit 317 and the control unit 318 are arranged at the internal area of the casing body 311a placed between the imaging unit 314 and the imaging unit 315.

The optical domes 311b and 311c are transparent optical members in the form of a dome. Specifically, the optical dome 311b is mounted on one opening end of the casing body 311a (i.e. on the opening end on the side of the imaging field V1 where the illuminating unit 312 and the imaging unit 314 are fixed and arranged) so as to close this opening end. The optical dome 311c is mounted on the other opening end of the casing body 311a (i.e. on the opening end on the side of the imaging field V2 where the illuminating unit 313 and the imaging unit 315 are fixed and arranged) so as to close this opening end.

The casing 311, which is formed of the casing body 311a and the optical domes 311b and 311c on the both sides, liquid-tightly houses therein the constituent units of the capsule body 302a (the illuminating units 312 and 313, the imaging units 314 and 315, the wireless communication unit 316, the power source unit 317, the control unit 318, or the like). On the external wall surface of the casing body 311a, the adhesive 306 is applied in order to attach the floating members 302b and 302c thereonto.

The adhesive 306 functions as an attaching unit for detachably attaching the floating members 302b and 302c onto the external wall surface of the casing body 311a as areas outside the imaging fields V1 and V2. Specifically, the adhesive 306 is applied onto the external wall surface of the casing 311 as areas outside the imaging fields V1 and V2, i.e. the external wall surface of the casing body 311a. In this case, the adhesive 306 may be continuously applied (i.e. in a belt-like form) along the periphery of the casing body 311a, or may be applied partially in a desired position on the external wall surface of the casing body 311a. This adhesive 306 detachably attaches the floating members 302b and 302c onto the external wall surface of the casing body 311a as areas outside the imaging fields V1 and V2 inside the organ of the subject 301. As described above, the floating members 302b and 302c attached onto the external wall surface of the casing body 311a through the adhesive 306 are positioned in areas outside the imaging fields V1 and V2 so as not to obstruct the imaging fields V1 and V2.

The illuminating unit 312 functions as an illuminating unit for illuminating the inside of the organ in the subject 301 to be imaged by the imaging unit 314 (i.e. the subject in the imaging field V1). Specifically, the illuminating unit 312 is arranged on the side of the optical dome 311b inside the casing 311, and illuminates the subject of the imaging unit 314 through the optical dome 311b. This illuminating unit 312 has a plurality of light emitters 312a that emit illumination light toward the subject of the imaging unit 314; and an illumination board 312b that includes a circuit for realizing the function of the illuminating unit 312.

The plurality of light emitters 312a are mounted on the illumination board 312b, and emit illumination light to the imaging field V1 of the imaging unit 314 through the optical dome 311b. The plurality of light emitters 312a illuminate the subject imaged by the imaging unit 314 (i.e. the inside of the organ of the subject 301 positioned in the imaging field V1) using the illumination light. The illumination board 312b is a rigid circuit board of, for example, orbicular form, and is arranged on the side of the optical dome 311b inside the casing 311. A lens frame of the imaging unit 314 described later is inserted in the center part of the illumination board 312b.

The illuminating unit 313 functions as an illuminating unit for illuminating the inside of the organ of the board 301 (i.e. the subject in the imaging field V2) imaged by the imaging unit 315. Specifically, the illuminating unit 313 is arranged on the side of the optical dome 311c inside the casing 311, and illuminates the subject of the imaging unit 315 through the optical dome 311c. This illuminating unit 313 has a plurality of light emitters 313a that emit illumination light to the subject of the imaging unit 315; and an illumination board 313b that includes a circuit for realizing the function of the illuminating unit 313.

The plurality of light emitters 313a are mounted on the illumination board 313b, and emit illumination light to the imaging field V2 of the imaging unit 315 through the optical dome 311c. The plurality of light emitters 313a illuminate the subject imaged by the imaging unit 315 (i.e. the inside of the organ in the subject 301 positioned in the imaging field V2) using the illumination light. The illumination board 313b is a rigid circuit board of, for example, orbicular form, and is arranged on the side of the optical dome 311c inside the casing 311. A lens frame of the imaging unit 315 described later is inserted in the center part of the illumination board 313b.

The imaging unit 314 has the imaging field V1 in an imaging direction which is determined in accordance with the posture of the casing 311, and functions as an imaging unit for imaging the image of the subject in the imaging field V1. Specifically, the imaging unit 314 is fixed and arranged on the side of the optical dome 311b inside the casing 311, and images the image of the subject of the imaging field V1 (i.e. the inside of the organ in the imaging field V1) illuminated by the illuminating unit 312. This imaging unit 314 has a solid imaging device 314a such as a CCD or CMS; an optical system 314b that forms the image of the subject on the receiving surface of the solid imaging device 314a; and an imaging board 314c that includes a circuit for realizing the function of the imaging unit 314.

The solid imaging device 314a images the image of the subject illuminated by the illuminating unit 312. Specifically, the solid imaging device 314a has the imaging field V1 in an imaging direction determined in accordance with the posture of the casing 311. The solid imaging device 314a images the image of the subject in the imaging field V1 illuminated by the illuminating unit 312. More specifically, the solid imaging device 314a has a receiving surface for receiving the light from the subject positioned in the imaging field V1. The solid imaging device 314a performs photoelectric conversion for the light received from the subject through the receiving surface so as to image the image of the subject (i.e. the internal image of the organ in the subject 301 positioned in the imaging field V1).

The optical system 314b has a lens 314d that forms the image of the subject on the receiving surface of the solid imaging device 314a; and a lens frame 314e that holds this lens 314d. The lens 314d condenses the light from the subject positioned in the imaging field V1 on the receiving surface of the solid imaging device 314a so as to form the image of this subject on the receiving surface of the solid imaging device 314a.

The lens frame 314e has a tubular structure both ends of which are open, and holds the lens 314d inside the tube. Specifically, the lens frame 314e holds the lens 314d inside the tube near one opening thereof. The other end of the lens frame 314e is fixed on the solid imaging device 314a, introducing the light from the subject onto the receiving surface of the solid imaging device 314a. One end of the lens frame 314e (the side to hold the lens 314d) is inserted into the above-described illumination board 312b so as to be fixed on the illumination board 312b.

The imaging board 314c is a rigid circuit board of, for example, orbicular form, and is fixed and arranged on the side of the optical dome 311b inside the casing 311. Specifically, the imaging board 314c is fixed and arranged near the illumination board 312b and closer to the center C of the casing 311 as compared to the illumination board 312b. The above-described solid imaging device 314a and the control unit 318 are mounted on the imaging board 314c.

The imaging unit 315 has the imaging field V2 in an imaging direction determined in accordance with the posture of the casing 311. The imaging unit 315 functions as an imaging unit for imaging the image of the subject in the imaging field V2. Specifically, the imaging unit 315 is fixed and arranged on the side of the optical dome 311c inside the casing 311, and images the image of the subject in the imaging field V2 (i.e. the inside of the organ in the imaging field V2) illuminated by the illuminating unit 313. This imaging unit 315 has a solid imaging device 315a such as a CCD or CMOS, an optical system 315b that forms the image of the subject on the receiving surface of the solid imaging device 315a; and an imaging board 315c that includes a circuit for realizing the function of the imaging unit 315.

The solid imaging device 315a images the image of the subject illuminated by the illuminating unit 313. Specifically, the solid imaging device 315a has the imaging field V2 in an imaging direction determined in accordance with the posture of the casing 311 and different from that of the above-described imaging field V1. The solid imaging device 315a images the image of the subject of the imaging field V2 which is illuminated by the illuminating unit 313. More specifically, the solid imaging device 315a has a receiving surface for receiving the light from the subject positioned in the imaging field V2. In addition, the solid imaging device 315a performs photoelectric conversion for the light received from the subject 301 through this receiving surface so as to image the image of the subject (i.e. the internal image of the organ in the subject 301 positioned in the imaging field V2).

The optical system 315b has a lens 315d that forms the image of the subject on the receiving surface of the solid imaging device 315a; and a lens frame 315e that holds this lens 315d. The lens 315d condenses the light from the subject positioned in the imaging field V2 on the receiving surface of the solid imaging device 315a so as to form the image of this subject on the receiving surface of the solid imaging device 315a.

The lens frame 315e has a tubular structure both ends of which are open, and holds the lens 315d inside the tube. Specifically, the lens frame 315e holds the lens 315d inside the tube near one opening thereof. The other end of the lens frame 315e is fixed on the solid imaging device 315a, introducing the light from the subject onto the receiving surface of the solid imaging device 315a. One end of the lens frame 315e (the side of holding the lens 315d) is inserted into the above-described illumination board 313b so as to be fixed on the illumination board 313b.

The imaging board 315c is a rigid circuit board of, for example, orbicular form, and is fixed and arranged on the side of the optical dome 311c inside the casing 311. Specifically, the imaging board 315c is fixed and arranged near the illumination board 313b and closer to the center C of the casing 311 as compared to the illumination board 313b. The above-described solid imaging device 315a is mounted on the imaging board 315c.

As described above, each of the imaging fields V1 and V2 of the imaging units 314 and 315 is determined in accordance with the posture of the casing 311, and captures the subject (the inside of the organ in the subject 301) in different directions from the casing 311. In this case, the imaging unit 314 is fixed and arranged so that the optical axis of the imaging unit 314 as the center axis of the imaging field V1 is parallel to or on the same line as the center axis CL in the longitudinal direction of the casing 311. The imaging unit 315 sets the imaging field V2 in a direction opposite to that of the imaging field V1 of the imaging unit 314. The imaging unit 315 is fixed and arranged so that the optical axis of the imaging unit 315 as the center axis of the imaging field V2 is parallel to or on the same line as the center axis CL.

The wireless communication unit 316 functions as a wireless communication unit for sequentially and wirelessly sending each internal image of the subject imaged by each of the imaging units 314 and 315 to the external device 303 (see FIG. 18). Specifically, the wireless communication unit 316 is arranged between the imaging units 314 and 315 inside the casing 311, and sequentially and wirelessly sends each internal image of the organ as each subject of the imaging fields V1 and V2 to the receiving device 303. This wireless communication unit 316 has a wireless unit 316a that wirelessly sends each internal image of the subject to the receiving device 303, and a wireless board 316b that includes a circuit for realizing the function of the wireless communication unit 316.

The wireless unit 316a has a communication circuit that modulates an image signal including the internal image of the subject so as to generate a wireless signal; and an antenna that sends this wireless signal to the outside. Specifically, the wireless unit 316a receives the image signal including the internal image of the subject (i.e. the internal image of the organ in the imaging field V1) imaged by the above-described solid imaging device 314a. The wireless unit 316a performs a modulation process or the like for the received image signal so as to generate a wireless signal including the image of this subject. After that, the wireless unit 316a sequentially sends the wireless signal including the internal image of the organ in the imaging field V1 to the receiving device 303 outside the subject. Similarly, the wireless unit 316a receives the image signal including the internal image of the subject (i.e. the internal image of the organ in the imaging field V2) imaged by the above-described solid imaging device 315a. The wireless unit 316a performs a modulation process or the like for the received image signal so as to generate a wireless signal including the internal image of the subject. After that, the wireless unit 316a sequentially sends the wireless signal including the internal image of the organ in the imaging field V2 to the receiving device 303 outside the subject. This wireless unit 316a alternately generates a wireless signal including the internal image of the organ in the imaging field V1 and a wireless signal including the internal image of the organ in the imaging field V2, and alternately sends the generated wireless signals to the external receiving device 303. The wireless board 316b is a rigid circuit board of, for example, orbicular form, and is arranged, for example, between the imaging units 314 and 315 inside the casing 311. The wireless unit 316a is mounted on the wireless board 316b.

The power source unit 317 is fixed and arranged, for example, between the imaging unit 315 and the wireless communication unit 316 inside the casing 311. The power source unit 317 supplies each constituent unit of the capsule body 302a (i.e. the illuminating units 312 and 313, the image units 314 and 315, the wireless communication unit 316, the control unit 318, or the like) with driving power. This power source unit 317 has batteries 317a having predetermined electricity; power source boards 317b and 317c that include a circuit for realizing the function of the power source unit 317; and a switch 317d that switches ON/OFF states of power supply from the batteries 317a.

The batteries 317a are button-shaped batteries such as silver oxide batteries. A required number (e.g. two) of the batteries 317a are connected between the power source boards 317b and 317c as shown in FIG. 20. The power source boards 317b and 317c have a plus terminal and a minus terminal electrically connected to the batteries 317a. The power source boards 317b and 317c and the circuit board of each of the constituent units of the capsule body 302a (i.e. the illuminating units 312b and 313b, the imaging boards 314c and 315c and the wireless board 316b) are electrically connected through flexible boards or the like. The switch 317d is a reed switch for performing an ON/OFF switch operation by the external magnetic force, and is provided on the power source board 317c. Specifically, the switch 317d performs the ON/OFF switch operation so as to switch between the ON/OFF states of power supply from the batteries 317a. As a result, the switch 317d controls the batteries 317a to supply each constituent unit of the capsule body 302a with power electricity.

The controller 318 is mounted, for example, on the imaging board 314c, and controls each constituent unit of the capsule body 302a. Specifically, the control unit 318 controls each of the light emitters 312a and 313a of the above-described illuminating units 312 and 313, each of the solid imaging devices 314a and 315a of the imaging units 314 and 315, and the wireless unit 316a of the wireless communication unit 316. More specifically, the control unit 318 controls an operation timing of the plurality of light emitters 312a and the solid imaging device 314a so that the solid imaging device 314a images the image of the subject in the imaging field V1 at predetermined intervals in synchronization with a light emission operation of the plurality of light emitters 312a. The controller 318 also controls an operation timing of the plurality of light emitters 313a and the solid imaging device 315a so that the solid imaging device 315a images the image of the subject in the imaging field V2 at predetermined intervals in synchronization with a light emission operation of the plurality of light emitters 313a. The controller 318 alternately performs at predetermined time intervals the control of the light emitters 312a and the solid imaging device 314a, and the control of the light emitters 313a and the solid imaging device 315a. This controller 318 has various parameters about the imaging process such as white balancing or the like, and also has an image process function for alternately generating each of the image signals including each of the images of the subject alternately imaged by the solid imaging devices 314a and 315a. The controller 318 controls the wireless unit 316a to alternately send each of the images including the internal images of the subject to the wireless communication unit 316, and to alternately generate and output each of the wireless signals including the internal images of the subject.

The specific gravity and center of gravity of the capsule body 302a are explained with reference to FIG. 20. As described above, the capsule body 302a of the fourth embodiment is configured to include the illuminating units 312 and 313, the imaging units 314 and 315, the wireless communication unit 316, the power source unit 317 and the control unit 318, inside the casing 311 having a capsule form. When the floating members 302b and 302c are attached onto the external wall of the casing 311, the thus configured capsule body 302a floats in the liquid inside the organ. In other words, the specific gravity of the capsule endoscope 302 with the floating members 302b and 302c attached onto the casing 311 of the capsule body 302a is set equal to or lower than the specific gravity of predetermined liquid (e.g. water) introduced into the organ of the subject.

The specific gravity of the capsule body 302a may be set greater than the specific gravity of the liquid inside the organ as long as the capsule body 302a can float in the liquid of the organ by attaching the floating members 302b and 302c onto the external wall of the casing 311 using the above-described adhesive 306. The capsule body 302a having such a specific gravity can include the above-described illuminating units 312 and 313, the imaging units 314 and 315, the wireless communication unit 316, the power source unit 317 and the control unit 318, inside the casing 311 with high density. Thus, the external size of the capsule body 302a can be made approximately equal to or smaller than the capsule endoscope which sinks in the liquid inside the organ.

It is preferred that the capsule endoscope 302 formed with the capsule body 302a onto which the floating members 302b and 302c are attached float on the surface of the liquid inside the organ. In other words, it is preferred that the specific gravity of such a capsule endoscope 302 be so set that a part of the capsule endoscope 302 (e.g. the optical dome 311b) floats above the surface of the liquid inside the organ.

The center of gravity of the capsule body 302a is so set that the floating posture of the casing 311 floating in the liquid inside the organ is kept in a specific floating posture. Specifically, the center of gravity G of the capsule body 302a is set in a position away from the center C of the casing 311 by arranging the batteries 317a or the like of the power source unit 317 on the side of the optical dome 311c inside the casing 311, for example, with the center C of the casing 311 as a reference point. In this case, the center of gravity G is set on the opposite side of the above-described imaging unit 314 with the center C of the casing 311 as a reference point.

The center of gravity G of the capsule body 302a is thus set in a position away from the center C of the casing 311. As a result, the floating posture of the casing 311 floating in the liquid inside the organ is kept in a specific floating posture. Specifically, the floating posture of the casing 311 is kept in a specific floating posture in which the imaging field V1 of the imaging unit 314 is directed upwardly above the liquid inside the organ (i.e. the liquid on which the capsule endoscope 302 floats), and the imaging field V2 of the imaging unit 315 is directed under the liquid inside the organ due to the center of gravity G.

It is preferred that the center of gravity G be off the center C of the casing 311, or be set above or near the center axis CL of the casing 311. The floating posture of the casing 311 is kept in a specific floating posture, in which the imaging field V1 of the imaging unit 314 is directed to almost vertically upward, and the imaging field V2 of the imaging unit 315 is directed to almost vertically downward by setting the center of gravity G in such a position.

Figure 21:
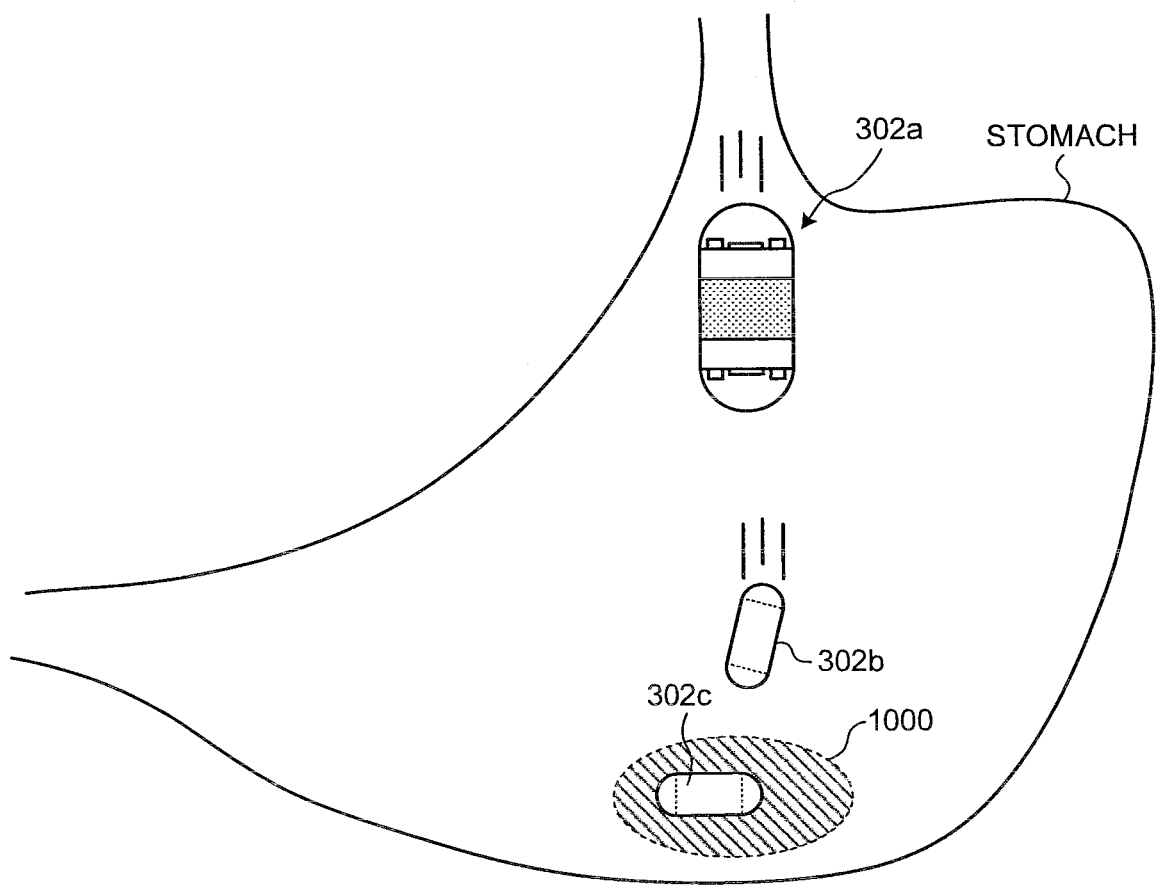
FIG. 21 is a schematic diagram exemplifying a state that the capsule body and a plurality of floating members are separately introduced into a stomach of a subject.
Figure 22:
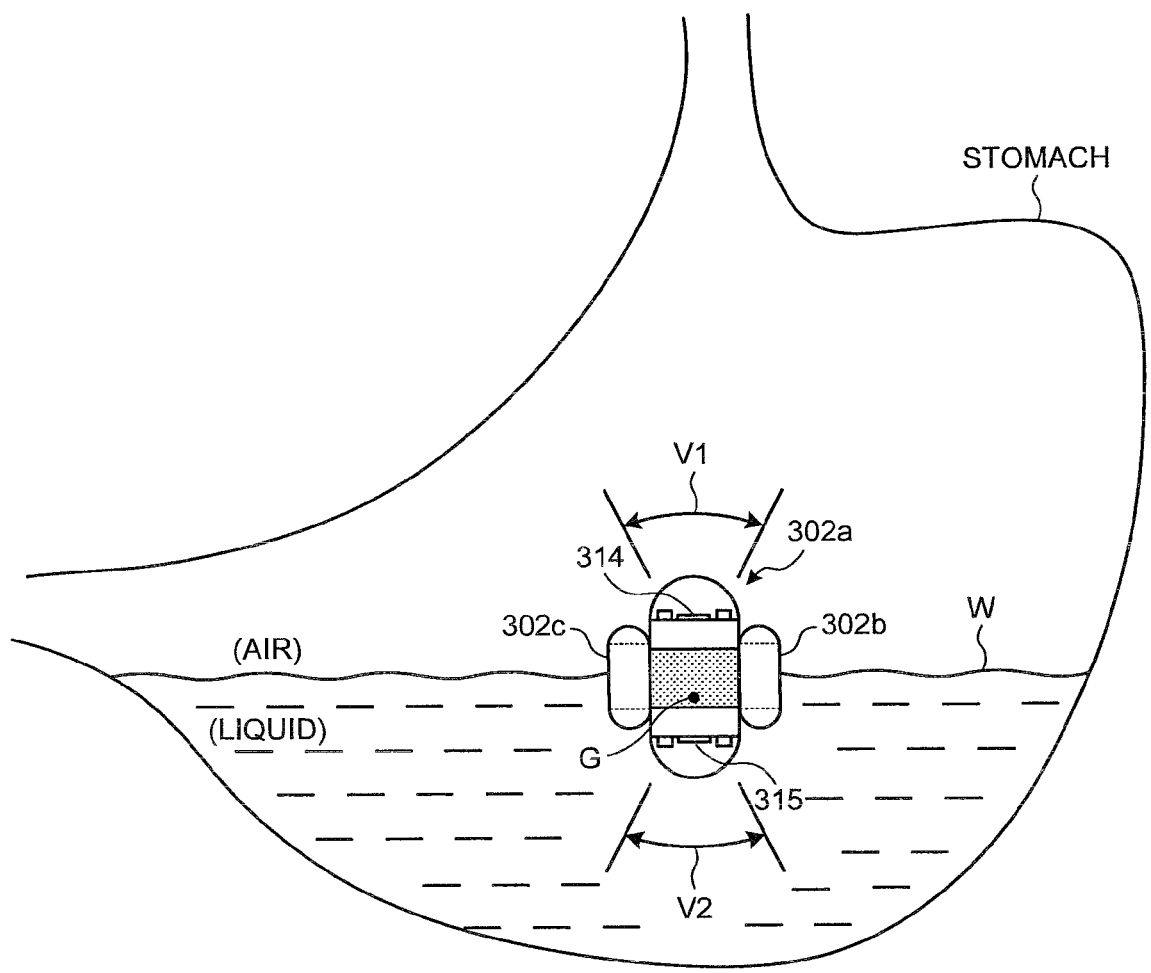
FIG. 22 is a schematic diagram exemplifying a state that the capsule endoscope according to the fourth embodiment floating on the surface of water inside the stomach sequentially images the internal images of the stomach.

An operation of the capsule endoscope 302 that images the internal images of the stomach in the subject 301 in a state that the capsule endoscope 302 and a required amount of water are introduced into the stomach of the subject, and that the capsule endoscope 302 floats on the surface of the water inside the stomach is explained. FIG. 21 is a schematic diagram exemplifying a state that, the capsule body 302a and the plurality of floating members 302b and 302c are separately introduced into the stomach of the subject. FIG. 22 is a schematic diagram exemplifying a state that the capsule endoscope 302 according to the fourth embodiment floating on the surface of the water inside the stomach sequentially images the internal images of the stomach.

The capsule endoscope 302 is swallowed from the mouth of the subject 301 in a state that the capsule body 302a and the plurality of floating members 302b and 302c are separate from each other. The capsule body 302a and the plurality of floating members 302a and 302c separately pass through the esophagus of the subject 301, and sequentially arrive at the stomach of the subject 301 as shown in FIG. 21.

The capsule body 302a may be swallowed by the subject 301 before the floating members 302b and 302c, but are preferably swallowed by the subject 301 after the floating members 302b and 302c. The reason is that the capsule body 302a can easily follow the floating members 302b and 302c when the capsule body 302a is swallowed after the floating members 302a and 302c. As a result, the floating members 302b and 302c are easily attached onto the external wall of the casing 311 inside of the organ.

When the subject 301 swallows the capsule body 302a and the plurality of floating members 302b and 302c while the subject 301 keeps approximately the same physical position, the capsule body 302a and the plurality of floating members 302b and 302c are concentrated in a partial area 1000 inside the stomach of the subject 301. The capsule body 302a and the plurality of floating members 302b and 302c concentrated in the partial area 1000 are integrated inside the stomach so as to form the capsule endoscope 302. Specifically, the capsule body 302a inside the stomach makes the plurality of floating members 302b and 302c attached onto the external wall of the casing 311, using the adhesive 306. In this case, the plurality of floating members 302b and 302c attached onto the external wall of the casing 311 of the capsule body 302a are positioned in the area outside the above-descried imaging fields V1 and V2. The specific gravity of the capsule endoscope 302 is set equal to or lower than that of water (i.e. 1 or lower) due to the floating members 302b and 302c.

After that, the subject 301 swallows a sufficient amount of water for floating the capsule endoscope 302 inside the stomach. In this manner, a required amount of water is introduced into the stomach of the subject 301. The capsule endoscope 302 which has already been introduced into the stomach and is floating on the surface of the required amount of water sequentially images the internal images of the stomach.

Specifically, as shown in FIG. 22, the capsule body 302a in the state that the floating members 302b and 302c are attached onto the external wall of the casing 311 floats on the surface of water W inside the stomach so as to be in a specific floating posture. The center of gravity of the capsule body 302a is set in a position away from the center C of the casing 311 and on the opposite side of the imaging unit 314 (preferably above the center axis CL) with the center C as a reference point. By setting the center of gravity in the above position, the floating capsule body 302a is in a specific floating posture on the surface of the water W (i.e. a floating posture in which the optical dome 311b floats above the water surface, while the optical dome 311c sinks in the water). In other words, due to the above center of gravity G, the capsule body 302a is kept in a floating posture in which the imaging field V1 is directed upwardly above the water W (to the air), while the imaging field V2 is directed under the surface (in the liquid) of the water W.

The capsule body 302a kept in the above floating posture alternately images the internal images of the stomach in the air above the water W and also internal images of the stomach in the liquid below the surface of the water W. In this case, the imaging unit 314 images the internal images of the stomach in the air as a subject of the imaging field V1 through the optical dome 311b. The imaging unit 315 images the internal images of the stomach in the liquid as a subject of the imaging field V2 through the optical dome 311c. The capsule body 302a in the floating posture sequentially images the internal images of the stomach in the air and also the internal images of the stomach in the liquid, with the result that the capsule body 302a can image the internal images of the entire stomach in the subject 301 in a short period of time efficiently. The capsule body 302a sequentially and wirelessly sends the internal images of the stomach in the air and also the internal images of the stomach in the liquid imaged alternately by the imaging units 314 and 315, to the receiving device 303 outside the subject 301.

After that, the water W floating the capsule endoscope 302 gradually flows out to the following organ (the duodenum) from the inside of the stomach. In this case, the amount of water inside the stomach decreases, thus increasing the acid concentration in the stomach. As a result, the pH value of the liquid in the stomach decreases to a predetermined value or lower (i.e. the acidity inside the stomach increases). The capsule endoscope 302 inside the stomach contacts the highly acid liquid.

As described above, the floating members 302b and 302c of the capsule endoscope 302 melt by acid liquid having a predetermined pH value or lower. Thus, the floating members 302b and 302c melt by the acid liquid inside the stomach so as to be a liquid state. In this case, the capsule body 302a inside the stomach leaves the floating members 302b and 302c so as to be a single body. The capsule body 302a as a single body remains separate from the floating members 302b and 302c, moves from the inside of the stomach into the following organ (duodenum or the like), and is discharged to the outside of the subject 301 through the small intestine and the large intestine.

The capsule body 302a has such an external size that the capsule body 302a can move inside the alimentary canal of the subject 301 by peristaltic movement thereof and the like.

In addition, it has already been proven that the capsule body 302a inside the subject 301 is safe during a period since the capsule body 302a is introduced into the organ until the capsule body 302a is naturally discharged. Thus, the capsule body 302a remaining separate from the floating members 302b and 302c can move inside the organ of the subject 301 without imposing excessive burden on the subject 301. The floating members 302b and 302c remaining separate from the capsule body 302a are formed smaller than the capsule endoscope 302a. Thus, the floating members 302b and 302c can move inside the organ of the subject 301 without imposing excessive burden on the subject 301.

As described above, in the fourth embodiment of the present invention, the capsule body (including the imaging function and wireless communication function inside the capsule casing) and the plurality of floating members are separate from each other, and are sequentially introduced into the organ of the subject. Furthermore, the plurality of floating members are attached onto the external wall of the casing of the capsule body inside the organ. The specific gravity of the capsule endoscope including the capsule body with the casing on which the plurality of floating members are attached is set equal to or lower than the specific gravity of the liquid inside the organ. Thereby, the capsule body and the plurality of floating members can be sequentially introduced into the organ to be observed in a state that the capsule body and the plurality of floating members have such sizes that they can easily move inside the organ of the subject, and the endoscope can be formed so that the plurality of floating members are attached onto the external wall of the casing of the capsule body inside the organ to be observed, without imposing excessive burden on the subject. This results in realizing such a capsule endoscope having a size capable of being easily swallowed when the capsule endoscope is introduced in the subject and capable of floating in the liquid inside the organ of the subject.

The floating members attached onto the external wall of the casing of the capsule body melt in the organ of the subject. Thus, the capsule body can be kept separate from the floating members when the capsule body moves from the organ to be observed into the following organ. As a result, the capsule body can be naturally discharged to the outside of the subject after imaging the internal images of the organ to be observed, without imposing excessive burden on the subject.

Furthermore, the floating members are detachably attached onto the external wall of the casing of the capsule body using the adhesive. Thus, the floating members can be easily detached, while the capsule body moves into the organ such as the duodenum. Even if the floating members remain unmelted on the external wall of the casing, the capsule body can be surely kept separate from the floating members when the capsule body moves from the inside of the organ to be observed into the following organ.

Fifth Embodiment

A fifth embodiment of the present invention is explained. In the fourth embodiment, the plurality of floating members 302b and 302c are detachably attached onto the casing 311 of the capsule body 302a using the adhesive 306. In the present embodiment, the floating members include a magnetic member, and a magnet is fixed and arranged inside the casing of the capsule body. The floating members are detachably attached onto the external wall of the casing of the capsule body by a magnetic force of the magnet.

Figure 23:
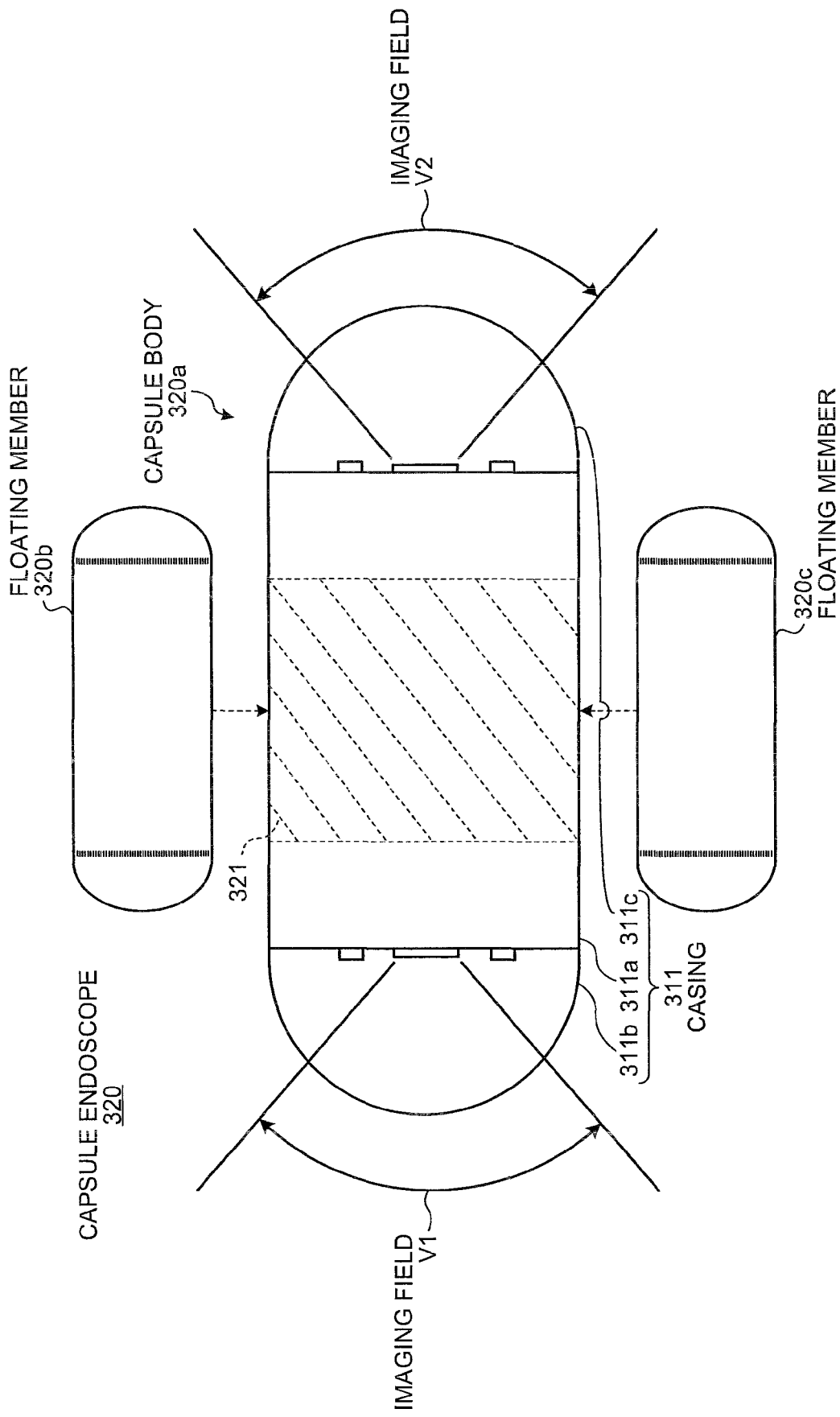
FIG. 23 is a schematic diagram showing one configuration example of a capsule endoscope according to a fifth embodiment of the present invention.
Figure 24:
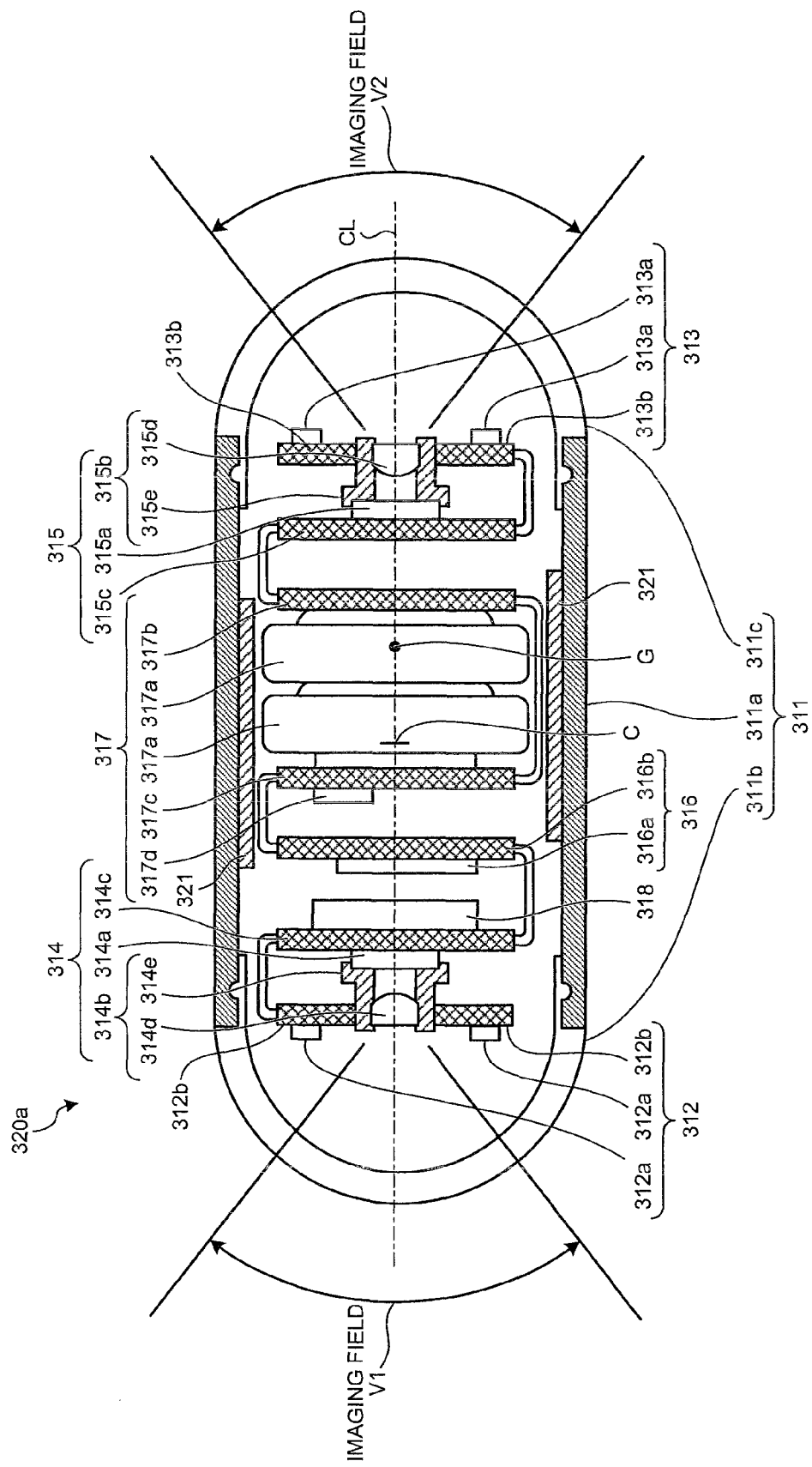
FIG. 24 is a side sectional schematic diagram showing one configuration example of a capsule body of a capsule endoscope according to the fifth embodiment of the present invention.

FIG. 23 is a schematic diagram showing a configuration example of a capsule endoscope according to the fifth embodiment of the present invention. FIG. 24 is a side sectional schematic diagram showing a configuration example of the capsule body of the capsule endoscope according to the fifth embodiment of the present invention. As shown in FIGS. 23 and 24, a capsule endoscope 320 according to the fifth embodiment has a capsule body 320a in place of the capsule body 302a of the capsule endoscope 302 according to the fourth embodiment, and has floating members 320b and 320c in place of the floating members 302b and 302c. This capsule body 320a has the same configuration as that of the capsule body 302a of the capsule endoscope 302 according to the fourth embodiment, and further has a magnet 321 inside the casing 311. An in-vivo information acquiring system according to the fifth embodiment has the capsule endoscope 320 in place of the capsule endoscope 302 according to the fourth embodiment. Any other configuration is the same as that of the fourth embodiment, and the same reference numeral is given to the same configuration unit.

The capsule body 320a has the same imaging function and the wireless communication function as those of the capsule body 302a according to the fourth embodiment. The floating members 320b and 320c are detachably attached onto the external wall of the casing 311 by the magnetic force of the magnet 321 fixed and arranged inside the casing 311. The floating members 320b and 320c are introduced into the organ of the subject 301 separately from the capsule body 320a like the floating members 302b and 302c according to the above-descried fourth embodiment so as to float the capsule body 320a in the liquid inside the organ. Specifically, the floating members 320b and 320c include a magnetic member added to a capsule hollow member using, for example, a resin member. The floating members 320b and 320c may include a filmy magnetic member (magnetic film) formed partially or entirely on the external wall surface of the capsule hollow member. A magnetic member in massive or film form may be formed on the internal wall surface of the capsule hollow member. The floating members 320b and 320c attached onto the casing 311 of the capsule body 320a function as floats for floating the capsule body 320a in the liquid. In other words, the floating members 320b and 320c are attached onto the casing 311 of the capsule body 320a so as to set the specific gravity of the capsule endoscope 320 equal to or lower than the specific gravity of predetermined liquid (i.e. liquid introduced into the organ of the subject 301).

The floating members 320b and 320c are preferably formed smaller than the casing 311 of the capsule body 320a as long as the specific gravity of the capsule endoscope 320 can be set equal to or lower than that of the liquid inside the organ. Specifically, the length of the capsule floating members 320b and 320c in the longitudinal direction is preferably shorter than the length of the casing 311 of the capsule body 320a in its longitudinal direction. Thereby, it becomes possible to easily prevent the entrance of the floating members 320b and 320c attached onto the external wall of the casing 311 into the imaging fields V1 and V2 of the capsule body 320a.

The magnet 321 functions as an attaching unit for detachably attaching the floating members 320b and 320c onto the external wall surface of the case body 311a as areas outside the imaging fields V1 and V2. Specifically, the magnet 321 is a bar-like or ring-like permanent magnet, and a required number of magnet(s) is (are) arranged on the internal wall surface of the casing body 311a of the casing 311. This magnet 321 generates a magnetic force near the outside of the casing 311 through the casing body 311a so as to detachably attach the floating members 320b and 320c onto the external wall surface of the casing body 311a as areas outside the imaging fields V1 and V2 by the magnetic force. Because the floating members 320b and 320c attached onto the external wall surface of the casing body 311a by the magnetic force of the magnet 321 are positioned in the areas outside the imaging fields V1 and V2 so as not to obstruct the imaging fields V1 and V2.

The specific gravity and center of gravity of the capsule body 320a are explained with reference to FIG. 24. As described above, the capsule body 320a of the capsule endoscope 320 according to the fifth embodiment is configured to include the illuminating units 312 and 313, the imaging units 314 and 315, the wireless communication unit 316, the power source unit 317, the control unit 318 and the magnet 321, inside the capsule casing 311. The thus configured capsule body 320a floats in the liquid inside the organ when the floating members 320b and 320c are attached onto the external wall of the casing 311 by the magnetic force of the magnet 321. In other words, the specific gravity of the capsule endoscope 320 with the floating members 320b and 320c attached onto the casing 311 of the capsule body 320a is set equal to or lower than the specific gravity of predetermined liquid (e.g. water) introduced into the organ of the subject.

The specific gravity of the capsule endoscope 320a may be greater than the specific gravity of liquid inside the organ to an extent that the capsule body 320a can float in the liquid inside the organ by attaching the floating members 320b and 320c onto the external wall of the casing 311 by the magnetic force of the magnet 321. The capsule body 320 having such specific gravity can include the illuminating units 312 and 313, the imaging units 314 and 315, the wireless communication unit 316, the power source unit 317, the control unit 318 and the magnet 321 that are described above inside the casing 311 with high density. Thus, the external size of the capsule body 320a can be made approximately the same or smaller than the capsule endoscope which sinks in the liquid in the organ.

The capsule endoscope 320 including the floating members 320b and 320c attached onto the capsule body 320a preferably floats on the surface of the liquid inside the organ. In other words, the specific gravity of the capsule endoscope 320 is preferably set so as to float a part of the capsule endoscope 320 (e.g. the optical dome 311b) from the surface of the liquid inside the organ.

As in the fourth embodiment, the center of gravity G of the capsule body 320a is set in a position away from the center C of the casing 311 by arranging the batteries 317a of the power source unit 317 or the like on the side of the optical dome 311c inside the casing 311 with the center C of the casing 311 as a reference point. In this case, the center of gravity G is set on the opposite side of the above-described imaging unit 314 with the center C of the casing 311 as a reference point.

Figure 25:
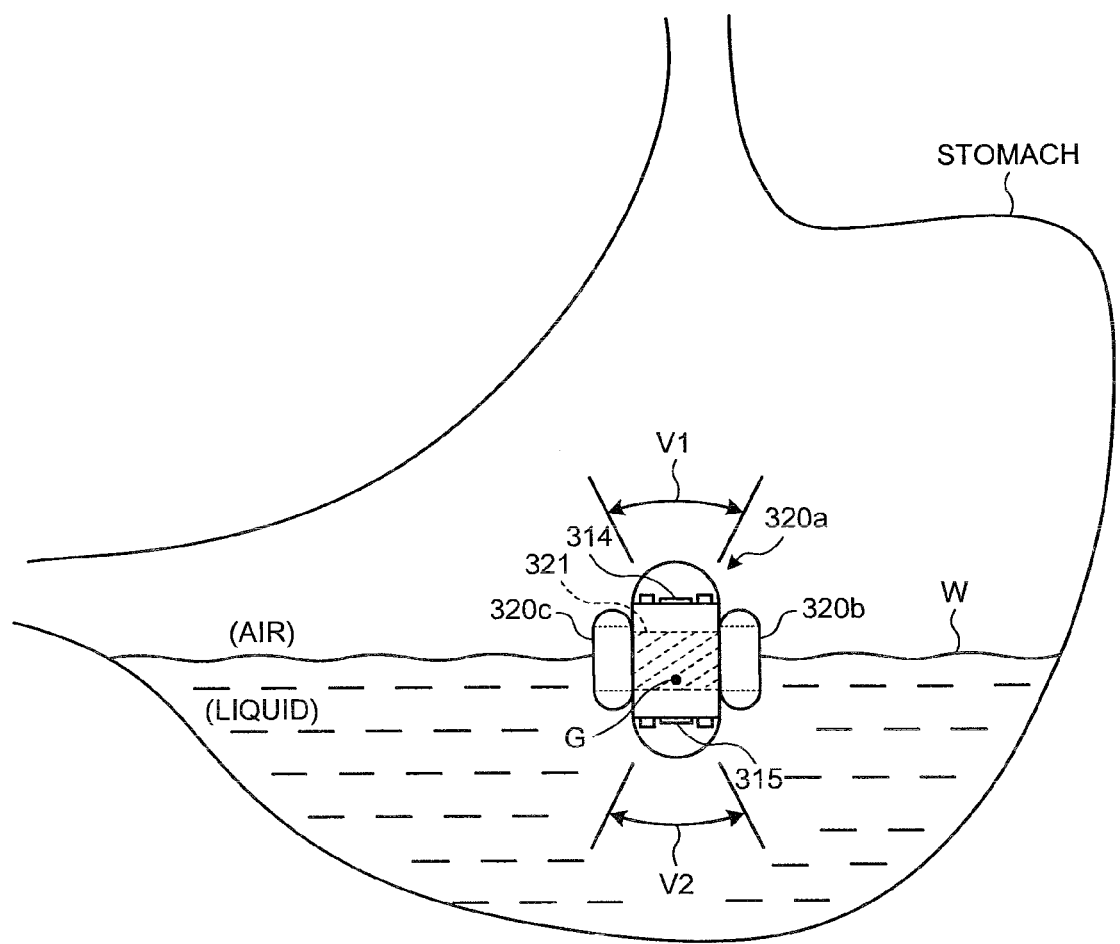
FIG. 25 is a schematic diagram exemplifying a state that the capsule endoscope according to the fifth embodiment floating on the surface of water inside the stomach sequentially images the internal images of the stomach.

An operation of the capsule endoscope 320 floating on the surface of water inside the stomach which images the internal images of the stomach in the subject 301 after the capsule endoscope 320 and a required amount of water are introduced into the stomach of the subject 301 is explained. FIG. 25 is a schematic diagram exemplifying a case that the capsule endoscope 320 according to the fifth embodiment floating floats on the water surface of the stomach sequentially images the internal images of the stomach.

The capsule endoscope 320 is swallowed from the mouth of the subject in a state that the capsule body 320a and the plurality of floating members 320b and 320c are separate from each other. As in the fourth embodiment, the capsule body 320a and the plurality of floating members 320b and 320c separately pass through the alimentary canal of the subject 301, and sequentially arrive at the stomach of the subject 301.

The capsule body 320a may be swallowed by the subject 301 before the floating members 320b and 320c, but are preferably swallowed by the subject 301 after the floating members 320b and 320c. The reason is that the capsule body 320a can easily follow the floating members 320b and 320c when the capsule body 320a is swallowed after the floating members 320a and 320c. As a result, the floating members 320b and 320c are easily attached onto the external wall of the casing 311 inside of the organ.

As in the fourth embodiment, the capsule body 320a and the floating members 320b and 320c separately swallowed from the mouth of the subject 301 are concentrated in the partial area 1000 (see FIG. 21) inside the stomach of the subject 301. The capsule body 320a and the plurality of floating members 320b and 320c concentrated in the partial area 1000 inside the stomach are integrated inside the stomach so as to form the capsule endoscope 320. Specifically, the capsule body 320a inside the stomach draws the plurality of floating members 320c and 320c by the magnetic force of the magnet 321. In addition, the capsule body 320a attaches the plurality of floating members 320b and 320c onto the external wall of the casing 311 by the magnetic force. In this case, the plurality of floating members 320b and 320c attached onto the external wall of the casing 311 of the capsule body 320a are positioned in areas outside the imaging fields V1 and V2. The specific gravity of the capsule endoscope 320 is set equal to or lower (i.e. 1 or lower) than the specific gravity of water by the floating members 320b and 320c.

After that, the subject 301 swallows a sufficient amount of water for floating the capsule endoscope 320 inside the stomach. In this manner, a required amount of water is introduced into the stomach of the subject 301. The capsule endoscope 320 having been introduced into the stomach and floating on the surface of the required amount of water sequentially images the internal images of the stomach.

Specifically, as shown in FIG. 25, the capsule body 320a with the floating members 320b and 320c attached onto the external wall of the casing 311 by the magnetic force floats on the surface of the water W inside the stomach so as to be in a specific floating posture. As in the fourth embodiment, the center of gravity G of the capsule body 320a is set in a position away from the center C of the casing 311, and is set on the opposite side of the imaging unit 314 (preferably above the center axis CL) with the center C as a reference point. The capsule body 320a in the floating posture is in a specific floating posture on the surface of the water W (i.e. a floating posture where the optical dome 311b floats above the water surface and the optical dome 311c sinks in the water) by setting the center of gravity G in the above position. In other words, the capsule body 320a is kept in a floating posture in which the capsule body 320a directs the imaging field V1 of the imaging unit 314 upwardly above the water W (i.e. in the air), and directs the imaging field V2 of the imaging unit 315 below the water surface (in the liquid) of the water W due to the center of gravity G thereof.

As in the fourth embodiment, the capsule body 320a in the above floating posture alternately images the internal images of the stomach in the air positioned above the water W and the internal images of the stomach in the liquid positioned under the surface of the water W. The capsule body 320a in the floating state sequentially images the internal images of the stomach in the air and the internal images of the stomach in the liquid. Accordingly, the capsule body 320a can efficiently image the internal images of the entire stomach in the subject 301 in a short period of time. The capsule body 320a sequentially and wirelessly sends the internal images of the stomach in the air and the internal images of the stomach in the liquid alternately imaged by the imaging units 314 and 315 to the receiving device 303 outside the subject 301.

After that, the water W floating the capsule endoscope 320 gradually flows out to the following organ (such as the duodenum) from the inside of the stomach. The capsule endoscope 320 begins to move from the inside of the stomach to the following organ by the effect of flowing water W. The floating members 320*b* and 320*c* of the capsule endoscope 320 are detachably attached onto the external wall of the casing 311 by the magnetic force of the magnet 321. The floating members 320*b* and 320*c* contact the internal wall of the organ when the capsule body 320*a* moves inside the small organ (such as the duodenum) so as to be out of the magnetic field of the magnet 321.

Thus, the capsule body 320*a* can easily detach the floating members 320*b* and 320*c* therefrom while the capsule body 320*a* moves from the inside of the stomach to the duodenum, and can move into the following organ such as the duodenum separately from the floating members 320*b* and 320*c*. The capsule body 320*a* remains separate from the floating members 320*b* and 320*c*, moves from the inside of the stomach into the following organ (such as the duodenum), and then discharged to the outside of the subject 301 through the small intestine and the large intestine.

The capsule body 320*a* has such an external size that the capsule body 320*a* can move inside the alimentary canal of the subject 301 by peristaltic movement thereof. In addition, it has already been proven that the capsule body 320*a* inside the subject 301 is safe during a period since the capsule body 320*a* is introduced into the organ until the capsule body 320*a* is naturally discharged. Thus, the capsule body 320*a* remaining separate from the floating members 320*b* and 320*c* can move inside the organ of the subject 301 without imposing excessive burden on the subject 301. The floating members 320*b* and 320*c* remaining separate from the capsule body 320*a* are formed smaller than the capsule body 320*a*. Thus, the floating members 320*b* and 320*c* can easily move inside the organ of the subject 301 without imposing excessive burden on the subject 301.

As described above, in the fifth embodiment of the present invention, the magnet is arranged at place of the adhesive inside the casing of the capsule body having approximately the same configuration as that of the fourth embodiment, and the plurality of floating members include a magnetic member. The capsule body and the plurality of floating members that are separate from each other, and are introduced sequentially into the organ of the subject, and are attached onto the external wall of the casing of the capsule body inside the organ by the magnetic force. The specific gravity of the capsule endoscope with the plurality of floating members attached onto the external wall of the casing of the capsule body is set equal to or lower than that of the liquid inside the organ. This results in realizing an in-vivo information acquiring apparatus, which provides the operating effect of the fourth embodiment 4, and which enables to integrate the capsule body with the plurality of floating members separately introduced into the organ by the magnetic force, and which also enables to float in the liquid inside the organ to be observed without imposing excessive burden on the subject.

The plurality of floating members are attached onto the external wall of the casing of the capsule body by the magnetic force. Thus, the floating members can be easily detached from the capsule body when the capsule body moves from the inside of the organ to be observed into the following organ (e.g. a narrow organ such as a duodenum). As a result, it is possible to easily separate the capsule body and the floating members which begin to move into the following organ, and it is also possible to naturally discharge the capsule body and the floating members from the subject after the capsule body and the floating members image the internal images of the organ to be observed, without imposing excessive burden on the subject.

In the fourth and fifth embodiments, the capsule endoscope includes the floating members attached onto the multi-eye capsule body having the two imaging units 314 and 315 inside the casing 311. However, the configuration is not limited to this. The capsule endoscope may include the floating members attached onto a single eye capsule body having one imaging unit inside the capsule casing.

Specifically, as shown in FIG. 26, the capsule endoscope 330 according to a modification of the present invention may be configured to include the plurality of floating units 302*b* and 302*c* attached onto the external wall of the casing of the single eye capsule 330*a* having the single imaging field V1. The casing 331 of the capsule body 330*a* includes a cylindrical casing body 331*a* that has one opening end and the other end closed in a dome-like form; and the optical dome 311*b* attached on one end (opening end) of the casing body 331*a*. The capsule body 330*a* may include the imaging function to image the images of the subject in the imaging field V1, and a wireless communication function to send the images of the subject in the imaging field V1 to the receiving device 303, inside the casing 331 as exemplified by the illuminating unit 312, the imaging unit 314, the wireless communication unit 316, the power source unit 317 and the control unit 318 that are described above.

In this capsule endoscope 330, the plurality of floating members 302*b* and 302*c* may be detachably attached onto the external wall of the casing body 331*a* with the adhesive 306, as in the fourth embodiment. The plurality of floating members 302*b* and 302*c* may be detachably attached onto the dome-like end of the casing body 331*a* with the adhesive 306 as shown in FIG. 26. The capsule endoscope 330 that includes the plurality of floating members 302*b* and 302*c* attached onto the dome-like end and is floating in the liquid inside the organ directs the imaging field V1 into the liquid. In this case, the center of gravity of the capsule body 330*a* may not be set in a position away from the center of the casing 331, and may be set in an arbitrary position such as the center of the casing 331.

The floating members 320*b* and 320*c* including the magnetic member may be attached onto the external wall of the casing 331 in place of the plurality of floating members 302*b* and 302*c*. In this case, as in the fifth embodiment, the capsule body 330*a* has the ring-like or bar-like magnet 321 inside the casing body 331*a* of the casing 331, and thus detachably attaches the floating members 320*b* and 320*c* onto the external wall of the casing 331 by the magnetic force of the magnet 321. The magnet 321 may be arranged on the internal wall of the dome-like end of the casing 331, and the floating members 302*b* and 302*c* may be detachably attached on the dome-like end of the casing 331 by the magnetic force of the magnet 321. In this case, the center of gravity of the capsule body 330*a* of the capsule endoscope 330 may not be set in a position away from the center of the casing 331, and may be set in an arbitrary position such as the center of the casing 331.

In the modification of the fourth and fifth embodiments of the present invention, two floating members are attached onto the external wall of the casing of the capsule body. However, the configuration is not limited to this. One or more floating member may be attached on the external wall of the casing of the capsule body of this capsule endoscope as long as the center of gravity of the capsule endoscope can be set equal to or lower than the center of gravity of the liquid inside the organ.

In the fourth and fifth embodiments of the present invention, the two floating members are introduced into the organ of the subject. However, the configuration is not limited to this. Only one floating member sufficient for floating the capsule body in the liquid of the organ may be introduced into the organ of the subject. However, it is preferred that a plurality of floating members be sequentially introduced separately from each other. If the plurality of floating members are separately introduced into the organ of the subject, one or more floating member can be surely attached onto the external wall of the casing of the capsule body inside this organ. The same applies to the modification of the present invention that exemplifies the above-described capsule endoscope 330.

In the fourth and fifth embodiments and modification of the present invention, the capsule floating members have been exemplified. However, the configuration is not limited to this. The floating members attached onto the external wall of the capsule body may be round members having a spherical or elliptical external shape, but preferably have the above-described capsule form. The reason is that the capsule floating members are easily attached onto the external wall of the casing because the area that contacts the external wall of the casing is larger than that of the spherical shape members when they are attached onto the external wall of the casing of the capsule body.

In the embodiment of the present invention, the floating members 302b and 302c melt inside the organ of the subject 301. However, the configuration is not limited to this. The floating members 302b and 302c may be formed with a material (such as a resin material) that does not melt inside the organ, and thus may be naturally discharged to the outside of the subject as in the fifth embodiment.

In the fifth embodiment of the present invention, the floating members 320b and 320c do not melt inside the organ and are naturally discharged to the outside of the subject. However, the configuration is not limited to this. The floating members 320b and 320c may be formed of a material (gelatin or the like), which is meltable inside the organ, and a magnetic material, and may melt inside the organ as in the fourth embodiment.

In the fourth embodiment of the present invention, the floating members 302b and 302c melt by acid liquid having a predetermined pH value or lower. However, the configuration is not limited to this. The floating members 302b and 302c may melt by enzymes, or may melt when a predetermined period of time has elapsed inside the organ. The same applies to the floating members 320b and 320c including a magnetic material.

In the fourth and fifth embodiments of the present invention, the imaging fields V1 and V2 are directed in opposite directions to each other. However, the configuration is not limited to this. The imaging fields V1 and V2 have only to be directed simply in different directions. In this case, the center axis of the imaging field V1 (optical axis of the imaging unit 314) may be parallel to or on the same line as the imaging field V2 (optical axis of the imaging unit 315), or may be inclined with respect to the center axis CL of the casing 311.

In the fifth embodiment of the present invention, the capsule casing includes the magnet, and the floating member includes magnetic material. However, the configuration is not limited to this. The capsule casing may include a magnetic material, and the floating member includes a magnet. Furthermore, the same effect can be obtained when both of the capsule casing and the floating member include a magnet.

Furthermore, in the fifth embodiment of the present invention, the magnet of the capsule casing may be a permanent magnet or an electromagnet. When an electromagnet is used, the floating member can be attracted by flowing current, and the floating member can be detached by stopping the current. Therefore, after the capsule casing and the floating member are swallowed, an electric current is flown to the electromagnet, the floating member is attracted, the electric current is stopped to flow after examination, the floating member is detached therefrom, and thus the passage after the examination can be improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope system comprising:
   a capsule endoscope which is introduced into a subject;
   a change unit which changes a position or posture of the capsule endoscope in the subject with respect to the subject;
   a storage unit which stores in advance, as a control parameter of the change unit, a plurality of change procedures that cause the capsule endoscope to face observation directions for a plurality of observed regions set in advance; and
   a control unit which controls the change unit in accordance with the parameter stored in the storage unit;
   wherein the change unit is a mounting bed for mounting the subject thereon and the control unit controls a posture of the mounting bed.

2. The capsule endoscope system according to claim 1, wherein the capsule endoscope is kept in a predetermined posture with respect to a gravity direction in liquid introduced into the subject.

3. The capsule endoscope system according to claim 2, wherein the capsule endoscope floats in the liquid introduced into the subject.

4. The capsule endoscope system according to claim 1, wherein the storage unit stores a keeping time for keeping a change state as a parameter for each change state of the capsule endoscope.

5. A capsule endoscope system comprising:
   a capsule endoscope which is introduced into a subject;
   a change unit which changes a position or posture of the capsule endoscope in the subject with respect to the subject;
   a storage unit which stores in advance a change procedure of the capsule endoscope as a control parameter of the change unit; and
   a control unit which controls the change unit in accordance with the parameter stored in the storage unit, wherein
   the change unit is a mounting bed for mounting the subject thereon,
   the control unit controls a posture of the mounting bed, and
   the capsule endoscope is kept in a predetermined posture in a gravity direction in the subject.

6. The capsule endoscope system according to claim 5, wherein the storage unit stores in advance, as the control parameter of the change unit, a plurality of change procedures that cause the capsule endoscope to face observation directions for a plurality of observed regions set in advance.

7. The capsule endoscope system according to claim 5, wherein
- the mounting bed has a plurality of legs that can be extended or shortened independently from each other, and
- the change procedure includes length information representing a change amount of each of the legs.

* * * * *